US011111495B2

(12) United States Patent
Zichi et al.

(10) Patent No.: US 11,111,495 B2
(45) Date of Patent: Sep. 7, 2021

(54) METHOD FOR GENERATING APTAMERS WITH IMPROVED OFF-RATES

(71) Applicant: SomaLogic, Inc., Boulder, CO (US)

(72) Inventors: Dominic Zichi, Boulder, CO (US); Sheri K. Wilcox, Longmont, CO (US); Chris Bock, Cleveland Heights, OH (US); Daniel J. Schneider, Arvada, CO (US); Bruce Eaton, Longmont, CO (US); Larry Gold, Boulder, CO (US)

(73) Assignee: Somalogic, Inc., Boulder, CO (US)

( * ) Notice: Subject to any disclaimer, the term of this patent is extended or adjusted under 35 U.S.C. 154(b) by 131 days.

(21) Appl. No.: 16/414,026

(22) Filed: May 16, 2019

(65) Prior Publication Data

US 2019/0330634 A1 Oct. 31, 2019

Related U.S. Application Data

(60) Continuation of application No. 15/878,161, filed on Jan. 23, 2018, now Pat. No. 10,316,321, which is a continuation of application No. 15/410,414, filed on Jan. 19, 2017, now abandoned, which is a continuation of application No. 14/610,758, filed on Jan. 30, 2015, now abandoned, which is a continuation of application No. 13/113,261, filed on May 23, 2011, now Pat. No. 8,975,388, which is a division of application No. 12/175,434, filed on Jul. 17, 2008, now Pat. No. 7,947,447, which is a continuation-in-part of application No. 60/950,283, filed on Jul. 17, 2007, and a continuation-in-part of application No. 11/623,535, filed on Jan. 16, 2007, now abandoned, and a continuation-in-part of application No. 11/623,580, filed on Jan. 16, 2007, now abandoned.

(60) Provisional application No. 61/051,594, filed on May 8, 2008, provisional application No. 61/031,420, filed on Feb. 26, 2008, provisional application No. 60/950,293, filed on Jul. 17, 2007, provisional application No. 60/950,281, filed on Jul. 17, 2007.

(51) Int. Cl.
| | |
|---|---|
| *C12N 15/115* | (2010.01) |
| *C12Q 1/6816* | (2018.01) |
| *C12Q 1/6832* | (2018.01) |
| *C12Q 1/6834* | (2018.01) |
| *G01N 33/53* | (2006.01) |
| *G01N 33/58* | (2006.01) |
| *C12Q 1/6811* | (2018.01) |
| *C12N 9/74* | (2006.01) |
| *C12N 15/10* | (2006.01) |

(52) U.S. Cl.
CPC .......... *C12N 15/115* (2013.01); *C12N 9/6429* (2013.01); *C12N 15/1048* (2013.01); *C12Q 1/6811* (2013.01); *C12Q 1/6816* (2013.01); *C12Q 1/6832* (2013.01); *C12Q 1/6834* (2013.01); *G01N 33/5308* (2013.01); *G01N 33/58* (2013.01); *C12N 2310/16* (2013.01); *C12N 2310/314* (2013.01); *C12N 2310/315* (2013.01); *C12N 2310/321* (2013.01); *C12N 2310/322* (2013.01); *C12N 2310/333* (2013.01); *C12N 2310/334* (2013.01); *C12N 2310/335* (2013.01); *C12N 2310/336* (2013.01); *C12N 2330/31* (2013.01)

(58) Field of Classification Search
None
See application file for complete search history.

(56) References Cited

U.S. PATENT DOCUMENTS

| | | | |
|---|---|---|---|
| 4,267,171 A | 5/1981 | Bergstrom et al. | |
| 4,415,732 A | 11/1983 | Caruthers et al. | |
| 4,562,157 A | 12/1985 | Lowe et al. | |
| 4,594,339 A | 6/1986 | Lopez et al. | |
| 4,711,955 A | 12/1987 | Ward | |
| 4,725,677 A | 2/1988 | Koster | |
| 4,737,453 A | 4/1988 | Primus et al. | |

(Continued)

FOREIGN PATENT DOCUMENTS

| | | |
|---|---|---|
| AU | 47586/90 | 11/1989 |
| CN | 1436082 A | 8/2003 |

(Continued)

OTHER PUBLICATIONS

Agathocleous and Shaw (1991) J. Chem. Soc. Perkin Trans. 1: 2317-2321, "Purines, pyrimidines and imidazoles. Part 66. New Synthesis of some uridine and N-alkoxycarbonyl 5-carboxyamides, N-carbomoyl 5-carboxyamides and 5-carboxyamides".
Bartel et al. (1991) Cell 67:529-536, "HIV-1 Rev Regulation Involves Recognition of Non-Watson-Crick Base Pairs in Viral RNA".
Bass and Cech, (1984) Nature 308:820-826 "Specific Interaction Between the Self-Splicing RNA of Tetrahymena and its Guanosine Substrate: Implications for Biological Catalysis by RNA".

(Continued)

*Primary Examiner* — Tracy Vivlemore

(74) *Attorney, Agent, or Firm* — Leydig, Voit & Mayer, Ltd.

(57) ABSTRACT

The present disclosure describes improved SELEX methods for producing aptamers that are capable of binding to target molecules and improved photoSELEX methods for producing photoreactive aptamers that are capable of both binding and covalently crosslinking to target molecules. Specifically, the present disclosure describes methods for producing aptamers and photoaptamers having slower dissociation rate constants than are obtained using prior SELEX and photo-SELEX methods. The disclosure further describes aptamers and photoaptamers having slower dissociation rate constants than those obtained using prior methods. In addition, the disclosure describes aptamer constructs that include a variety of functionalities, including a cleavable element, a detection element, and a capture or immobilization element.

5 Claims, 31 Drawing Sheets

Specification includes a Sequence Listing.

(56) References Cited

U.S. PATENT DOCUMENTS

| | | |
|---|---|---|
| 4,752,566 A | 6/1988 | Collins et al. |
| 4,828,979 A | 5/1989 | Kelvan et al. |
| 4,948,882 A | 8/1990 | Ruth |
| 4,997,818 A | 3/1991 | McCaffrey et al. |
| 5,023,243 A | 6/1991 | Tullis |
| 5,047,519 A | 9/1991 | Hobbs, Jr. et al. |
| 5,093,232 A | 3/1992 | Urdea et al. |
| 5,118,672 A | 6/1992 | Schinazi et al. |
| 5,124,246 A | 6/1992 | Urdea et al. |
| 5,134,066 A | 7/1992 | Rogers et al. |
| 5,138,045 A | 8/1992 | Cook et al. |
| 5,223,409 A | 6/1993 | Ladner et al. |
| 5,270,163 A | 12/1993 | Gold et al. |
| 5,412,087 A | 5/1995 | McGall et al. |
| 5,428,149 A | 6/1995 | Eaton |
| 5,475,096 A | 12/1995 | Gold et al. |
| 5,476,766 A | 12/1995 | Gold et al. |
| 5,496,938 A | 3/1996 | Gold et al. |
| 5,527,894 A | 6/1996 | Gold et al. |
| 5,543,293 A | 8/1996 | Gold et al. |
| 5,567,588 A | 10/1996 | Gold et al. |
| 5,576,429 A | 11/1996 | Johansson et al. |
| 5,580,737 A | 12/1996 | Polisky |
| 5,580,972 A | 12/1996 | Tu |
| 5,582,981 A | 12/1996 | Toole et al. |
| 5,591,843 A | 1/1997 | Eaton et al. |
| 5,595,877 A | 1/1997 | Gold et al. |
| 5,596,091 A | 1/1997 | Switzer |
| 5,599,720 A | 2/1997 | Ekins et al. |
| 5,633,361 A | 5/1997 | Eaton et al. |
| 5,639,868 A | 6/1997 | Janjic et al. |
| 5,645,985 A | 7/1997 | Froehler |
| 5,660,985 A | 8/1997 | Pieken et al. |
| 5,681,697 A | 10/1997 | Urdea et al. |
| 5,705,337 A | 1/1998 | Gold et al. |
| 5,719,273 A | 2/1998 | Tu et al. |
| 5,723,323 A | 3/1998 | Kauffman et al. |
| 5,756,291 A | 5/1998 | Griffin et al. |
| 5,801,154 A | 9/1998 | Baracchini et al. |
| 5,817,785 A | 10/1998 | Gold et al. |
| 5,840,867 A | 11/1998 | Toole et al. |
| 5,843,653 A | 12/1998 | Gold et al. |
| 5,861,254 A | 1/1999 | Schneider et al. |
| 5,945,527 A | 8/1999 | Tu et al. |
| 5,958,691 A | 9/1999 | Pieken |
| 5,962,225 A | 10/1999 | Ramberg |
| 6,020,483 A | 2/2000 | Beckvermit et al. |
| 6,030,776 A | 2/2000 | Eaton et al. |
| 6,175,001 B1 | 1/2001 | Barbas et al. |
| 6,184,364 B1 | 2/2001 | Pieken et al. |
| 6,232,462 B1 | 5/2001 | Collins et al. |
| 6,329,145 B1 | 12/2001 | Janjic et al. |
| 6,344,318 B1 | 2/2002 | Gold et al. |
| 6,344,321 B1 | 2/2002 | Rabin et al. |
| 6,346,611 B1 | 2/2002 | Pagratis et al. |
| 6,355,787 B1 | 3/2002 | Beckvermit et al. |
| 6,716,583 B2 | 4/2004 | Gold et al. |
| 7,368,236 B2 | 5/2008 | Gold et al. |
| 7,855,054 B2 | 12/2010 | Schneider et al. |
| 7,947,447 B2 | 5/2011 | Zichi et al. |
| 7,964,356 B2 | 6/2011 | Zichi et al. |
| 8,404,830 B2 | 3/2013 | Zichi et al. |
| 9,404,919 B2 | 8/2016 | Schneider et al. |
| 2002/0009767 A1 | 1/2002 | Muraca |
| 2003/0148335 A1 | 8/2003 | Shen et al. |
| 2003/0162216 A1 | 8/2003 | Gold et al. |
| 2003/0219801 A1 | 11/2003 | Lipshutz |
| 2003/0228603 A1 | 12/2003 | Cload et al. |
| 2004/0072234 A1 | 4/2004 | Parma et al. |
| 2004/0106145 A1 | 6/2004 | Gold et al. |
| 2004/0176282 A1 | 9/2004 | Dalby et al. |
| 2004/0235053 A1 | 11/2004 | Lam et al. |
| 2005/0013867 A1 | 1/2005 | Lehrman et al. |
| 2005/0130195 A1 | 6/2005 | Fujihara et al. |
| 2005/0142582 A1 | 6/2005 | Doyle et al. |
| 2005/0227225 A1 | 10/2005 | Krevolin |
| 2005/0288244 A1 | 12/2005 | Manoharan et al. |
| 2006/0014172 A1 | 1/2006 | Muller et al. |
| 2006/0057573 A1 | 3/2006 | Gold et al. |
| 2006/0105341 A1 | 5/2006 | Krause et al. |
| 2006/0142311 A1 | 6/2006 | Okamoto et al. |
| 2006/0188958 A1 | 8/2006 | Fujihara et al. |
| 2007/0003950 A1 | 1/2007 | Shen et al. |
| 2007/0041901 A1 | 2/2007 | Diener et al. |
| 2007/0161015 A1 | 7/2007 | Zheng et al. |
| 2007/0166741 A1 | 7/2007 | Heil et al. |
| 2007/0166742 A1 | 7/2007 | Gold et al. |
| 2009/0004667 A1 | 1/2009 | Zichi et al. |
| 2009/0042206 A1 | 2/2009 | Schneider et al. |
| 2009/0306461 A1 | 12/2009 | Oksenberg et al. |
| 2010/0055695 A1 | 3/2010 | Zichi et al. |
| 2010/0317120 A1 | 12/2010 | Heil et al. |
| 2010/0317723 A1 | 12/2010 | Lee et al. |
| 2011/0082286 A1 | 4/2011 | Zichi |
| 2011/0136099 A1 | 6/2011 | Schneider et al. |
| 2012/0264117 A1 | 10/2012 | Sanders et al. |
| 2014/0058076 A1 | 2/2014 | Rohloff et al. |
| 2014/0249043 A1 | 9/2014 | Schneider et al. |
| 2015/0168388 A1 | 6/2015 | Heil et al. |

FOREIGN PATENT DOCUMENTS

| | | |
|---|---|---|
| CN | 1934255 B | 7/2012 |
| EP | 0310251 | 4/1989 |
| EP | 2172566 | 3/2015 |
| GB | 2 183 661 | 6/1987 |
| JP | Hei 5-500799 A | 2/1993 |
| JP | H08(1996)-511527 A | 12/1996 |
| JP | H11(1999)-506107 A | 12/1996 |
| JP | 2000-327694 A | 11/2000 |
| JP | 2004-238353 A | 8/2004 |
| JP | 2004-307464 | 11/2004 |
| JP | 2005-517456 A | 6/2005 |
| JP | 2005-194257 | 7/2005 |
| RU | 2088588 C1 | 8/1997 |
| WO | WO 1988/09810 | 12/1988 |
| WO | WO 90/15065 | 12/1990 |
| WO | WO 1991/19813 | 12/1991 |
| WO | WO 1992/14842 | 3/1992 |
| WO | WO 1992/14843 | 9/1992 |
| WO | WO 1993/04204 | 3/1993 |
| WO | WO 94/29279 | 12/1994 |
| WO | WO 1995/07364 | 3/1995 |
| WO | WO 1996/038460 | 12/1996 |
| WO | WO 1998/33941 | 8/1998 |
| WO | WO 2001/009159 | 2/2001 |
| WO | WO 2001/061037 | 8/2001 |
| WO | WO 2003/070984 | 8/2003 |
| WO | WO 2004/43996 | 5/2004 |
| WO | WO 2004/047742 | 6/2004 |
| WO | WO 2005/020885 | 3/2005 |
| WO | WO 2005/020972 | 3/2005 |
| WO | WO 2006/063717 | 6/2006 |
| WO | WO 2006/096754 | 9/2006 |
| WO | WO 2008/078180 | 7/2008 |
| WO | WO 2008/137776 | 11/2008 |
| WO | WO 2009/012410 | 1/2009 |
| WO | WO 2009/012420 | 1/2009 |
| WO | WO 2010/129666 | 11/2010 |
| WO | WO 2011/022427 | 2/2011 |
| WO | WO 2011/130195 | 10/2011 |
| WO | WO 2013/185078 | 12/2013 |

OTHER PUBLICATIONS

Bergstrom and Ruth (1976) J. Amer. Chem. Soc. 98(6): 1587-1589, "Synthesis of C-5 substituted pyrimidine nucleosides via organopalladium intermediates".

Bergstrom et al. (1982) J. Org. Chem. 47(11): 2174-2178, "Pyrido[2,3-d]pyrimidine nucleosides. Synthesis via cyclization of C-5-substituted cytidines".

(56) References Cited

OTHER PUBLICATIONS

Bigge and Mertes (1981) J. Org. Chem. 46(10): 1994-1997, "A palladium-catalyzed coupling reaction and a photolytic reaction for the direct synthesis of 5-arylpyrimidine nucleotides".
Bock et al., (1992) Nature 355:564-565 "Selection of Single-Stranded DNA Molecules That Bind and Inhibit Human Thrombin".
Carey et al. (1983) Biochemistry 22:2601-2610 "Sequence Specific Interaction of R17 Coat Protein with Synthetic Variants of Its Ribonucleic Acid Binding Site".
Crisp (1989) Synthetic Communications 19: 2117-2123, "Synthesis of 5-alkenyl-2' deoxyuridines via organostannanes".
Crisp and Flynn (1990) Tetrahedron Letters 31(9):1347-1350, "Palladium-catalysed coupling of uridine triflate with organostannanes".
Crouch and Eaton (1994) Nucleosides & Nucleotides 13(4): 939-944, "Synthesis of 2'deoxyuridine nucleosides with appended 5-position carbonyl cross-linking groups".
Daniels et al. (Dec. 23, 2003) PNAS 100(26):15416-15421, "A tenascin-C aptamer identified by tumor cell SELEX: Systematic evolution of ligands by exponential enrichment".
Davis et al. (Sep. 3, 2002) PNAS, 99(18):11616-11621, "Isolation of high-affinity GTP aptamers from partially structured RNA libraries".
Dewey et al. (1995) J. Am. Chem. Soc. 117: 8474-8475, "New Uridine Derivatives for Systematic Evolution of RNA Ligands by Exponential Enrichment".
DiDonato (2006) Dissertation, University of North Carolina, Raleigh [entire paper].
DiDonato (2006) "Disseration. Part II. Synthesis and Evaluation of Modified Nucleotides for DNA Aptamer Selection" University of North Carolina, Raleigh 30-53.
Dissociation constant, Wikipedia, https://en.wikipedia.org/wiki/Dissociation_constant.
Drabovich et al. (May 1, 2006) Analytical Chemistry 78(9):3171-3178, "Selection of smart aptamers by methods of kinetic capillary electrophoresis".
Eaton et al. (1997) Bioorganic & Medicinal Chemistry 5(6):1087-1096, "Post-SELEX Combinatorial Optimization of Aptamers".
Eaton et al. (1997) Current Opinion in Chemical Biology 1:10-16, "The joys of in vitro selection: chemically dressing oligonucleotides to satiate protein targets".
Ekins and Chu (Sep. 1997) JIFCC 9(3):100-109, "Immunoassay and Other Ligand Assays: Present Status and Future Trends".
Ellington & Szostak (1990) "Selection of RNAs with ligand-specific binding activity from pools of random sequence molecules" RNA Processing meeting abstract, p. 84.
EP Office Action dated Feb. 16, 2011 in European Application Serial No. 08782010.6.
EP Office Action dated Feb. 28, 2011 in European application serial No. 07718147.7.
EP Office Action dated Dec. 18, 2012 in European application serial No. 09012809.1.
EP Search report dated Dec. 1, 2009 in EP application serial No. 08782010.6.
EP Search report dated Feb. 22, 2010 in EP application serial No. 09012809.1.
Extended European Search Report dated Jun. 30, 2015 in EP 15152547.4.
Extended European Search Report dated Oct. 14, 2015 in EP 15158380.4.
Extended European Search Report dated Feb. 5, 2018 in EP 17181688.7.
European Partial Search Report dated Jul. 16, 2012 in EP application serial No. 12160299.9.
European Partial Search Report dated Oct. 24, 2012 in EP application serial No. 12160299.9.
Famulok and Szostak (1992) Angew. Chem. Int. Ed. Engl. 31(8): 979-988, "In Vitro Selection of Specific Ligand-binding Nucleic Acids".
Gebhardt et al. (Jun. 20, 2000) Biochemistry 39(24):7255-7265, "RNA aptamers to S-adenosylhomocysteine: kinetic properties, divalent cation dependency, and comparision with anti-S-adenosylhomocysteine antibody".
Gold et al. (Jan. 1, 1995) Harvey Lectures 91:47-57, "The SELEX Process: A Surprising Source of Therapeutic and Diagnostic Compounds".
Gold et al. (Dec. 7, 2010) PLOS One 5(12):e15004, "Aptamer-Based Multiplexed Proteomic Technology for Biomarker Discovery".
Goodchild et al. (1983) J. Med. Chem. 26(9): 1252-1257, "Structural Requirements of Olefinic 5-Substituted Deoxyuridines for Antiherpes Activity".
Hobbs et al. (1973) Biochemistry 12(25): 5138-5145, "Polynucleotides Containing 2'-Amino-2'-deoxyribose and 2'-Azido-2'deoxyribose".
Holmes et al. (2005) Eur. J. Org. Chem. 5171-5183 "Syntheses and Oligonucleotide Incorporation of Nucleoside Analogues Containing Pendant Imidazolyl or Amino Functionalities—The Search for Sequence-Specific Artificial Ribonucleases".
Holy (1972) Collection Czechoslov. Chem. Commun. 37: 1555-1576, "Nucleic acid components and their analogues. CXLVII. Preparation of 5-ethoxycarbonyluridine, 5-carboxyuridine and their nucleotide derivatives".
Ikehara and Tada (1968) Synthetic Procedures in Nucleic Acid Chemistry (Zorbach and Tipson, eds) 1: 189-193, "2'-Deoxyadenosine and 3'-Deoxyadenosine (Cordycepin)".
Ito et al. (2003) Nucleic Acids Research 31(10):2514-2523, "Synthesis, thermal stability and resistance to enzymatic hydrolysis of the oligonucleotides containing 5-(N-aminohexyl)carbamoyl-2'-O-methylurindines".
IPRP dated Jan. 19, 2010 in PCT/US2008/070383.
ISR and Written Opinion dated Dec. 17, 2008 in PCT/US2008/070383.
Jhaveri et al. (Sep. 8, 1998) Bioorganic & Medicinal Chemistry Letters, 8(17):2285-2290, "In vitro selection of phosphorothiolated aptamers".
Joyce (1989) Gene 82:83-87, "Amplification, mutation and selection of catalytic RNA".
Joyce and Inoue (1989) Nucleic Acids Research 17(2): 711-722, "A novel technique for the rapid preparation of mutant RNAs".
Kacian et al. (Oct. 1972) Proc. Natl. Acad. Sci. USA 69(10):3038-3042, "A Replicating RNA Molecule Suitable for a Detailed Analysis of Extracellular Evolution and Replication".
Kang et al. (May 29, 2007) FEBS Letters, 581(13):2497-2502, "Combinatorial selection of a RNA thioaptamer that binds to Venezuelan equine encephalitis virus capsid protein".
Kawakami et al. (1997) Nucleic Acids Symposium Series No. 37:201-202, "Evolution of a phosphorothioate RNA library during in vitro selection".
Kim et al. (2005) Bioorg. Med. Chem. Lett. 15:77-79, "A new synthetic analogue of thymidine, 7-(3-bromo-phenoxy)-thymidine, inhibits the proliferation of tumor cells".
Kinzler and Vogelstein (1989) Nucleic Acids Research 17(10): 3645-3653, "Whole genome PCR: application to the identification of sequences bound by gene regulatory proteins".
Kramer et al. (1974) J. Mol. Biol. 89: 719-736, "Evolution in vitro: sequence and phenotype of a mutant RNA resistant to ethidium bromide".
Kusser (2000) Reviews in Molecular Biotechnology 74:27-38, "Chemically modified nucleic acid aptamers for in vitro selections: evolving evolution".
Kuwahara et al. (2005) Nucleic Acids Symposium Series 49:81-81, "Screening of a glutamic acid-binding aptamer from arginine-modified DNA library".
Kuwahara et al. (2006) Bioorganic & Medicinal Chemistry 14:2518-2526, Direct PCR amplification of various modified DNAs having amino acids: Convenient preparation of DNA libraries with high-potential activities for in vitro selection.
Langer et al. (Nov. 1981) Proc. Natl. Acad. Sci. USA,78(11):6633-6637, "Enzymatic synthesis of biotin-labeled polynucleotides: Novel nucleic acid affinity probes".
Latham et al. (1994)Nucleic Acids Research 22(14):2817-2822, "The application of a modified nucleotide in aptamer selection: novel thrombin aptamers containing 5-(1-pentynyl)-2'-deoxyuridine".

(56) References Cited

OTHER PUBLICATIONS

Lavitrano et al. (1992) Molecular Reproduction and Development 31:161-169, "The Interaction between Exogenous DNA and Sperm Cells".
Levisohn and Spiegleman (1968) PNAS USA 60: 866-872, "The cloning of a self-replicating RNA molecule".
Levisohn and Spiegleman (1969) PNAS USA 63: 805-811, "Further extracellular Darwinian experiments with replicating RNA moleucles: diverse variants isolated under different selective conditions".
Mamos et al. (1992) Tetrahedron Letters 33(17): 2413-2416, "Straight-forward C-8 alkylation of adenosine analogues with tetraalkyltin reagents".
Martin et al. (1992) J. of Medicinal Chemistry, 35(12):2145-2154, "3D Database Searching in Drug Design".
Masud et al. (2004) Bioorganic & Medicinal Chemistry 12:1111-1120, "Sialyllactose-binding modified DNA aptamer bearing additional functionality by SELEX"005.
Matsuda et al. (1979) Chemical and Pharmaceutical Bulletin, Pharmaceutical Society of Japan, Tokyo, JP 27(1): 183-192, "Nucleosides and nucleotides. XXVII. Synthesis of 2- and 8-cyanoadenosines and their derivatives".
Matthews and Kricka (1988) Analytical Biochemistry 169:1-25, "Analytical Strategies for the Use of DNA Probes".
McGown et al. (Nov. 1995) Anal. Chem. 67:663A-668A, "The Nucleic Acid Ligand. A New Tool for Molecular Recognition".
Milligan et al. (Jul. 1993) J. Medicinal Chemistry, 36(14):1923-1937, "Current Concents in Antisense Drug Design".
Mills et al. (1967) Proc. Natl. Acad. Sci. USA 58:217-224, "An Extracellular Darwinian Experiment with a Self-Duplicating Nucleic Acid Molecule".
Mills et al. (1973) Science 180:916-927, "Complete Nucleotide Sequence of a Replicating RNA Molecule".
Mori et al. (2004) Nucleic Acids Research 32(20):6120-6128, "RNA aptamers selected against the receptor activator of NF-kB acquire general affinity to proteins of the tumor necrosis factor receptor family".
Nomura et al. (1997) Nucleic Acids Research 25(14):2784-2791, "Site-specific introduction of functional groups into phosphodiester oligodeoxynucleotides and their thermal stability and nuclease-resistance properties".
Office Action dated Apr. 27, 2009 in U.S. Appl. No. 11/623,580.
Office Action dated Feb. 22, 2010 in U.S. Appl. No. 11/623,580.
Office Action dated Jun. 25, 2010 in U.S. Appl. No. 12/175,434.
Office Action dated Feb. 23, 2011 in U.S. Appl. No. 12/859,930.
Office Action dated Jan. 24, 2008 in U.S. Appl. No. 11/623,822.
Office Action dated Jun. 24, 2010 in U.S. Appl. No. 12/499,967.
Office Action dated Jun. 9, 2010 in U.S. Appl. No. 12/175,446.
Office Action dated Sep. 11, 2008 in U.S. Appl. No. 11/623,822.
Oliphant and Struhl (1987) Methods in Enzymology 155: 568-582, "The use of random-sequence oligonucleotides for determining consensus sequences".
Oliphant and Struhl (1988) Nucleic Acids Research 16(15): 7673-7683, "Defining the consensus sequences of *E. coli* promoter elements by random selection".
Oliphant et al. (1986) Gene 44:177-183, "Cloning of random-sequence oligodeoxynucleotides".
Oliphant et al. (Jul. 1989) Mol. Cell. Biol. 9: 2944-2949, "Defining the sequence specificity of DNA-binding proteins by selecting binding sites from random-sequence oligonucleotides: analysis of yeast GCN4 protein".
Ono et al. (1994) Bioorg. & Med. Chem. Let. 4(2): 361-366, "Nucleosides and Nucleotides. 127. A novel and convenient post-synthetic modification method for the synthesis of oligodeoxyribonucleotides carrying amino linkers at the 5-position of 2'deoxyuridine".
Osborne et al. (1997) Current Opinion in Chemical Biology 1:5-9, "Aptamers as Therapeutic and Diagnostic Reagents: Problems and Prospects".

Ostendorf (1999) Medizinische Klinik 94(4):219-223 "Aptamere: ein neuer Ansatz für Interventionsstudien und zur Entwicklung zukünftiger Therapieansätze" (with English Abstract).
Perlman et al. (1985) J. Med. Chem. 28(6): 741-748, "Nucleosides. 133. Synthesis of 5-alkenyl-1-(2-deoxy-2-fluoro-β-D-arabinofuranosyl) cytosines and related pyrimidine nucleosides as potential antiviral agents".
Pieken et al. (1991) Science 253:314-317, "Kinetic Characterization of Ribonuclease-Resistant 2'modified Hammerhead Ribozymes".
Pinkel et al. (Dec. 1988) Proc. Natl. Acad. Sci. USA 85:9138-9142, "Fluorescence in situ hybridization with human chromosome-specific libraries: Detection of trisomy 21 and translocations of chromosome 4".
Potyrailo et al. (Aug. 1998) Anal. Chem. 70(16):3419-3425, "Adapting Selected Nucleic Acid Ligands (Aptamers) to Biosensors".
Result of a biacore simulation, BIAsimulation—Basic Kinetics chart.
Robertson and Joyce (Mar. 1990) Nature 344: 467-468, "Selection in vitro of an RNA enzyme that specifically cleaves single-stranded DNA".
Romaniuk et al. (1987) Biochemistry 26(6):1563-1568, "RNA Binding Site of R17 Coat Protein".
Ruth and Bergstrom (1978) J. Org. Chem. 43(14): 2870-2876, "C-5 substituted pyrimidine nucleosides. 1. Synthesis of C-5 allyl, propyl, and propenyl uracil and cytosine nucleosides via organopalladium intermediates".
Saffhill et al. (1970) J. Mol. Biol. 51:531-539, "In Vitro Selection of Bacteriophage Qβ Ribonucleic Acid Variants Resistant to Ethidium Bromide".
Sagi et al. (1994) J. Med. Chem. 37: 1307-1311, "Synthesis and antiviral activities of 8-alkynyl-, 8-alkenyl-, and 8-alkyl-2'-deoxyadenosine analogues".
Saitoh et al. (2002) Nucleic Acids Research Supplement 2:215-216 "Modified DNA aptamers against sweet agent aspartame".
Sakthivel et al. (1998) Angew Chem Int Ed 37(20):2872-2875 "Expanding the Potential of DNA for Binding and Catalysis: Highly Functionalized dUTP Derivatives That are Substrates for Thermostable DNA Polymerases".
Schoetzau et al. (2003) Bioconjugate Chemistry 14:919-926, "Aminomodified Nucleobases: Functionalized Nucleoside Triphosphates Applicable for SELEX".
Sekiya et al. (2005) Nucleic Acids Symposium 49:361-362 In vitro selection of RNA aptamers against cellular and abnormal isoform of mouse prion protein.
Schimmel (Jul. 1989) Cell 58:9-12, "RNA Pseudoknots That Interact with Components of the Translation Apparatus".
Srisawat et al. (2001) Nucleic Acids Research 29(2):1-5 "Sephadex-binding RNA ligands: rapid affinity purification of RNA from complex RNA mixtures".
Stein et al. (Aug. 1993) Science 261:1004-1012, "Antisense Oligonucleotides as Therapeutic Agents—is the Bullet Really Magical?"
Syvanen et al. (1986) Nucleic Acid Research, 14(12):5037-5048, "Fast quantification of nucleic acid hybrids by affinity-based hybrid collection".
Szostak (1988) Redesigning the Molecules of Life, (S.A. Benner ed.) Springer-Verlag Berlin Heidelberg, pp. 87-113.
Tarasow et al. (1997) Nature vol. 398:54-17, "RNA-catalysed carbon-carbon bond formation".
Tarasow (1998) Nucleic Acid Sciences 48(1):29-37.
Thiesen and Bach (Jun. 1990) Nucleic Acids Res. 18(11): 3203-3209, "Target detection assay (TDA): a versatile procedure to determine DNA binding sites as demonstrated on SP1 protein".
Tronchet et al. (1988) Nucleosides and Nucleotides, 7(2): 249-269, "3'-deoxy-3'-hydroxyamino-β-D-xylofuranosyluracil and derivatives thereof".
Tuerk and Gold (Aug. 1990) Science 249: 505-510, "Systematic evolution of ligands by exponential enrichment: RNA ligands to bacteriophage T4 DNA polymerase".
Tuerk et al. (Aug. 1992) Proc. Natl. Acad. Sci. USA 89:6988-6992, "RNA pseudoknots that inhibit human immunodeficiency virus type 1 reverse transcriptase".

(56) References Cited

OTHER PUBLICATIONS

Tuerk et al. (Mar. 1988) Proc. Natl. Acad. Sci. USA 85:1364-1368, "CUUCGG Hairpins: Extraordinarily Stable RNA Secondary Structures Associated with Various Biochemical Processes".
Ueno et al. (1997) Nucleic Acids Research 25(19):3777-3782, "Effects of 5-(N-aminohexyl)carbamoyl-2'-deoxyuridine on endonuclease stability and the ability of oligodeoxynucleotide to activate RNase H".
Uhlenbeck et al. (1983) J. Biomolecular Structure and Dynamics 1:539-552, "Interaction of R17 Coat Protein with its RNA Binding Site for Translational Repression".
Uhlmann and Peyman (Jun. 1990) Chemical Reviews 90(4):544-584, "Antisense Oligonucleotides: A New Therapeutic Principle".
Vaish et al. (2003) Biochemistry 42:8842-8851, "A Novel, Modification-Dependent ATP-Binding Aptamer Selected from an RNA Library Incorporating a Cationic Functionality".
Van Aerschot et al. (1993) J. Med. Chem. 36: 2938-2942, "Antiviral activity of C-alkylated purine nucleosides obtained by cross-coupling with tetraalkyltin reagents".
Vaught et al. (2004) J.Am. Chem. Soc. 126:11231-11237, "T7 RNA Polymerase Transcription and 5-Position Modified UTP Derivatives".
Vaught, Jonathan David Thesis, Oct. 2008, "Enhancing the Functionality of Nucleic Acids".
Witherell and Uhlenbeck (1989) Biochemistry 28:71-76, "Specific RNA Binding by Qβ Coat Protein".
Wochner et al. (2007) Expert Opin. Drug Discov. 2(9):1205-1224 "Characterisation of aptamers for therapeutic studies".
Yarus (1988) Science 240:1751-1758, "A Specific Amino Acid Binding Site Composed of RNA".
You, Qidong et al. (Jan. 31, 2004) Medicinal Chemistry, Chemical Industry Press, pp. 32-34, with Office Action dated Mar. 31, 2016 in Chinese Patent Application No. 201180028946.3 to show relevance.
Zichi et al. (Mar. 7, 2008) Current Opinion in Chemical Biology 12(1):78-85, "Proteomics and diagnostics: Let's Get Specific, again".
Kopylov et al. (2000) Mol. Biol. 34(6):940-954, "Combinatorial Chemistry of Nucleic Acids: SELEX".
Carter et al. (2000) J. Org. Chem. 65(24):8375-8378 "Chemical Evidence for Thiyl Radical Addition to the C6-Position of a Pyrimidine Nucleoside and Its Possible Relevance to DNA Damage Amplification".
CAS RN RN 185849-72-3, CA Index Name: 5'-Cytidylic acid, 2'-deoxy-5-[[[2-(4-hydroxyphenyl)ethyl]amino]carbonyl]-(9CI), STN Entry Date Feb. 6, 1997, 3 pp.

Template 1

5'-ABABGTCTTCTTGTCGTTTCGC-(N)$_{40}$-GGTGGAGTGTGGTGAGG-3'

(SEQ ID NO:1)

Forward PCR Primer 1

5'-ATATATATCCTCACCACACTCCACC-3' (SEQ ID NO:2)

Reverse PCR Primer 1

5'-ABABTTTTTTTGTCTTCTTGTCGTTTCGC-3' (SEQ ID NO:3)

Template 2

5'-ABABCCGTCCTCCTCTCCGTC-(N)$_{40}$-GGGACACTGGGTGCAGG-3'

(SEQ ID NO:4)

Forward PCR Primer 2

5'-ATATATATCCTGCACCCAGTGTCCC-3' (SEQ ID NO:5)

Reverse PCR Primer 2

5'-ABABTTTTTTTCCGTCCTCCTCTCCGTC-3' (SEQ ID NO:6)

(His)$_6$-complement Oligonucleotide

5'-GTCTTCTTGTCGTTTCGC-3' (SEQ ID NO:7)

FIG. 2

Template 1

5'-ABABCCCGCTCGTCGTCTG-(N)$_{40}$-CAGGCAGACGGTCACTC-3'

(SEQ ID NO:8)

Forward BrdU Primer 1

5'-BrdU - ATATATATGAGTGACCGTCTGCCTG-3' (SEQ ID NO:9)

Forward ANA Primer 1

5'- ANA - ATATATATGAGTGACCGTCTGCCTG-3' (SEQ ID NO:10)

Forward AQ Primer 1

5'- AQ - ATATATATGAGTGACCGTCTGCCTG-3' (SEQ ID NO:11

Forward Psor Primer 1

5'- Psor - ATATATATGAGTGACCGTCTGCCTG-3' (SEQ ID NO:12)

Forward PCR Primer 1

5'-ATATATATGAGTGACCGTCTGCCTG-3' (SEQ ID NO:13)

Reverse Primer 1

5'-TTTTTTTTCCCGCTCGTCGTCTG-3' (SEQ ID NO:14)

Reverse PCR Primer 1

5'-ABABTTTTTTTTCCCGCTCGTCGTCTG-3' (SEQ ID NO:15)

FIG. 4A

Template 2

5'-ABABGTGTCTGTCTGTGTCCTC-(N)$_{40}$-GGTGGAGTGTGGTGAGG-3'

(SEQ ID NO:16)

Forward BrdU Primer 2

5'- BrdU - ATATATATCCTCACCACACTCCACC-3'  (SEQ ID NO:17)

Forward ANA Primer 2

5'- ANA - ATATATATCCTCACCACACTCCACC-3'  (SEQ ID NO:18)

Forward AQ Primer 2

5'- AQ - ATATATATCCTCACCACACTCCACC-3'  (SEQ ID NO:19)

Forward Psor Primer 2

5'- Psor - ATATATATCCTCACCACACTCCACC-3'  (SEQ ID NO:20)

Forward PCR Primer 2

5'-ATATATATCCTCACCACACTCCACC-3'  (SEQ ID NO:21)

Reverse Primer 2

5'-TTTTTTTTGTGTCTGTCTGTGTCCTC-3'  (SEQ ID NO:22)

Reverse PCR Primer 2

5'- ABABTTTTTTTGTGTCTGTCTGTGTCCTC-3'  (SEQ ID NO:23)

FIG. 4B

Anthraquinone (AQ)
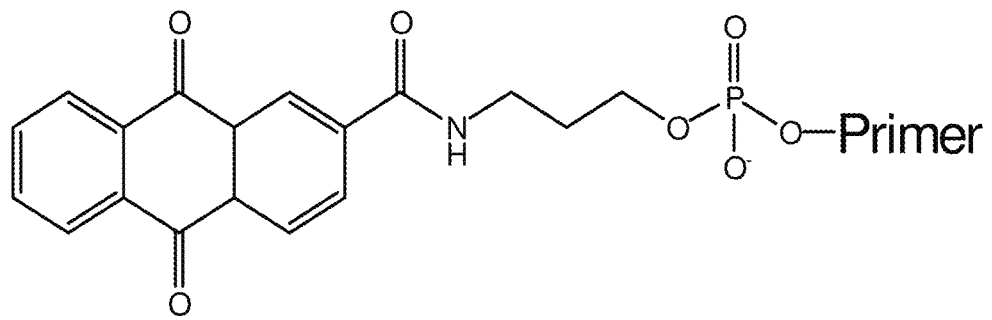
Psoralen (Psor)
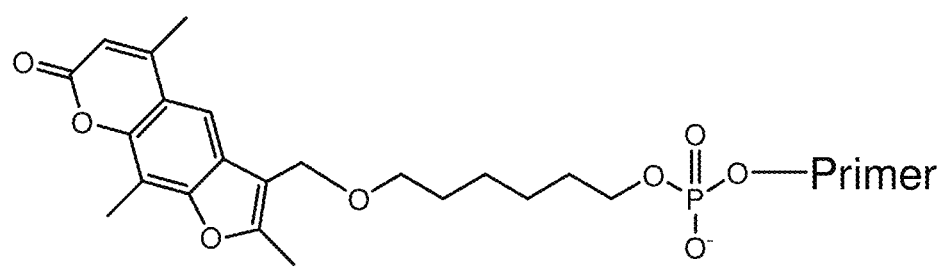
FIG. 5

4-Azido-2-nitro-aniline (ANA)

FIG 7

| | | | |
|---|---|---|---|
| 4-1BB | Apo E4 | BMP RII | Cathepsin D |
| 4-1BB ligand | APRIL | β-NGF | Cathepsin G |
| 6Ckine | AREG | Bone proteoglycan II | Cathepsin S |
| α-1-Antichymotrypsin | ARGI1 | BPI | Cathepsin V |
| α-2-Antichymotrypsin | ARSB | C1q | CCL28 |
| ACE2 | ART | C1r | CD5L |
| Activated Protein C | Artemin | C2 | CD22 |
| Activin A | ASAH2 | C3 | CD23 |
| Activin R1A | ASAHL | C3a | CD30 |
| Activin R1B | ATS1 | C3adesArg | CD30 Ligand |
| ADAMTS – 4 | ATS13 | C3b | CD36 ANTIGEN |
| ASAMTS – 5 | Aurora kinase A | C3d | CD39 |
| Aggrecan | Azurocidin | C4 | CD97 |
| AIF1 | B7 | C4b | CD109 |
| ALCAM | B7-2 | C5 | Ceruloplasmin |
| ALK-1 | BAFF | C5a | CFC1 |
| Alkaline phosphatase, bone | BCAM | C5b, 6 Complex | Chk1 |
| AMPM2 | β-Catenin | C6 | Ck-β-8-1 |
| Amyloid precursor protein | Bcl-2 | C7 | CK-BB |
| Angiogenin | BCMA | C8 | CK-MM |
| Angiopoietin -1 | BDNF | C9 | CLF-1/CLC Complex |
| Angiopoietin – 2 | β-Endorphin | Cadherin E | CMP-Sialic Acid Synthetase |
| Angiopoietin – 4 | bFGF | Cadherin-5 | CNTF |
| ANGL3 | bFGF-R | Calcineurin B α | CNTFR alpha |
| ANGL4 | BGH3 | Calpain I | CNTN2 |
| Apo A -1 | β-Glucosidase | Calpastatin | Coagulation Factor α-XIIa |
| Apo B | BGN | Carbonic Anhydrase IV | Coagulation Factor IX |
| Apo E | BLC | Cardiotrophin – 1 | Coagulation Factor IXab |
| Apo E2 | BMP-7 | Caspase-3 (pro) | Coagulation Factor V |
| Apo E3 | BMP-14 | Catalase | Coagulation Factor VII |
| | BMPER | Cathepsin A | Coagulation Factor X |
| | BMPR1A | Cathepsin B | Coagulation Factor Xa |

FIG. 7 CONT'D

| | | | |
|---|---|---|---|
| Coagulation Factor XI | DLL4 | FCG2A | GDF -9 |
| Coagulation Factor XIa | Dopa decarboxylase | FCG2B | GDF -11 |
| Coagulation Factor XIII | DRG -1 | FCG3B | GDNF |
| Collagen Type I | DRR1 | FCGR1 | GFAP |
| COLEC 12 | Dtk | Ferritin | GFRα -1 |
| COMMD7 | EDA (A2) | FGF -4 | GFRα -2 |
| Contactin -1 | EDAR | FGF -5 | GFRα -3 |
| Contactin -4 | EG – VEGF | FGF -6 | GIB |
| COX -2 | eIF -5 | FGF -7 | GIIE |
| Cripto | Elastase | FGF -8B | GITR |
| CRIS3 | EMAP -2 | FGF -9 | Glucocorticoid receptor |
| CRP | ENA -78 | FGF -10 | Glutamate carboxypeptidase |
| CTACK | Endostatin | FGF -16 | Glutathione S-transferase Pi |
| CTGF | Eotaxin | FGF -17 | Glypican 3 |
| | Eotaxin -2 | FGF -18 | gp130, soluble |
| CTLA -4 | Eotaxin -3 | FGF -19 | GPC2 |
| CXCL 16, soluble | Ephrin –A4 | FGF -20 | GPVI |
| Cystatin C | Ephrin –A5 | FGFR -2 | Granulysin |
| Cystatin M | Ephrin – B3 | Fibrinogen | Granzyme B |
| CYTD | Ephithelial cell kinase | Fibronectin | Gro - α |
| CYTF | EPO – R | Flt -3 | Gro - γ |
| CYTN | ER | Flt -3 ligand | Growth hormone receptor |
| Cytochrome C | ERBB1 | Fractalkine/CX3CL -1 | GSK – 3 beta |
| Cytochrome P450 3A4 | ERBB2 | FSH | GV |
| DAN | ERBB3 | FST | GX |
| DARPP-32 | ERBB4 | FYN | HAI -1 |
| DC - SIGN | ERK – 1 | GA733 -1 protein | Haptoglobin, Mixed type |
| DC – SIGNR | ESAM | Galectin -2 | Hat 1 |
| D – dimer | Factor B | Galectin -3 | HB –EGF |
| DEAD – box protein 19B | Factor D | Galectin -4 | HCC -1 |
| Desmoglein -1 | Factor H | Galectin -7 | HCC -4 |
| DKK1 | Factor I | GAS1 | HDAC8 |
| | Fas ligand, soluble | GASP -2 | Hemopexin |
| | Fas, soluble | G-CSF-R | |

FIG. 7 CONT'D

| | | | |
|---|---|---|---|
| Heparin cofactor II | IGFBP -4 | IL – 17 sR | Layilin |
| HGF | IGFBP -5 | IL – 17B | LBP |
| Histone H 1.2 | IGFBP -6 | IL – 17D | LD78-beta |
| HIV -2 Rev | IGFBP -7 | IL – 17E | Leptin |
| HMG -1 | IGF – I | IL – 17F | Lipocalin 2 |
| HO -2 | IGF – I sR | IL – 18 Bpa | LKHA4 |
| HPLN1 | IGF – II receptor | IL – 18 Rα | LRIG3 |
| HPV E7 Type16 | IgM | IL – 18 Rβ | LRP8 |
| HPV E7 Type18 | IL - 1β | IL – 19 | LSAMP |
| HSP 60 | IL – I R AcP | IL – 20 | Luteinizing hormone |
| HSP 70 | IL – 1 R4 | IL – 21 sR | LY86 |
| HSP 90α | IL – 1 sRI | IL – 22 | LY9 |
| HSP 90β | IL - 1F7 | IL – 27 | Lymphotactin |
| HTRA2 | IL – 1Rrp2 | Inosine triphophatase | Lymphotoxin β R |
| HVEM | IL – 2 | IP -10 | Lsozyme |
| I11RA | IL – 2 sRγ | IR | LYVE 1 |
| I12R2 | IL – 4 | I – TAC | Macrophage mannose receptor |
| I-309 | IL – 4 sR | JAM – B | MAPK14 |
| IC3b | IL – 6 | JAM – C | MATN2 |
| ICOS | IL – 6 sRγ | Kallikrein 4 | MATN3 |
| IDE | IL – 7 | Kallikrein 5 | MBL |
| IDS | IL – 7 R alpha | Kallikrein 8 | MCP -1 |
| IDUA | IL – 8 | Kallikrein 11 | MCP -2 |
| IFN -γ | IL – 10 | Kallikrein 12 | MCP -3 |
| IFN -γ R1 | IL – 10 Rβ | Kallikrein 13 | MCP -4 |
| IFN – lambda 1 | IL – 11 | Karyopherin - α2 | M-CSF R |
| IFN – lambda 2 | IL – 12 | Kininogen, HMW, Single Chain | MDC |
| IgE | IL – 12Rβ1 | Kininogen, HMW, Two Chain | MEK1 |
| IGFBP-1 | IL – 13 | KLH | MEPE |
| IGFBP -2 | IL – 13 Rα1 | KREM2 | MER |
| IGFBP -3 | IL – 13 Rα2 | Ku70 | Met |
| | IL – 15 Rα | Lactoferrin | METAP1 |
| | IL – 16 | LAG -1 | MIA |
| | | Laminin | MICA |

FIG. 7 CONT'D

| | | | |
|---|---|---|---|
| Midkine | NG36 | PKC-α | SAP |
| Mif4gd, Mouse | Nidogen | PKC-β-II | SARP-2 |
| MIG | NKG2D | PKC-D | sCD14 |
| Miox, Rat | NKp30 | PKC-ζ | SCF sR |
| MIP -1α | NKp44 | Plasmin | SCGF - α |
| MIP -1β | Noggin | Plasminogen | SCGF - β |
| MIP - 3α | Nogo Receptor | PIGF | Semaphorin 3A |
| MIP -3β | NovH | Prekallikrein | sE-Selectin |
| MK01 | NPS -- PLA2 | PRL | SET9 |
| MMP -1 | NRP1 | Properdin | sFRP-3 |
| MMP -2 | OLR1 | Prostatic acid phosphatase | sICAM-2 |
| MMP -3 | ON | Protease nexin I | sICAM-3 |
| MMP -7 | OPG | Protein C | SIGIR R |
| MMP -8 | OSM | Protein S | Siglec-6 |
| MMP -9 | OX40 Ligand | Prothrombin | Siglec -7 |
| MMP -13 | PAFAH beta subunit | PSA | Siglex -9 |
| MMP -14 | PAI -1 | PSA-ACT | SLAMF8 |
| MMP -17 | PAPP -- A | P-Selectin | sLeptin R |
| MOZ | PARC | PSMA | SLPI |
| MP 112 | Partner protein A | PTHrP | sL-Selectin |
| MPIF -1 | Partner protein B | PTN | SMAC |
| MSP R | P --Cadherin | PTP-1 B | sn-1,2-Diacylglycerol Kinase |
| Myeloperoxidase | PCNA | Rab GDP dissociation factor β | SOD |
| Myosin regulatory light chain 2 | PDGF Rb | Rac1 | Soggy -- 1 |
| NADPH -- P450 Oxidoreductase | PDGF --AA | RAD51 | Sonic Hedgehog |
| NANOG | PD-L2 | RANTES | SPIN T2 |
| NAP -2 | PDPK1 | RAP | Spondin -1 |
| NCAM --L1 | PECAM-1 | RELT | sRage |
| NET4 | Persephin | Resistin | sRANKL |
| NEUREGULIN -1 | PF-4 | RET | sTie-1 |
| Neurotrophin -3 | PGRP-S | RGMB | sTie-2 |
| Neurotrophin -5 | PIGR | RGM-C | sTREM-1 |
| | PKB | S100A4 | STX1α |

FIG. 7 CONT'D

| | | | |
|---|---|---|---|
| Sulotransferase, Nod Factor | Thrombin | TRAIL R4 | ULBP-2 |
| SuPar | Thyroxine-Binding Globulin | Transferrin | ULBP-3 |
| TACI | TIG2 | TrATPase | uPA |
| TARC | TIMP-1 | TrkB | URB |
| tau | TIMP-2 | TrkC | VCAM-1 |
| TBP | TIMP-3 | Troponin I | VEGF |
| TECK | TNF sR-1 | Troponin T | VEGF sR2 |
| Tenascin | TNF sR-II | Trypsin | VEGF sR3 |
| Testican -2 | TNFSF 15 | Trypsin 2 | Vitronection |
| TF | TNFSF 18 | TSLP | vWF |
| TFPI | Tom34 | TSLP R | WFKN2 |
| TGF -β1 | Topoisomerase | TSP2 | WIF-1 |
| TGF -β2 | tPA | TSP4 | WISP-3 |
| TGF -β RIII | Tpo | TWEAK | XEDAR |
| | TRAIL | UBC9 | Yes |
| | TRAIL R2 | Ubiquitin +1 | |
| | | ULBP-1 | |

PCB-sp-cy
Molecular Weight: 1729.78

Molecular Weight: 1784.71
GdmB-P-sp-cy

FIG. 10

A      5' - CY3 – APTAMER – 3'

B      5' - $(AB)_2$ – $(T)_8$ – PC - PRIMER – 3'

C      5' - ANA – PC – CY3 – APTAMER – 3'

D      5' - $(AB)_2$ – $(T)_8$ – PRIMER – 3'

*Denotes point of attachment of the R group to (CH$_2$)$_n$

METHOD FOR GENERATING APTAMERS WITH IMPROVED OFF-RATES

RELATED APPLICATIONS

This application is a continuation of U.S. application Ser. No. 15/878,161, filed Jan. 23, 2018, which is a continuation of U.S. application Ser. No. 15/410,414, filed Jan. 19, 2017, now abandoned, which is a continuation of U.S. application Ser. No. 14/610,758, filed Jan. 30, 2015, now abandoned, which is a continuation of U.S. application Ser. No. 13/113,261, filed May 23, 2011, which issued as U.S. Pat. No. 8,975,388 on Mar. 10, 2015, which is a divisional of U.S. application Ser. No. 12/175,434, filed Jul. 17, 2008, which issued as U.S. Pat. No. 7,947,447 on May 24, 2011, which claims the benefit of U.S. Provisional Application Ser. No. 60/950,281, filed Jul. 17, 2007, U.S. Provisional Application Ser. No. 60/950,293, filed Jul. 17, 2007, U.S. Provisional Application Ser. No. 60/950,283, filed Jul. 17, 2007, U.S. Provisional Application Ser. No. 61/031,420, filed Feb. 26, 2008 and U.S. Provisional Application Ser. No. 61/051,594, filed May 8, 2008. U.S. application Ser. No. 12/175,434 is also a continuation in part of U.S. application Ser. No. 11/623,580 and U.S. application Ser. No. 11/623,535, each of which was filed on Jan. 16, 2007, and each of which are now abandoned. Each of these applications are incorporated herein by reference in their entirety.

FIELD OF THE INVENTION

The present disclosure relates generally to methods for the generation of aptamers and photoaptamers having improved properties and the improved aptamers and photoaptamers generated thereby. In particular, the present disclosure describes slow off-rate aptamers that are highly specific to a target of interest. The disclosure describes the composition of these slow off-rate aptamers as well methods for their selection. Further the disclosure describes aptamer constructs with improved functionalities for detection methods. Further, the disclosure describes applications enabled by these improved aptamers.

SEQUENCE LISTING

Incorporated by reference herein in its entirety is the Sequence Listing entitled "sml_19D_sequence_ST25.txt", created Jul. 28, 2018, size of 6 kilobytes.

BACKGROUND

The following description provides a summary of information relevant to the present disclosure and is not a concession that any of the information provided or publications referenced herein is prior art to the claimed invention.

The SELEX process is a method for the in vitro selection of nucleic acid molecules that are able to bind with high specificity to target molecules and is described in U.S. Pat. No. 5,475,096 entitled "Nucleic Acid Ligands" and U.S. Pat. No. 5,270,163 (see also WO 91/19813) entitled "Nucleic Acid Ligands" each of which is specifically incorporated by reference herein. These patents, collectively referred to herein as the SELEX Patents, describe methods for making an aptamer to any desired target molecule.

The basic SELEX process has been modified to achieve a number of specific objectives. For example, U.S. Pat. No. 5,707,796, entitled "Method for Selecting Nucleic Acids on the Basis of Structure" describes the use of the SELEX process in conjunction with gel electrophoresis to select nucleic acid molecules with specific structural characteristics, such as bent DNA. U.S. Pat. No. 5,580,737, entitled "High-Affinity Nucleic Acid Ligands That Discriminate Between Theophylline and Caffeine" describes a method for identifying highly specific aptamers able to discriminate between closely related molecules, termed Counter-SELEX. U.S. Pat. No. 5,567,588, entitled "Systematic Evolution of Ligands by Exponential Enrichment: Solution SELEX" describes a SELEX-based method which achieves highly efficient partitioning between oligonucleotides having high and low affinity for a target molecule. U.S. Pat. No. 5,496,938, entitled "Nucleic Acid Ligands to HIV-RT and HIV-1 Rev" describes methods for obtaining improved aptamers after SELEX has been performed. U.S. Pat. No. 5,705,337, entitled "Systematic Evolution of Ligands by Exponential Enrichment: Chemi-SELEX" describes methods for covalently linking an aptamer to its target.

The SELEX process encompasses the identification of high-affinity aptamers containing modified nucleotides conferring improved characteristics on the ligand, such as improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides" that describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe).

Further modifications of the SELEX process are described in U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". These patents, collectively referred to herein as "the PhotoSELEX Patents" describe various SELEX methods for selecting aptamers containing photoreactive functional groups capable of binding and/or photocrosslinking to and/or photoinactivating a target molecule. The resulting photoreactive aptamers are referred to as photocrosslinking aptamers or photoaptamers.

Although these SELEX and photoSELEX processes are useful, there is always a need for processes that lead to improved properties of aptamers generated from in vitro selection techniques. For example, a need exists for aptamers to target molecules with better binding affinities than those achieved with naturally occurring DNA or RNA nucleotides, as well as methods for producing such aptamers. For many applications, such as for example, in vitro assays, diagnostics, therapeutic, or imaging applications, it is of interest to produce aptamers with slow dissociation rates from the aptamer/target affinity complex. Several techniques have been proposed for producing such reagents (see, e.g., WO 99/27133 and US 2005/0003362). However, these selection processes do not discriminate between the selection of reagents that have fast association kinetics with the target (i.e., fast on-rates) and the selection of reagents that have slow dissociation kinetics with the target (i.e., slow off-rates). Thus, there is a need for novel processes and techniques that favor the selection of slow off-rate aptamers while inhibiting the selection of aptamers that simply have a fast association rate with the target.

Finally, there is a need for aptamer constructs that include different built-in functionalities. These functionalities may include tags for immobilization, labels for detection, means to promote or control separation, etc.

SUMMARY

The present disclosure describes novel aptamers, and methods to produce and use such aptamers. In particular, the disclosure describes slow off-rate (slow rate of dissociation) aptamers, slow off-rate aptamers containing C-5 modified pyrimidines, and processes for the selection of slow off-rate aptamers by dilution, by the addition of a competitor, or by a combination of both approaches. In addition, slow off-rate aptamers to various targets such as proteins and peptides are described. Slow off-rate aptamers with unique structural features and melting temperatures are also described. The disclosure also describes slow off-rate aptamers with photoreactive functional groups, aptamers that are refractory to the presence of poly-anionic materials, and a selection process for these aptamers, as well as aptamers constructed with a variety of other functionalities to improve their utility in various applications.

The present disclosure describes improved SELEX methods for generating aptamers that are capable of binding to target molecules. More specifically, the present disclosure describes methods for producing aptamers and/or photoaptamers having slower rates of dissociation from their respective target molecules than aptamers and photoaptamers obtained with previous SELEX methods. Generally, after contacting the candidate mixture with the target molecule and allowing the formation of nucleic acid-target complexes to occur, a slow off-rate enrichment process is introduced wherein nucleic acid-target complexes with fast dissociation rates will dissociate and not reform, while complexes with slow dissociation rates will remain intact. Methods for introducing a slow off-rate enrichment process include, but are not limited to, adding competitor molecules to the mixture of nucleic acids and target molecules, diluting the mixture of nucleic acids and target molecules, or a combination of both of these. The disclosure further describes aptamers and photoaptamers obtained using these methods.

In one embodiment, the method comprises preparing a candidate mixture of nucleic acids; contacting the candidate mixture with a target molecule wherein nucleic acids with the highest relative affinities to the target molecule preferentially bind the target molecule, forming nucleic acid-target molecule complexes; introducing a slow off-rate enrichment process to induce the dissociation of nucleic acid-target molecule complexes with relatively fast dissociation rates; partitioning the remaining bound nucleic acid-target molecule complexes from free nucleic acids in the candidate mixture; and identifying the nucleic acids that were bound to the target molecule. The process may further include the iterative step of amplifying the nucleic acids that bind to the target molecule to yield a mixture of nucleic acids enriched with nucleic acids that bind to the target molecule yet produce nucleic acid-target molecule complexes having slow dissociation rates.

In another embodiment, the candidate mixture of nucleic acids includes nucleic acids containing modified nucleotide bases that may aid in the formation of modified nucleic acid-target complexes having slow dissociation rates. Improved methods for performing SELEX with modified nucleotides, including nucleotides which contain photoactive or other functional groups, or nucleotides which contain placeholders for photoactive groups are disclosed in U.S. application Ser. No. 12/175,388, filed Jul. 17, 2008, which is incorporated by reference herein in its entirety, and entitled "Improved SELEX and PHOTOSELEX" which is being filed concurrently with the instant application. Placeholder nucleotides may also be used for the mid-SELEX or post-SELEX introduction of modified nucleotides that are not photoreactive.

The various methods and steps described herein can be used to generate an aptamer capable of either (1) binding to a target molecule or (2) binding to a target molecule and subsequently forming a covalent linkage with the target molecule upon irradiation with light in the UV or visible spectrum.

In another aspect, the various methods and steps described herein can be used to generate an aptamer capable of modifying the bioactivity of a target molecule through binding and/or crosslinking to the target molecule. In one embodiment, an aptamer to a unique target molecule associated with or relevant to a specific disease process is identified. This aptamer can be used as a diagnostic reagent, either in vitro or in vivo. In another embodiment, an aptamer to a target molecule associated with a disease state may be administered to an individual and used to treat the disease in vivo. The aptamers and photoaptamers identified herein can be used in any diagnostic, imaging, high throughput screening or target validation techniques or procedures or assays for which aptamers, oligonucleotides, antibodies and ligands, without limitation can be used. For example, aptamers and photoaptamers identified herein can be used according to the methods described in detail in the concurrently filed U.S. application Ser. No. 12/175,446, entitled "Multiplexed Analyses of Test Samples", which is incorporated by reference herein in its entirety.

Previous aptamers that do not have the slow off-rate properties of the aptamers of the present invention have been used for a variety of purposes. In almost all such uses, slow off-rate aptamers will have improved performance relative to aptamers not selected to have slow off-rate properties.

The aptamer Macugen®, (See, e.g., U.S. Pat. Nos. 6,168,778; 6,051,698; 6,426,335; and 6,962,784; each of which is incorporated herein by reference in its entirety) has been approved for the treatment of macular degeneration, and functions due to its specific affinity for VEGF. Other aptamers have been studied and/or are in development for use as therapeutic agents. Aptamers not selected to have slow off-rate properties have also been used in many diagnostic and imaging applications (See, e.g., U.S. Pat. Nos. 5,843,653; 5,789,163; 5,853,984; 5,874,218; 6,261,783; 5,989,823; 6,177,555; 6,531,286; each of which is incorporated herein by reference in its entirety), high-thorough put screening (See, e.g., U.S. Pat. Nos. 6,329,145; 6,670,132; 7,258,980; each of which is incorporated herein by reference in its entirety) and in PCR kits (See, e.g., U.S. Pat. Nos. 6,183,967; 6,020,130; 5,763,173; 5,874,557; 5,693,502; each of which is incorporated herein by reference in its entirety.) The slow off-rate aptamers of this disclosure may be used in any diagnostic, therapeutic, imaging or any other use for which antibodies, aptamers and ligand binding pairs have been used.

In another aspect, the disclosure provides aptamers and photoaptamers identified by the improved methods disclosed herein, diagnostic kits that include such aptamers and photoaptamers, and therapeutic and diagnostic uses of such aptamers and photoaptamers. The novel, slow off-rate aptamers and photoaptamers identified using the described methods can be used in a variety of assays including, assays that use planar arrays, beads, and other types of solid supports. The assays may be used in a variety of contexts including in life science research applications, clinical diagnostic applications, (e.g., a diagnostic test for a disease, or a "wellness" test for preventative healthcare); ALONA and UPS assays, and in vivo imaging applications. For some applications, multiplexed assays employing the described aptamers and photoaptamers may be used.

In some embodiments, the slow off-rate aptamers (or photoaptamers) described herein can be used as intravenous or oral contrast agents for CAT scans and other imaging applications. CAT scans are used in the diagnosis of muscle and bone disorders, locating blood clots, detecting internal bleeding, monitoring diseases such as cancer, etc. The slow off-rate aptamers may be labeled with a CAT scan detectable component, such as, for example, iodine, barium, or gastrograffin. In addition to carrying the detectable component, the aptamer may be designed to direct that component to a specific tissue or desired target. The aptamer may serve to concentrate or localize the detectable component and thus improve the signal to noise ratio by increasing available signal. Because the off-rate of the aptamer can be sufficiently slow, the duration of the scan can be increased, and the signal to noise ratio of the scan may be improved. The specificity of the aptamer for the target may also improve the signal to noise ratio in these imaging applications.

In one embodiment, the slow off-rate aptamer is labeled with a diamagnetic or paramagnetic material. In this embodiment, the labeled aptamer may be used to improve the performance of magnetic resonance imaging (MRI). MRI is particularly well suited to the imaging of small, selective areas and tissues with high water content or to monitoring blood flow. The specificity of the slow off-rate aptamers may improve the localization of the MRI reagent to a desired tissue section. Similarly, slow off-rate aptamers may be modified with materials such as fluorine, carbon11, oxygen15, or nitrogen13, for use in PET scans. In another embodiment, the aptamers may be labeled with IR active materials that may be used for infrared imaging. It is also contemplated that slow off-rate aptamers may be labeled for use with other imaging modalities.

In one embodiment, the slow off-rate aptamers may be used as very sensitive and specific reagents for incorporation into a variety of in vitro diagnostic methods or kits. In some embodiments, the slow off-rate aptamers are used as substitutes for antibodies in a number of infectious, or other type of, disease detection methods where the aptamer to the target of interest includes either or both a detectable material and an immobilization or capture component. In these embodiments, after the aptamer from the kit is mixed with a clinical specimen, a variety of assay formats may be utilized. In one embodiment, the aptamer also includes a detectable label, such as a fluorophore. In other embodiments, the assay format may include fluorescence quenching, hybridization methods, flow cytometry, mass spectroscopy, inhibition or competition methods, enzyme linked oligonucleotide assays, SPR, evanescent wave methods, etc. In some embodiments, the aptamer is provided in the kit in solution. In other embodiments, the aptamer in the kit is immobilized onto a solid support used in conjunction with the assay for testing the specimen. In various embodiments, the solid support is designed for the detection of one or more targets of interest. In other embodiments, the kit may further include reagents to extract the target of interest, reagents for amplifying the aptamer, reagents for performing washing, detection reagents, etc.

In another embodiment, the slow off-rate aptamers may be used in therapeutic imaging studies. During the development of new therapeutic compounds, it is often difficult to assess certain characteristics of the compound, such as, for example, biodistribution, the washout rate, bioavailability, in vivo drug/target interactions, etc. In many cases, if a suitable detectable material was used to modify the therapeutic compound, imaging studies could be used to assess all of these characteristics. Though direct modification of a therapeutic compound frequently inhibits its ability to interact with its target and thus reduces efficacy, an aptamer's small size and customizable specificity, render it potentially well-suited to react with a therapeutic compound (for example, an antibody or other protein-based therapeutic) while minimizing any undesirable effects on the compound's therapeutic efficacy. To assess such characteristics as biodistribution and the washout rate, the aptamer/therapeutic complex may survive for an extended period of time. These types of studies may be simplified in cases where the therapeutic compound is a slow off-rate aptamer. In various embodiments, aptamers used in therapeutic, imaging, and diagnostic applications may include various modifications, such as, for example, 2' fluoro and other modifications, to increase the stability of the aptamer upon exposure to various components that may be present in a test sample or in vivo, such as, for example, nucleases and other sample or bodily fluid components.

BRIEF DESCRIPTION OF THE FIGURES

FIG. 2 illustrates representative aptamer template, primer, and complementary oligonucleotide sequences used in the disclosure. The oligonucleotides were prepared by standard solid-phase synthesis techniques. B=dT-biotin.

FIGS. 4A and B show oligonucleotides that were used to prepare the candidate mixtures or perform various steps in the selection process described in Example 2. The oligonucleotides were prepared by standard solid-phase synthesis techniques. BrdU (5-bromo-dUTP), Anthraquinone (AQ), and psoralen (Psor) chromophores were purchased as phosphoramidites and added to the 5' terminus of the forward primer during synthesis. 4-azido-2-nitro-aniline (ANA) was prepared as a para-nitro-phenyl carbonate derivative and coupled to a 5' hexylamine phosphoramidite after synthesis. Two candidate mixture sequences were used in this example, designated 1 and 2. B=dT-biotin. (FIG. 4A) Template 1 was only used with candidate mixtures containing 5'-BrdU, AQ, and ANA, and (FIG. 4B) Template 2 was only used with candidate mixtures containing 5'-Psor for Example 2.

FIG. 7 is a chart of over 500 targets for which aptamers have been identified. Many of these aptamers have been designed to have slow dissociation rates from their respective targets.

FIG. 10 illustrates the aptamer and primer constructs described in the disclosure. Cy3 represents a Cyanine 3 dye, PC a photocleavable linker, ANA a photoreactive crosslinking group, $(AB)_2$ a pair of biotin residues separated by dA residues, and $(T)_8$ a poly dT linker. Primer constructs are complementary to the complete 3' fixed region of the aptamer constructs.

DETAILED DESCRIPTION

Figure 1A:
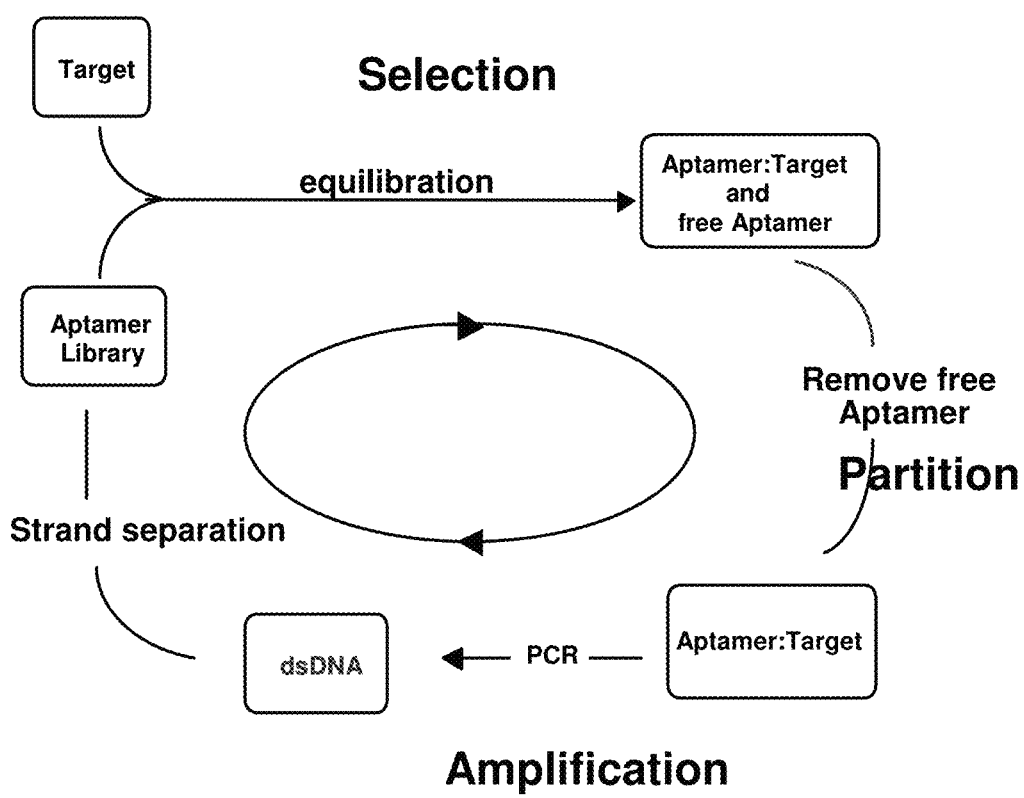
FIG. 1A illustrates an exemplary SELEX method and FIG. 1B illustrates an exemplary SELEX method which includes the step of incorporating a slow off-rate enrichment process or process.

The practice of the invention disclosed herein employs, unless otherwise indicated, conventional methods of chemistry, microbiology, molecular biology, and recombinant DNA techniques within the level of skill in the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition).

All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

As used in this specification, including the appended claims, the singular forms "a," "an," and "the" include plural references, unless the content clearly dictates otherwise, and are used interchangeably with "at least one" and "one or more." Thus, reference to "an aptamer" includes mixtures of aptamers, reference to "a probe" includes mixtures of probes, and the like.

As used herein, the term "about" represents an insignificant modification or variation of the numerical values such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, "nucleic acid ligand" "aptamer" and "clone" are used interchangeably to refer to a non-naturally occurring nucleic acid that has or may have a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure, other than a polynucleotide, that binds to the aptamer through a mechanism which is predominantly independent of Watson/Crick base pairing or triple helix binding, wherein the aptamer is not a nucleic acid having the known physiological function of being bound by the target molecule. Aptamers include nucleic acids that are identified from a candidate mixture of nucleic acids, the aptamer being a ligand of a given target, by the method comprising: (a) contacting the candidate mixture with the target, wherein nucleic acids having an increased affinity to the target relative to other nucleic acids in the candidate mixture may be partitioned from the remainder of the candidate mixture; (b) partitioning the increased affinity and/or slow off-rate nucleic acids from the remainder of the candidate mixture; and (c) amplifying the increased affinity, slow off-rate nucleic acids to yield a ligand-enriched mixture of nucleic acids, whereby aptamers to the target molecule are identified. It is recognized that affinity interactions are a matter of degree; however, in this context, the "specific binding affinity" of an aptamer for its target means that the aptamer binds to its target generally with a much higher degree of affinity than it may binds to other, non-target, components in a mixture or sample. An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers may have either the same number or a different number of nucleotides. Aptamers may be DNA or RNA and maybe single stranded, double stranded, or contain double stranded regions.

As used herein, "slow off-rate" or "slow rate of dissociation" or "slow dissociation rate" refers to the time it takes for an aptamers/target complex to begin to dissociate. This can be expressed as a half life, $t_{1/2}$, or the point at which 50% of the aptamer/target complex has dissociated. The off-rate or dissociation rate of a slow off-rate aptamer, expressed as $t_{1/2}$ values, can be about ≥30 min., ≥about 60 min., ≥about 90 min., ≥about 120 min. ≥about 150 min. ≥about 180 min. ≥about 210 min., and ≥about 240 min.

In one embodiment, a method for producing a synthetic library of nucleic acids comprises: 1) synthesizing the nucleic acids; 2) deprotecting the nucleic acids; 3) purifying the nucleic acids; and 4) analyzing the nucleic acids. In the synthesis step, a monomer mixture is prepared where the ratio of the various nucleotides in the mix is optimized to yield equal ratios of each nucleotide in the final product. One or more of the monomers in the mixture may comprise a modified nucleotide. Amidite protection groups are used in this procedure and in one embodiment, the monomer concentration is 0.1M. During synthesis, the five prime protecting group is retained in the product nucleic acid. Synthesis is conducted on a solid support (controlled pore glass, CPG) and at least about 80 cycles are completed to synthesize the final product.

After the synthesis process, the nucleic acid product is deprotected. A 1.0 M aqueous lysine buffer, pH 9.0 is employed to cleave apurinic sites while the product is retained on the support (controlled pore glass, CPG). These cleaved truncated sequences are washed away with deionized (dI) water two times. 500 uL of dI water are added after the two washes in preparation for the deprotection step. This step involves the treatment with 1.0 mL of t-butylamine:methanol:water, 1:1:2, for 5 hours at 70° C., is followed by freezing, filtration, and evaporation to dryness. The nucleic acid product is purified based on the hydrophobicity of the protecting group on a PRP-3 HPLC column (Hamilton). Appropriate column fractions are collected and pooled, desalted, and evaporated to dryness to remove the volatile elution buffers. The final product is washed with water by a centrifugation process and then re-suspended. Finally the resuspended material is treated to deprotect the final product. Final product is characterized by base composition, primer extension, and sequencing gel.

A candidate mixture of nucleic acids, or a library of nucleic acids, may also be produced by an enzymatic method using a solid phase. In one embodiment, this method comprises the same basic steps described above. In this case the goal is the synthesis of an antisense library and these libraries are produced with a 5' biotin modification. All remaining synthetic processes are as described above. Once the synthetic library is prepared, the nucleic acids may be used in a primer extension mix containing one or more modified nucleotides to produce the final candidate mixture in a classic primer extension method.

Aptamers may be synthesized by the same chemistry that is used for the synthesis of a library. However, instead of a mixture of nucleotides, one nucleotide is introduced at each step in the synthesis to control the final sequence generated by routine methods. Modified nucleotides may be introduced into the synthesis process at the desired positions in the sequence. Other functionalities may be introduced as desired using known chemical modifications of nucleotides.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. Modified nucleotides, such as nucleotides with photoreactive groups or other modifications, can be incorporated into the candidate mixture. In addition, a SELEX process can be used to produce a candidate mixture, that is, a first SELEX process experiment can be used to produce a ligand-enriched mixture of nucleic acids that is used as the candidate mixture in a second SELEX process experiment. A candidate mixture can also comprise nucleic acids with one or more common structural motifs. As used herein, a candidate mixture is also sometimes referred to as a "pool" or a "library." For example, an "RNA pool" refers to a candidate mixture comprised of RNA.

In various embodiments, each nucleic acid in a candidate mixture may have fixed sequences on either side of a randomized region, to facilitate the amplification process. The nucleic acids in the candidate mixture of nucleic acids can each further comprise fixed regions or "tail" sequences at their 5' and 3' termini to prevent the formation of high molecular weight parasites during the amplification process.

As used herein, "nucleic acid," "oligonucleotide," and "polynucleotide" are used interchangeably to refer to a polymer of nucleotides of any length, and such nucleotides may include deoxyribonucleotides, ribonucleotides, and/or analogs or chemically modified deoxyribonucleotides or ribonucleotides. The terms "polynucleotide," "oligonucleotide," and "nucleic acid" include double- or single-stranded molecules as well as triple-helical molecules.

If present, chemical modifications of a nucleotide can include, singly or in any combination, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium)propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine), modifications at exocyclic amines, substitution of 4-thiouridine, substitution of 5-bromo- or 5-iodo-uracil, backbone modifications, methylations, unusual base-pairing combinations such as the isobases, isocytidine and isoguanidine, and the like.

Figure 14:
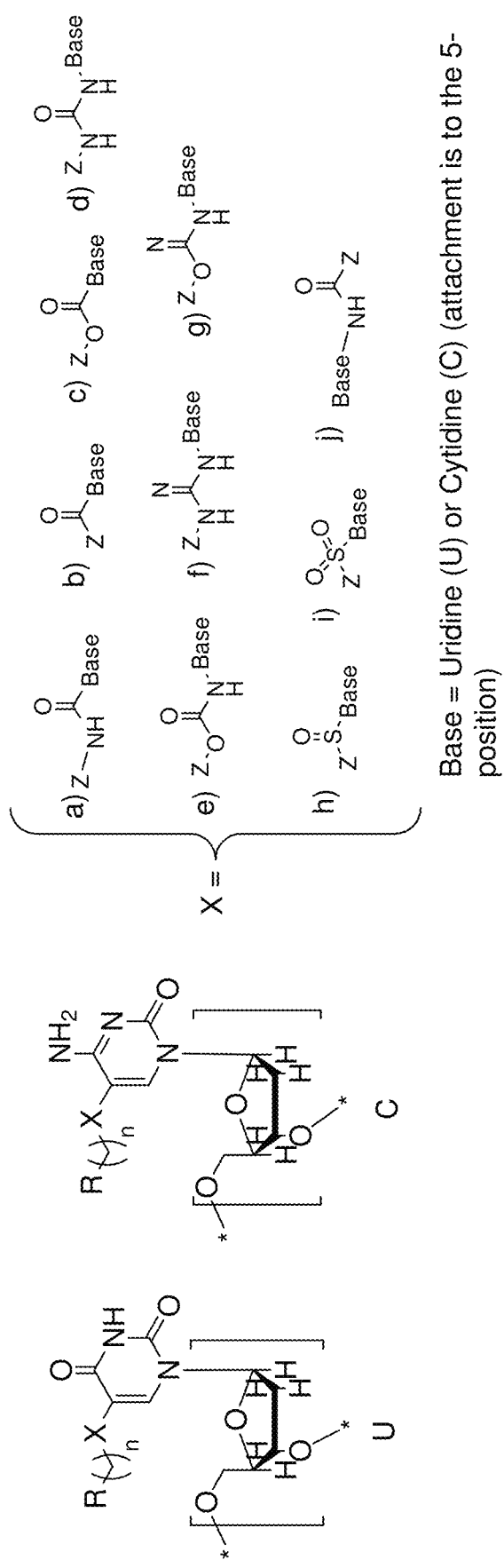
FIG. 14 describes the base modifications of nucleotides included in this disclosure. The R groups that may be used are described in addition to the linkers (X) that may be used between the nucleotide attachment point and the R group. The positions of attachment for the various "R" groups are also indicated on the respective R group.
Figure 14:
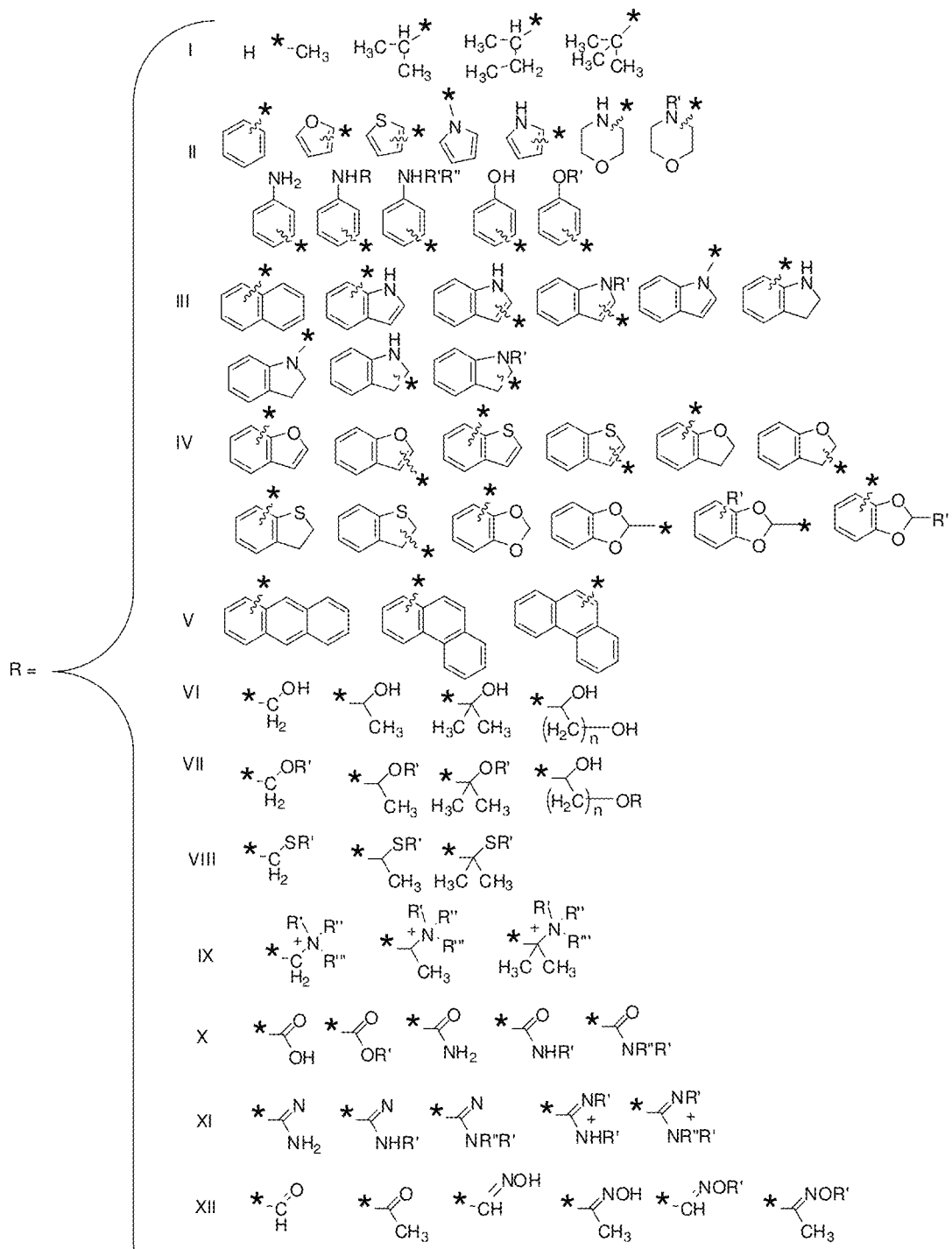

In one embodiment, the term "C-5 modified pyrimidine" refers to a pyrimidine with a modification at the C-5 position including, but not limited to those moieties illustrated in FIG. 14. Examples of a C-5 modified pyrimidine include those described in U.S. Pat. Nos. 5,719,273 and 5,945,527. Examples of a C-5 modification include substitution of deoxyuridine at the C-5 position with a substituent selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

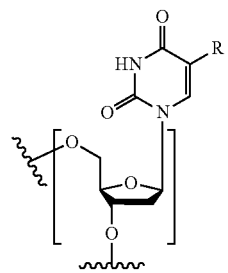

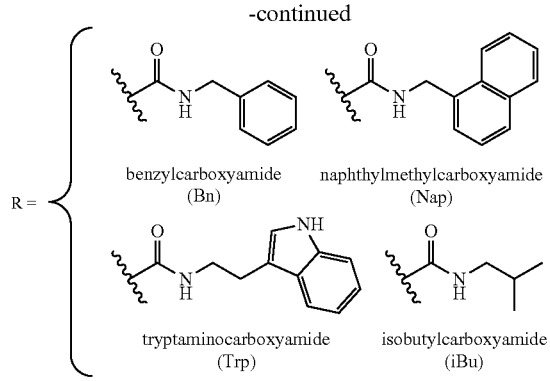

As delineated above, representative C-5 modified pyrimidines include: 5-(N-benzylcarboxamide)-2'-deoxyuridine (BndU), 5-(N-isobutylcarboxamide)-2'-deoxyuridine (iBudU), 5-(N-tryptaminocarboxamide)-2'-deoxyuridine (TrpdU) and 5-(N-naphthylmethylcarboxamide)-2'-deoxyuridine (NapdU).

Modifications can also include 3' and 5' modifications, such as capping or pegylation. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present in a sugar may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers. If present, a modification to the nucleotide structure may be imparted before or after assembly of a polymer. A sequence of nucleotides may be interrupted by non-nucleotide components. A polynucleotide may be further modified after polymerization, such as by conjugation with a labeling component.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Figure 13:
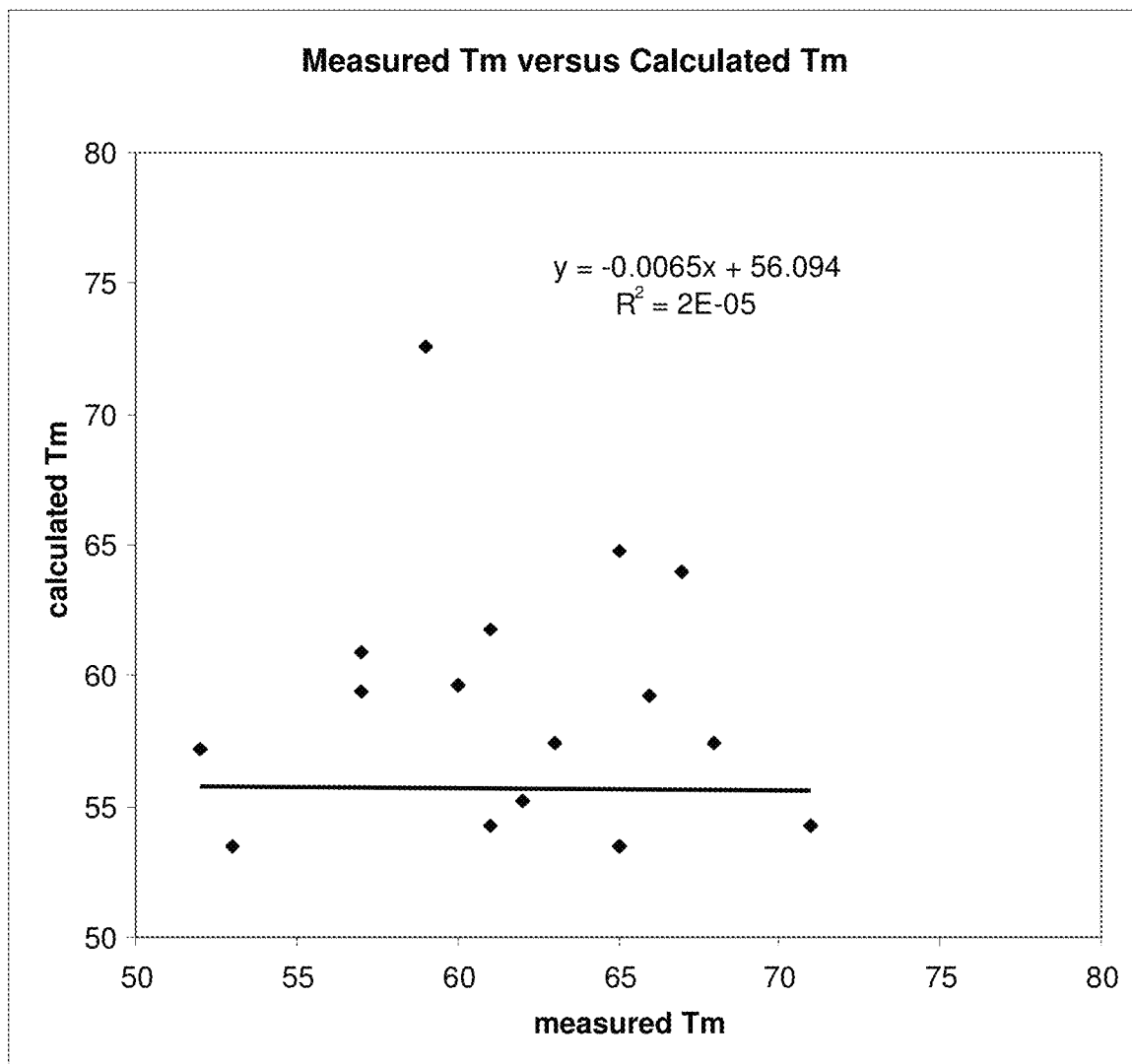
FIG. 13 illustrates a plot of the measured melting temperature of a number of slow off-rate aptamers relative to the predicted melting temperature.

In one embodiment, the variable region of the aptamer includes nucleotides that include modified bases. Certain modified aptamers may be used in any of the described methods, devices, and kits. These modified nucleotides have been shown to produce novel aptamers that have very slow off-rates from their respective targets while maintaining high affinity to the target. In one embodiment, the C-5 position of the pyrimidine bases may be modified. Aptamers containing nucleotides with modified bases have a number of properties that are different than the properties of standard aptamers that include only naturally occurring nucleotides (i.e., unmodified nucleotides). In one embodiment, the method for modification of the nucleotides includes the use of an amide linkage. However, other suitable methods for modification may be used. It has been surprisingly observed that the structure of the identified slow off-rate aptamers does not appear to be entirely in accordance with the structure predicted by standard base pairing models. This observation is supported by the fact that the measured melting temperatures of the slow off-rate aptamers are not consistent with the melting temperatures predicted by the models, see FIG. 13. As shown, there appears to be no correlation between the measured and predicted melting temperatures of the slow off-rate aptamers. On average, the calculated melting temperature (Tm) is 6° C. lower than the measured Tm. The measured melting temperatures indicate that slow off-rate aptamers including these modified nucleotides are more stable than may be predicted and potentially possess novel secondary structures. These modified aptamers also have different circular dichorism spectra than corresponding aptamers that include only unmodified nucleotides. In the case of many targets, slow off-rate aptamers to the target are more likely to be identified when modified nucleotides are used in the production of the initial library or candidate mixture.

As used herein, "modified nucleic acid" refers to a nucleic acid sequence containing one or more modified nucleotides. In some embodiments it may be desirable that the modified nucleotides are compatible with the SELEX process.

"Polypeptide," "peptide," and "protein" are used interchangeably herein to refer to polymers of amino acids of any length. The polymer may be linear or branched, it may comprise modified amino acids, and/or it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains.

As used herein, "photoreactive nucleotide" means any modified nucleotide that is capable of photocrosslinking with a target, such as a protein, upon irradiation with certain wavelengths of light. For example, photoaptamers produced by the photoSELEX process can include a photoreactive group selected from the following: 5-bromouracil (BrU), 5-iodouracil (IU), 5-bromovinyluracil, 5-iodovinyluracil, 5-azidouracil, 4-thiouracil, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-azidoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-bromodeoxyuridine, 8-bromo-2'-deoxyadenine, 5-iodo-2'-deoxyuracil, 5-iodo-2'-deoxycytosine, 5-[(4-azidophenacyl) thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine. A "photoreactive pyrimidine" means any modified pyrimidine that is capable of photocrosslinking with a target upon irradiation of certain wavelengths. Exemplary photoreactive pyrimidines include 5-bromo-uracil (BrdU), 5-bromo-cytosine (BrdC), 5-iodo-uracil (IdU), and 5-iodo-cytosine (IdC). In various embodiments, the photoreactive functional group will absorb wavelengths of light that are not absorbed by the target or the non-modified portions of the oligonucleotide.

"SELEX" refers to a process that combines the selection of nucleic acids that interact with a target in a desirable manner (e.g., binding to a protein) with the amplification of those selected nucleic acids. Optional iterative cycling of the selection/amplification steps allows selection of one or a small number of nucleic acids that interact most strongly with the target from a pool that contains a very large number of nucleic acids. Cycling of the selection/amplification procedure is continued until a selected goal is achieved. The SELEX methodology is described in the SELEX Patents. In some embodiments of the SELEX process, aptamers that bind non-covalently to their targets are generated. In other embodiments of the SELEX process, aptamers that bind covalently to their targets are generated.

As used herein the term "amplification" or "amplifying" means any process or combination of process steps that increases the amount or number of copies of a molecule or class of molecules.

"SELEX target" or "target molecule" or "target" refers herein to any compound upon which a nucleic acid can act in a desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. In one embodiment, a SELEX target does not include molecules that are known to bind nucleic acids, such as, for example, known nucleic acid binding proteins (e.g. transcription factors). Virtually any chemical or biological effector may be a suitable SELEX target. Molecules of any size can serve as SELEX targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein," incorporated herein by reference in its entirety. FIG. 7 lists over 500 targets for which aptamers have been produced including a variety of slow off-rate aptamers.

As used herein, "competitor molecule" and "competitor" are used interchangeably to refer to any molecule that can form a non-specific complex with a non-target molecule. In this context, non-target molecules include free aptamers, where, for example, a competitor can be used to inhibit the aptamer from binding (re-binding), non-specifically, to another non-target molecule. A "competitor molecule" or "competitor" is a set of copies of one type or species of molecule. "Competitor molecules" or "competitors" refer to more than one such set of molecules. Competitor molecules include, but are not limited to oligonucleotides, polyanions (e.g., heparin, herring sperm DNA, salmon sperm DNA, tRNA, dextran sulfate, polydextran, abasic phosphodiester polymers, dNTPs, and pyrophosphate). In various embodiments, a combination of one or more competitor can be used.

As used herein, "non-specific complex" refers to a non-covalent association between two or more molecules other than an aptamer and its target molecule. A non-specific complex represents an interaction between classes of molecules. Non-specific complexes include complexes formed between an aptamer and a non-target molecule, a competitor and a non-target molecule, a competitor and a target molecule, and a target molecule and a non-target molecule.

As used herein, the term "slow off-rate enrichment process" refers to a process of altering the relative concentrations of certain components of a candidate mixture such that the relative concentration of aptamer affinity complexes having slow dissociation rates is increased relative to the concentration of aptamer affinity complexes having faster, less desirable dissociation rates. In one embodiment, the slow off-rate enrichment process is a solution-based slow off-rate enrichment process. In this embodiment, a solution-based slow off-rate enrichment process takes place in solution, such that neither the target nor the nucleic acids forming the aptamer affinity complexes in the mixture are immobilized on a solid support during the slow off-rate enrichment process. In various embodiments, the slow off-rate enrichment process can include one or more steps, including the addition of and incubation with a competitor molecule, dilution of the mixture, or a combination of these (e.g., dilution of the mixture in the presence of a competitor molecule). Because the effect of an slow off-rate enrichment process generally depends upon the differing dissociation rates of different aptamer affinity complexes (i.e., aptamer affinity complexes formed between the target molecule and different nucleic acids in the candidate mixture), the duration of the slow off-rate enrichment process is selected so as to retain a high proportion of aptamer affinity complexes having slow dissociation rates while substantially reducing the number of aptamer affinity complexes having fast dissociation rates. The slow off-rate enrichment process may be used in one or more cycles during the SELEX process. When dilution and the addition of a competitor are used in combination, they may be performed simultaneously or sequentially, in any order. The slow off-rate enrichment process can be used when the total target (protein) concentration in the mixture is low. In one embodiment, when the slow off-rate enrichment process includes dilution, the mixture can be diluted as much as is practical, keeping in mind that the nucleic acids are recovered for subsequent rounds in the SELEX process. In one embodiment, the slow off-rate enrichment process includes the use of a competitor as well as dilution, permitting the mixture to be diluted less than might be necessary without the use of a competitor.

In one embodiment, the slow off-rate enrichment process includes the addition of a competitor, and the competitor is a polyanion (e.g., heparin or dextran sulfate (dextran)).

Heparin or dextran have been used in the identification of specific aptamers in prior SELEX selections. In such methods, however, heparin or dextran is present during the equilibration step in which the target and aptamer bind to form complexes. In such methods, as the concentration of heparin or dextran increases, the ratio of high affinity target/aptamer complexes to low affinity target/aptamer complexes increases. However, a high concentration of heparin or dextran can reduce the number of high affinity target/aptamer complexes at equilibrium due to competition for target binding between the nucleic acid and the competitor. By contrast, the presently described methods add the competitor after the target/aptamer complexes have been allowed to form and therefore does not affect the number of complexes formed. Addition of competitor after equilibrium binding has occurred between target and aptamer creates a non-equilibrium state that evolves in time to a new equilibrium with fewer target/aptamer complexes. Trapping target/aptamer complexes before the new equilibrium has been reached enriches the sample for slow off-rate aptamers since fast off-rate complexes will dissociate first.

In another embodiment, a polyanionic competitor (e.g., dextran sulfate or another polyanionic material) is used in the slow off-rate enrichment process to facilitate the identification of an aptamer that is refractory to the presence of the polyanion. In this context, "polyanionic refractory aptamer" is an aptamer that is capable of forming an aptamer/target complex that is less likely to dissociate in the solution that also contains the polyanionic refractory material than an aptamer/target complex that includes a non-polyanionic refractory aptamer. In this manner, polyanionic refractory aptamers can be used in the performance of analytical methods to detect the presence or amount or concentration of a target in a sample, where the detection method includes the use of the polyanionic material (e.g. dextran sulfate) to which the aptamer is refractory.

Thus, in one embodiment, a method for producing a polyanionic refractory aptamer is provided. In this embodiment, after contacting a candidate mixture of nucleic acids with the target, the target and the nucleic acids in the candidate mixture are allowed to come to equilibrium. A polyanionic competitor is introduced and allowed to incubate in the solution for a period of time sufficient to insure that most of the fast off-rate aptamers in the candidate mixture dissociate from the target molecule. Also, aptamers in the candidate mixture that may dissociate in the presence of the polyanionic competitor will be released from the target molecule. The mixture is partitioned to isolate the high affinity, slow off-rate aptamers that have remained in association with the target molecule and to remove any uncomplexed materials from the solution. The aptamer can then be released from the target molecule and isolated. The isolated aptamer can also be amplified and additional rounds of selection applied to increase the overall performance of the selected aptamers. This process may also be used with a minimal incubation time if the selection of slow off-rate aptamers is not needed for a specific application.

Thus, in one embodiment a modified SELEX process is provided for the identification or production of aptamers having slow (long) off-rates wherein the target molecule and candidate mixture are contacted and incubated together for a period of time sufficient for equilibrium binding between the target molecule and nucleic acids contained in the candidate mixture to occur. Following equilibrium binding an excess of competitor molecule, e.g., polyanion competitor, is added to the mixture and the mixture is incubated together with the excess of competitor molecule for a predetermined period of time. A significant proportion of aptamers having off rates that are less than this predetermined incubation period will dissociate from the target during the predetermined incubation period. Re-association of these "fast" off-rate aptamers with the target is minimized because of the excess of competitor molecule which can non-specifically bind to the target and occupy aptamer binding sites on the target. A significant proportion of aptamers having longer off rates will remain complexed to the target during the predetermined incubation period. At the end of the incubation period, partitioning nucleic acid-target complexes from the remainder of the mixture allows for the separation of a population of slow off-rate aptamers from those having fast off rates. A dissociation step can be used to dissociate the slow off-rate aptamers from their target and allows for isolation, identification, sequencing, synthesis and amplification of slow off-rate aptamers (either of individual aptamers or of a group of slow off-rate aptamers) that have high affinity and specificity for the target molecule. As with conventional SELEX the aptamer sequences identified from one round of the modified SELEX process can be used in the synthesis of a new candidate mixture such that the steps of contacting, equilibrium binding, addition of competitor molecule, incubation with competitor molecule and partitioning of slow off-rate aptamers can be iterated/repeated as many times as desired.

The combination of allowing equilibrium binding of the candidate mixture with the target prior to addition of competitor, followed by the addition of an excess of competitor and incubation with the competitor for a predetermined period of time allows for the selection of a population of aptamers having off rates that are much greater than those previously achieved.

In order to achieve equilibrium binding, the candidate mixture may be incubated with the target for at least about 5 minutes, or at least about 15 minutes, about 30 minutes, about 45 minutes, about 1 hour, about 2 hours, about 3 hours, about 4 hours, about 5 hours or about 6 hours.

The predetermined incubation period of competitor molecule with the mixture of the candidate mixture and target molecule may be selected as desired, taking account of factors such as the nature of the target and known off rates (if any) of known aptamers for the target. Predetermined incubation periods may be chosen from: at least about 5 minutes, at least about 10 minutes, at least about 20 minutes, at least about 30 minutes, at least 45 about minutes, at least about 1 hour, at least about 2 hours, at least about 3 hours, at least about 4 hours, at least about 5 hours, at least about 6 hours.

In other embodiments a dilution is used as an off rate enhancement process and incubation of the diluted candidate mixture, target molecule/aptamer complex may be undertaken for a predetermined period of time, which may be chosen from: at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours.

Embodiments of the present disclosure are concerned with the identification, production, synthesis and use of slow off-rate aptamers. These are aptamers which have a rate of dissociation ($t_{1/2}$) from a non-covalent aptamer-target complex that is higher than that of aptamers normally obtained by conventional SELEX. For a mixture containing non-covalent complexes of aptamer and target, the $t_{1/2}$ represents the time taken for half of the aptamers to dissociate from the aptamer-target complexes. The $t_{1/2}$ of slow dissociation rate aptamers according to the present disclosure is chosen from one of: greater than or equal to about 30 minutes; between about 30 minutes and about 240 minutes; between about 30 minutes to about 60 minutes; between about 60 minutes to about 90 minutes, between about 90 minutes to about 120 minutes; between about 120 minutes to about 150 minutes; between about 150 minutes to about 180 minutes; between about 180 minutes to about 210 minutes; between about 210 minutes to about 240 minutes.

A characterizing feature of an aptamer identified by a SELEX procedure is its high affinity for its target. An aptamer will have a dissociation constant ($k_d$) for its target that is chosen from one of: less than about 1 µM, less than about 100 nM, less than about 10 nM, less than about 1 nM, less than about 100 pM, less than about 10 pM, less than about 1 pM.

"Tissue target" or "tissue" refers herein to a certain subset of the SELEX targets described above. According to this definition, tissues are macromolecules in a heterogeneous environment. As used herein, tissue refers to a single cell type, a collection of cell types, an aggregate of cells, or an aggregate of macromolecules. This differs from simpler SELEX targets that are typically isolated soluble molecules, such as proteins. In some embodiments, tissues are insoluble macromolecules that are orders of magnitude larger than simpler SELEX targets. Tissues are complex targets made up of numerous macromolecules, each macromolecule having numerous potential epitopes. The different macromolecules which comprise the numerous epitopes can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue and muscle tissue.

Examples of tissues which fall within this definition include, but are not limited to, heterogeneous aggregates of macromolecules such as fibrin clots which are a cellular; homogeneous or heterogeneous aggregates of cells; higher ordered structures containing cells which have a specific function, such as organs, tumors, lymph nodes, arteries, etc, and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal, and viral structures.

As used herein, the term "labeling agent," "label," or "detectable moiety", or "detectable element" or "detectable component" refers to one or more reagents that can be used to detect a target molecule/aptamer complex. A detectable moiety or label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation, and (v) a specific polynucleotide sequence or recognition sequence that can act as a ligand, such as, for example, a repressor protein, wherein in the latter two instances the oligonucleotide primer or repressor protein will have, or be capable of having, a reporter molecule, and so forth. The reporter molecule can be a catalyst, such as an enzyme, a polynucleotide coding for a catalyst, promoter, dye, fluorescent molecule, quantum dot, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like. The label can be selected from electromagnetic or electrochemical materials. In one embodiment, the detectable label is a fluorescent dye. Other labels and labeling schemes will be evident to one skilled in the art based on the disclosure herein.

A detectable moiety (element or component) can include any of the reporter molecules listed above and any other chemical or component that may be used in any manner to generate a detectable signal. The detectable moiety may be detected via a fluorescent signal, a chemiluminescent signal, or any other detectable signal that is dependent upon the identity of the moiety. In the case where the detectable moiety is an enzyme (for example, alkaline phosphatase), the signal may be generated in the presence of the enzyme substrate and any additional factors necessary for enzyme activity. In the case where the detectable moiety is an enzyme substrate, the signal may be generated in the presence of the enzyme and any additional factors necessary for enzyme activity. Suitable reagent configurations for attaching the detectable moiety to a target molecule include covalent attachment of the detectable moiety to the target molecule, non-covalent association of the detectable moiety with another labeling agent component that is covalently attached to the target molecule, and covalent attachment of the detectable moiety to a labeling agent component that is non-covalently associated with the target molecule. Universal protein stains (UPS) are described in detail in U.S. patent application Ser. No. 10/504,696, filed Aug. 12, 2004, entitled "Methods and Reagents for Detecting Target Binding by Nucleic Acid Ligands".

"Solid support" refers herein to any substrate having a surface to which molecules may be attached, directly or indirectly, through either covalent or non-covalent bonds. The substrate materials may be naturally occurring, synthetic, or a modification of a naturally occurring material. Solid support materials may include silicon, graphite, mirrored surfaces, laminates, ceramics, plastics (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver, etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

The solid support may take any of a variety of configurations ranging from simple to complex and can have any one of a number of shapes, including a strip, plate, disk, rod, particle, including bead, tube, well, and the like. The surface may be relatively planar (e.g., a slide), spherical (e.g., a bead), cylindrical (e.g., a column), or grooved. Exemplary solid supports that may be used include microtitre wells, microscope slides, membranes, paramagnetic beads, charged paper, Langmuir-Blodgett films, silicon wafer chips, flow through chips, and microbeads.

As used herein, "partitioning" means any process whereby one or more components of a mixture are separated from other components of the mixture. For example, aptamers bound to target molecules can be partitioned from other nucleic acids that are not bound to target molecules and from non-target molecules. More broadly stated, partitioning allows for the separation of all the nucleic acids in a candidate mixture into at least two pools based on their relative affinity and/or dissociation rate to the target molecule. Partitioning can be accomplished by various methods known in the art, including filtration, affinity chromatography, liquid-liquid partitioning, HPLC, etc. For example, nucleic acid-protein pairs can be bound to nitrocellulose filters while unbound nucleic acids are not. Columns that specifically retain nucleic acid-target complexes can also be used for partitioning. For example, oligonucleotides able to associate with a target molecule bound on a column allow the use of column chromatography for separating and isolating the highest affinity aptamers. Beads upon which target molecules are conjugated can also be used to partition aptamers in a mixture. If the beads are paramagnetic, the partitioning can be achieved through application of a magnetic field. Surface plasmon resonance technology can be used to partition nucleic acids in a mixture by immobilizing a target on a sensor chip and flowing the mixture over the chip, wherein those nucleic acids having affinity for the target can be bound to the target, and the remaining nucleic acids can be washed away. Liquid-liquid partitioning can be used as well as filtration gel retardation and density gradient centrifugation. Affinity tags on the target molecules can also be used to separate nucleic acid molecules bound to the tagged target from aptamers that are free in solution. For example, biotinylated target molecules, along with aptamers bound to them, can be sequestered from the solution of unbound nucleic acid sequences using streptavidin paramagnetic beads. Affinity tags can also be incorporated into the aptamer during preparation.

As used herein, "photoSELEX" is an acronym for Photochemical Systematic Evolution of Ligands by Exponential enrichment and refers to embodiments of the SELEX process in which photocrosslinking aptamers are generated. In one embodiment of the photoSELEX process, a photoreactive nucleotide activated by absorption of light is incorporated in place of a native base in either RNA- or in ssDNA-randomized oligonucleotide libraries, the nucleic acid target molecule mixture is irradiated causing some nucleic acids incorporated in nucleic acid-target molecule complexes to crosslink to the target molecule via the photoreactive functional groups, and the selection step is a selection for photocrosslinking activity. The photoSELEX process is described in great detail in the PhotoSELEX Patents.

As used herein, "photoaptamer" and "photoreactive aptamer" are used interchangeably to refer to an aptamer that contains one or more photoreactive functional groups that can covalently bind to or "crosslink" with a target molecule. For example, a naturally occurring nucleic acid residue may be modified to include a chemical functional group that confers photoreactivity upon the nucleic acid residue upon exposure to a radiation source of an appropriate wavelength. In some embodiments, a photoreactive aptamer is identified initially. In other embodiments, an aptamer is first identified and is subsequently modified to incorporate one or more photoreactive functional groups, thereby generating a photoaptamer. In these embodiments, one or more photoreactive nucleic acid residues can be incorporated into an aptamer either by substituting a photoreactive nucleic acid residue in the place of one or more other nucleotides, such as one or more of the thymidine and/or cytidine nucleotides in the aptamer, for example, or by modifying one or more nucleic acid residues to include a photoreactive functional group.

Exemplary photoreactive functional groups that may be incorporated by a photoaptamer include 5-bromouracil, 5-iodouracil, 5-bromovinyluracil, 5-iodovinyluracil, 5-azidouracil, 4-thiouracil, 5-thiouracil, 4-thiocytosine, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-aziodoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-[(4-azidophenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine.

In addition to these exemplary nucleoside-based photoreactive functional groups, other photoreactive functional groups that can be added to a terminal end of an aptamer using an appropriate linker molecule can also be used. Such photoreactive functional groups include benzophenone, anthraquinone, 4-azido-2-nitro-aniline, psoralen, derivatives of any of these, and the like.

A photoreactive functional group incorporated by a photoaptamer may be activated by any suitable method. In one embodiment, a photoaptamer containing a photoreactive functional group can be crosslinked to its target by exposing the photoaptamer and its bound target molecule to a source of electromagnetic radiation. Suitable types of electromagnetic radiation include ultraviolet light, visible light, X-rays, and gamma rays. Suitable radiation sources include sources that utilize either monochromatic light or filtered polychromatic light.

As used herein, the term "the affinity SELEX process" refers to embodiments of the SELEX process in which non-photocrosslinking aptamers to targets are generated. In some embodiments of the affinity SELEX process, the target is immobilized on a solid support either before or after the target is contacted with the candidate mixture of nucleic acids. The association of the target with the solid support allows nucleic acids in the candidate mixture that have bound and in the case where a slow off-rate enrichment process is used, stay bound to the target to be partitioned from the remainder of the candidate mixture. The term "bead affinity SELEX process" refers to particular embodiments of the affinity SELEX process where the target is immobilized on a bead, for example, before contact with the candidate mixture of nucleic acids. In some embodiments, the beads are paramagnetic beads. The term "filter affinity SELEX process" refers to embodiments where nucleic acid target complexes are partitioned from candidate mixture by virtue of their association with a filter, such as a nitrocellulose filter. This includes embodiments where the target and nucleic acids are initially contacted in solution, and contacted with the filter, and also includes embodiments where nucleic acids are contacted with target that is pre-immobilized on the filter. The term "plate affinity SELEX process" refers to embodiments where the target is immobilized on the surface of a plate, such as, for example, a multi-well microtiter plate. In some embodiments, the plate is comprised of polystyrene. In some embodiments, the target is attached to the plate in the plate affinity SELEX process through hydrophobic interactions.

The present disclosure describes improved SELEX methods for generating aptamers that are capable of binding to target molecules. More specifically, the present disclosure describes methods for identifying aptamers and/or photoaptamers having slower rates of dissociation from their respective targeted molecules than aptamers obtained with previous SELEX methods. The disclosure further describes aptamers and/or photoaptamers obtained using the methods described herein and methods of using the same.

In one embodiment, a method is provided for identifying an aptamer having a slow rate of dissociation from its target molecule, the method comprising (a) preparing a candidate mixture of nucleic acid sequences; (b) contacting the candidate mixture with a target molecule wherein nucleic acids with the highest relative affinities to the target molecule preferentially bind the target molecule, forming nucleic acid-target molecule complexes; (c) applying a slow off-rate enrichment process to allow the dissociation of nucleic acid-target molecule complexes with relatively fast dissociation rates; (d) partitioning the remaining nucleic acid-target molecule complexes from both free nucleic acids and non-target molecules in the candidate mixture; and (e) identifying an aptamer to the target molecule. The process may further include the iterative step of amplifying the nucleic acids that bind to the target molecule to yield a mixture of nucleic acids enriched in sequences that are able to bind to the target molecule yet produce nucleic acid-target molecule complexes having slow dissociation rates. As defined above, the slow off-rate enrichment process can be selected from (a) diluting the candidate mixture containing the nucleic acid-target molecule complexes; (b) adding at least one competitor to the candidate mixture containing the nucleic acid-target molecule complexes, and diluting the candidate mixture containing the nucleic acid-target molecule complexes; (c) and adding at least one competitor to the candidate mixture containing the nucleic acid-target molecule complexes.

In one embodiment, a method is provided for producing an aptamer having a slow rate of dissociation from its target molecule, the method comprising (a) preparing a candidate mixture of nucleic acid sequences; (b) contacting the candidate mixture with a target molecule wherein nucleic acids with the highest relative affinities to the target molecule preferentially bind the target molecule, forming nucleic acid-target molecule complexes; (c) applying a slow off-rate enrichment process to allow the dissociation of nucleic acid-target molecule complexes with relatively fast dissociation rates; (d) partitioning the remaining nucleic acid-target molecule complexes from both free nucleic acids and non-target molecules in the candidate mixture; and (e) producing an aptamer to the target molecule. The process may further include the iterative step of amplifying the nucleic acids that bind to the target molecule to yield a mixture of nucleic acids enriched in sequences that are able to bind to the target molecule yet produce nucleic acid-target molecule complexes having slow dissociation rates. As defined above, the slow off-rate enrichment process can be selected from (a) diluting the candidate mixture containing the nucleic acid-target molecule complexes; (b) adding at least one competitor to the candidate mixture containing the nucleic acid-target molecule complexes, and diluting the candidate mixture containing the nucleic acid-target molecule complexes; (c) and adding at least one competitor to the candidate mixture containing the nucleic acid-target molecule complexes.

In one embodiment, a method is provided for identifying an aptamer having a slow rate of dissociation from its target molecule, the method comprising: (a) preparing a candidate mixture of nucleic acids; (b) contacting the candidate mixture with a target molecule, wherein nucleic acids having an increased affinity to the target molecule relative to other nucleic acids in the candidate mixture bind the target molecule, forming nucleic acid-target molecule complexes; (c) incubating the candidate mixture and target molecule together for a period of time sufficient to achieve equilibrium binding; (d) applying a slow off-rate enrichment process to allow the dissociation of nucleic acid-target molecule complexes with relatively fast dissociation rates to the mixture of (c); (e) incubating the mixture of the candidate mixture, the nucleic acid-target molecule complexes and the competitor molecule from (d) for a predetermined period of time; (f) partitioning the nucleic acid-target molecule complexes from the candidate mixture; (g) dissociating the nucleic acid-target molecule complexes to generate free nucleic acids; (h) amplifying the free nucleic acids to yield a mixture of nucleic acids enriched in nucleic acid sequences that are capable of binding to the target molecule with increased affinity, whereby an aptamer to the target molecule may be identified. As defined above, the slow off-rate enrichment process can be selected from (a) diluting the candidate mixture containing the nucleic acid-target molecule complexes; (b) adding at least one competitor to the candidate mixture containing the nucleic acid-target molecule complexes, and diluting the candidate mixture containing the nucleic acid-target molecule complexes; (c) and adding at least one competitor to the candidate mixture containing the nucleic acid-target molecule complexes.

In another embodiment, a method is provided for producing an aptamer having a slow rate of dissociation from its target molecule, the method comprising: (a) preparing a candidate mixture of nucleic acids; (b) contacting the candidate mixture with a target molecule, wherein nucleic acids having an increased affinity to the target molecule relative to other nucleic acids in the candidate mixture bind the target molecule, forming nucleic acid-target molecule complexes; (c) incubating the candidate mixture and target molecule together for a period of time sufficient to achieve equilibrium binding; (d) applying a slow off-rate enrichment process to allow the dissociation of nucleic acid-target molecule complexes with relatively fast dissociation rates to the mixture of (c); (e) incubating the mixture of the candidate mixture, the nucleic acid-target molecule complexes and the competitor molecule from (d) for a predetermined period of time; (f) partitioning the nucleic acid-target molecule complexes from the candidate mixture; (g) dissociating the nucleic acid-target molecule complexes to generate free nucleic acids; (h) amplifying the free nucleic acids to yield a mixture of nucleic acids enriched in nucleic acid sequences that are capable of binding to the target molecule with increased affinity, whereby an aptamer to the target molecule may be produced. As defined above, the slow off-rate enrichment process can be selected from (a) diluting the candidate mixture containing the nucleic acid-target molecule complexes; (b) adding at least one competitor to the candidate mixture containing the nucleic acid-target molecule complexes, and diluting the candidate mixture containing the nucleic acid-target molecule complexes; (c) and adding at least one competitor to the candidate mixture containing the nucleic acid-target molecule complexes.

In another embodiment, a method is provided of identifying an aptamer having a slow rate of dissociation from its target molecule, the method comprising: (a) preparing a candidate mixture of nucleic acids, wherein the candidate mixture comprises modified nucleic acids in which one, several or all pyrimidines in at least one, or each, nucleic acid of the candidate mixture is chemically modified at the 5-position; (b) contacting the candidate mixture with a target molecule, wherein nucleic acids having an increased affinity to the target molecule relative to other nucleic acids in the candidate mixture bind the target molecule, forming nucleic acid-target molecule complexes; (c) partitioning the increased affinity nucleic acids from the remainder of the candidate mixture; and (d) amplifying the increased affinity nucleic acids to yield a mixture of nucleic acids enriched in nucleic acid sequences that are capable of binding to the target molecule with increased affinity, whereby an aptamer to the target molecule may be identified.

In another embodiment, a method is provided for producing an aptamer having a slow rate of dissociation from its target molecule, said method comprising preparing or synthesizing an aptamer that includes a nucleic acid sequence identified by the following process: (a) preparing a candidate mixture of nucleic acids, wherein the candidate mixture comprises modified nucleic acids in which one, several or all pyrimidines in at least one, or each, nucleic acid of the candidate mixture is chemically modified at the 5-position; (b) contacting the candidate mixture with a target molecule, wherein nucleic acids having an increased affinity to the target molecule relative to other nucleic acids in the candidate mixture bind the target molecule, forming nucleic acid-target molecule complexes; (c) partitioning the increased affinity nucleic acids from the remainder of the candidate mixture; and (d) amplifying the increased affinity nucleic acids to yield a mixture of nucleic acids enriched in nucleic acid sequences that are capable of binding to the target molecule with increased affinity, whereby an aptamer to the target molecule is identified.

In another embodiment, a non-covalent complex of an aptamer and its target is provided, wherein the rate of dissociation ($t_{1/2}$) of the aptamer from the target is chosen from one of: greater than or equal to about 30 minutes; between about 30 minutes and about 240 minutes; about 30 minutes to about 60 minutes; about 60 minutes to about 90 minutes; about 90 minutes to about 120 minutes; about 120 minutes to about 150 minutes; about 150 minutes to about 180 minutes; about 180 minutes to about 210 minutes; about 210 minutes to about 240 minutes.

In another embodiment, a non-covalent complex of an aptamer and a target is provided, wherein the aptamer has a $K_d$ for the target of about 100 nM or less, wherein the rate of dissociation ($t_{1/2}$) of the aptamer from the target is greater than or equal to about 30 minutes, and wherein one, several or all pyrimidines in the nucleic acid sequence of the aptamer are modified at the 5-position of the base. The modifications may be selected from the group of compounds shown in FIG. 14, these modifications are referred to as "base modified nucleotides". Aptamers may be designed with any combination of the base modified pyrimidines desired.

Improved methods for performing SELEX with modified nucleotides, including nucleotides which contain photoactive groups or nucleotides which contain placeholders for photoactive groups are disclosed in U.S. application Ser. No. 12/175,388, entitled "Improved SELEX and PHOTOSELEX" which is being filed concurrently with the instant application and which is incorporated herein by reference in its entirety. In another embodiment, the candidate mixture of nucleic acid molecules includes nucleic acids containing modified nucleotide bases that may aid in the formation of modified nucleic acid-target complexes with relatively slow dissociation rates.

The various methods and steps described herein can be used to generate an aptamer capable of either (1) binding to a target molecule or (2) binding to a target molecule and subsequently forming a covalent linkage with the target molecule upon irradiation.

Aptamers identified according to the methods described herein are useful in a range of diagnostic and therapeutic methods. Slow off-rate aptamers will bind to the target for a longer duration. This is useful in diagnostic methods where the binding of an aptamer to the target may be used to detect the presence, absence, amount or quantity of the target molecule and a prolonged interaction of the aptamer and target facilitates such detection. A similar advantage may be afforded where slow off-rate aptamers are used in imaging methods, in vitro or in vivo. A prolonged interaction of aptamer and target also provides for improved therapeutic methods of treatment where the prolonged interaction may allow for an improved therapeutic effect, e.g. owing to the longer activation or inhibition of the target molecule or downstream signaling cascade.

Accordingly, in various embodiments, slow off-rate aptamers obtained, identified or produced by the described methods can be used in a variety of methods of medical treatment or methods of diagnosis (in vitro or in vivo). In one embodiment, slow off-rate aptamers can be used in a method of treatment of disease. In one embodiment, slow off-rate aptamers can be used in a method for diagnosis of disease in vivo. In another embodiment, slow off-rate aptamers can be used in vitro for the diagnosis of disease. In another embodiment, a slow off-rate aptamer can be used in the manufacture of a therapeutic (e.g. pharmaceutical composition) or the manufacture of a diagnostic agent for use in a method of treatment or diagnosis of disease. Diagnostic or therapeutic applications of slow off-rate aptamers may involve a diagnostic or therapeutic outcome that depends on the specific and/or high affinity binding of the slow off-rate aptamer to its target. Slow off-rate aptamers may also be used in target validation and high throughput screening assays in the drug development process.

In one embodiment, slow off-rate aptamers are suitable reagents for molecular imaging in vivo. In this embodiment, a slow off-rate aptamer may be used in vivo to detect the presence of a pathology, disease process, or other condition in the body of an individual (e.g., a human or an animal), where the binding of the aptamer to its target indicates the presence of the disease process or other condition. For example, an aptamer to the VEGF receptor may be used in vivo to detect the presence of cancer in a particular area (e.g., a tissue, an organ, etc.) of the body of an individual, as the VEGF receptor is abundantly expressed within tumors and their neovasculature, or an aptamer to the EGF receptor may be used in vivo to detect the presence of cancer in a particular area (e.g., a tissue, an organ, etc.) of the body of an individual, as the EGF receptor is often expressed at high levels on tumor cells. That is, the molecular target will be the extracellular domain (ECD) of an induced receptor, as such targets are located outside of the cells and are accessible through the vasculature. Additionally, the ECDs tend to be localized at the site of pathology, even though some small fraction of the specific ECD may be shed through biological processes, including cell death.

The obvious candidates for molecular imaging, high affinity monoclonal antibodies, have not become the reagent of choice for this application. Molecular imaging reagents have precise requirements. They must have high binding activity for their intended target, and low binding activity for other targets in a human or animal. Slow off-rate aptamers have unique advantages that render them desirable for use in molecular imaging in vivo. On the one hand, they are selected to have slow dissociation rate constants, thus allowing residence in vivo on the intended target for a substantial length of time (at least about 30 minutes). On the other hand, slow off-rate aptamers are expected to have very fast clearance from the vasculature. Slow dissociation rate constants and fast clearance from the vasculature are two desired properties for molecular imaging in vivo. From a kinetic prospective, good in vivo molecular imaging reagents must stay localized at the site of the pathology while the free reagent concentration in the surrounding vasculature becomes low. This is a signal-to-noise constraint. Suitable signal-to-noise ratios may be obtained by accumulation of signal at the site of pathology in excess of the signal in the vasculature, or may be obtained by retention of a signal at the site of the pathology while the vasculature concentration is diminished.

Aptamers that do not have slow off-rate properties, of about the same molecular weight and net charge as slow off-rate aptamers, have been studied in animals and humans for more than a decade. Generally, it has been found that these aptamers clear from the vasculature quickly, usually by entering the kidney and/or the liver and then being further metabolized for excretion. Such aptamers show so-called "first pass" clearance unless high molecular weight adducts (such as, for example, PEG) are linked to the aptamers. Experiments have been done with an aptamer whose target is tenascin C, an extracellular protein (not an ECD) found at high concentrations in some tumors. In those experiments, the tenascin C-specific aptamer cleared quickly and was able to be retained at the site of the tumor because the extracellular local concentration of tenascin C is very high. Slow off-rate aptamers, by contrast, will maintain the fast clearance rate of aptamers, but offer a kinetic advantage due to their slow dissociation rates, rendering them suitable for use with targets whose presence at the site of interest (e.g., the site of pathology) may be somewhat sparse (ECDs on tumors, for example).

Alternative reagents for molecular imaging do not share the two slow off-rate aptamer properties (i.e., slow dissociation rate and fast clearance from the body). Monoclonal antibodies often have high affinity and specificity, and may have slow dissociation rate constants; however, monoclonal antibodies have very slow clearance rates from the vasculature. Short peptides, identified through, for example, phage display, may have fast clearance but poor affinity and specificity and fast dissociation rates from their intended targets. Affibodies, a particular peptide version of an antibody mimetic, may have reasonable affinity and specificity and may have faster clearance than monoclonal antibodies, yet in order to achieve slow dissociation rates from their targets, affibodies are often made into dimers and higher order multimers, slowing their clearance at the same time that their dissociation rates are enhanced.

Slow off-rate aptamers may be used for molecular imaging in vivo with one or more low molecular weight adducts to both protect the slow off-rate aptamer from nucleases in the body and detect the intended target once bound by the slow off-rate aptamer. For example, slow off-rate aptamers may be attacked by nucleases in the blood, typically exonucleases (for DNA) that are easily blocked by using exonuclease refractive adducts at the 5' and 3' terminal positions of the slow off-rate aptamer, or endonucleases (for RNA) that are easily blocked by incorporating endonuclease refractive pyrimidines (such as, for example, 2' fluoro nucleotides) in the slow off-rate aptamer. Detection of the slow off-rate aptamer-target complex may be achieved by attaching a detection moiety to the slow off-rate aptamer. In some embodiments, the detection moiety for these purposes may include cages for radioactive molecules (e.g., technetium 99), clusters of iron for magnetic resonance detection, isotopes of fluorine for PET imaging, and the like. The modifications made to the slow off-rate aptamer to protect the integrity of the slow off-rate aptamer in the body and enable detection of the intended target should be designed such that they do not interfere with the slow off-rate aptamer's interaction with its target and do not cause the slow off-rate aptamer to clear too slowly from the vasculature.

Diagnostic or assay devices, e.g. columns, test strips or biochips, having one or more slow off-rate aptamers adhered to a solid surface of the device are also provided. The aptamer(s) may be positioned so as to be capable of binding target molecules that are contacted with the solid surface to form aptamer-target complexes that remain adhered to the surface of the device, thereby capturing the target and enabling detection and optionally quantitation of the target. An array of slow off-rate aptamers (which may be the same or different) may be provided on such a device.

In another embodiment, complexes including a slow off-rate aptamer and a target molecule are provided. In other embodiments, a class of aptamers characterized by having high affinity for their corresponding target molecules and slow dissociation rates ($t_{1/2}$) from a non-covalent complex of the aptamer and target is provided.

With reference to FIG. 1A, the basic SELEX process generally begins with the preparation of a candidate mixture of nucleic acids of differing sequence. The candidate mixture generally includes nucleic acid sequences that include two fixed regions (i.e., each of the members of the candidate mixture contains the same sequences in the same location) and a variable region. Typically, the fixed sequence regions are selected such that they assist in the amplification steps described below, or enhance the potential of a given structural arrangement of the nucleic acids in the candidate mixture. The variable region typically provides the target binding region of each nucleic acid in the candidate mixture, and this variable region can be completely randomized (i.e., the probability of finding a base at any position being one in four) or only partially randomized (e.g., the probability of finding a base at any location can be selected at any level between 0 and 100 percent). The prepared candidate mixture is contacted with the selected target under conditions that are favorable for binding to occur between the target and members of the candidate mixture. Under these conditions, the interaction between the target and the nucleic acids of the candidate mixture generally forms nucleic acid-target pairs that have the strongest relative affinity between members of the pair. The nucleic acids with the highest affinity for the target are partitioned from those nucleic acids with lesser affinity to the target. The partitioning process is conducted in a manner that retains the maximum number of high affinity candidates. Those nucleic acids selected during partitioning as having a relatively high affinity to the target are amplified to create a new candidate mixture that is enriched in nucleic acids having a relatively high affinity for the target. By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a very small number of unique nucleic acids representing those nucleic acids from the original candidate mixture that have the highest affinity to the target molecule. However, this basic SELEX process does not select for aptamers that have slow off-rates from their targets.

The SELEX Patents and the PhotoSELEX Patents describe and elaborate on this process in great detail. These patents include descriptions of the various targets that can be used in the process; methods for the preparation of the initial candidate mixture; methods for partitioning nucleic acids within a candidate mixture; and methods for amplifying partitioned nucleic acids to generate enriched candidate mixtures. The SELEX Patents also describe aptamer solutions obtained to a number of different types of target molecules, including protein targets wherein the protein is and is not a nucleic acid binding protein.

Figure 1B:
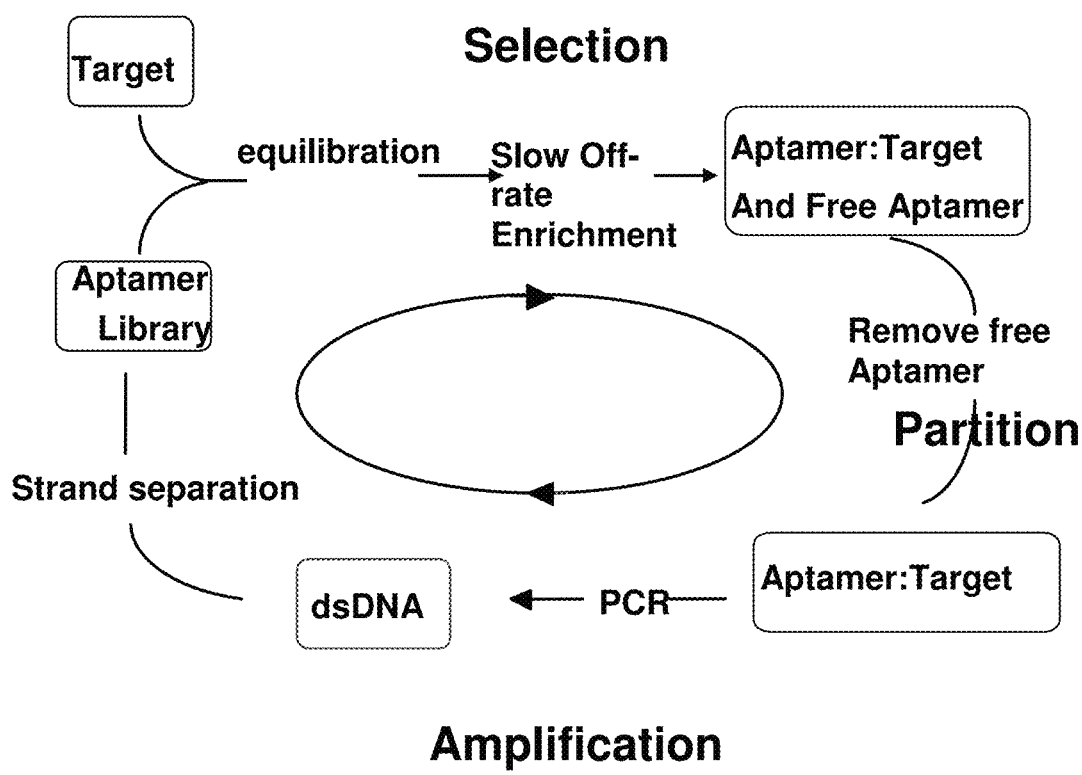

With reference to FIG. 1B the modified SELEX process disclosed herein includes the introduction of a slow off-rate enrichment process following equilibration of the candidate mixture of nucleic acids with the target or targets and a partitioning step prior to subsequent steps in the SELEX process. Introduction of a slow off-rate enrichment process to the basic SELEX process provides a means for enrichment of aptamer affinity complexes with slow dissociation rates from a set of nucleic acid-target complexes that includes a variety of dissociation rates. Thus, the modified SELEX process provides a method for identifying aptamers that bind target molecules and, once bound, have relatively slow rates of dissociation (also referred to herein as "off-rates") from the target molecule.

As used herein "binding" generally refers to the formation of a non-covalent association between the ligand and the target, although such binding is not necessarily reversible. The terms "nucleic acid-target complex" or "complex" or "affinity complex" are used to refer to the product of such non-covalent binding association.

In various embodiments, the slow off-rate aptamers can be single- or double-stranded RNA or DNA oligonucleotides. The aptamers can contain non-standard or modified bases. Further, the aptamers can contain any type of modification. As used herein, a "modified base" may include a relatively simple modification to a natural nucleic acid residue, which modification confers a change in the physical properties of the nucleic acid residue. Such modifications include, but are not limited to, modifications at the 5-position of pyrimidines, substitution with hydrophobic groups, e.g., benzyl, iso-butyl, indole, or naphthylmethyl, or substitution with hydrophilic groups, e.g., quaternary amine or guanidinium, or more "neutral" groups, e.g., imidazole and the like. Additional modifications may be present in the ribose ring, e.g., 2'-position, such as 2'-amino (2'-NH$_2$) and 2'-fluoro (2'-F), or the phosphodiester backbone, e.g., phosphorothioates or methyl phosphonates.

In various embodiments, a candidate mixture containing a randomized set of nucleic acid sequences containing modified nucleotide bases is mixed with a quantity of the target molecule and allowed to establish binding equilibrium with the target molecule. Generally, only some of those nucleic acids that bind with high affinity to the target molecule will efficiently partition with the target.

In various embodiments, the candidate mixture includes nucleic acid sequences having variable regions that include modified groups. The modified groups can be modified nucleotide bases. The variable region can contain fully or partially random sequences; it can also contain subportions of a fixed sequence that is incorporated within the variable region. The nucleotides within the fixed regions can also contain modified nucleotide bases, or they can contain the standard set of naturally occurring bases.

In some embodiments, amplification occurs after members of the test mixture have been partitioned, and it is the nucleic acid that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method may result in the proportions of the amplified mixture being representative of the proportions of different sequences in the mixture prior to amplification. It is known that many modifications to nucleic acids are compatible with enzymatic amplification. Modifications that are not compatible with amplification can be made after each round of amplification, if necessary.

The nucleic acid candidate mixture can be modified in various ways to enhance the probability of the nucleic acids having facilitating properties or other desirable properties, particularly those that enhance the interaction between the nucleic acid and the target. Contemplated modifications include modifications that introduce other chemical groups that have the correct charge, polarizability, hydrogen bonding, or electrostatic interaction to enhance the desired ligand-target interactions. The modifications that may enhance the binding properties, including the affinity and/or dissociation rates, of the nucleic acid, for example, include hydrophilic moieties, hydrophobic moieties, rigid structures, functional groups found in proteins such as imidazoles, primary alcohols, carboxylates, guanidinium groups, amino groups, thiols and the like. Modifications can also be used to increase the survival of aptamer-target complexes under stringent selection pressures that can be applied to produce slow off-rate aptamers to a wide range of targets. In one embodiment, BndU (5-(N-benzylcarboxyamide)-dU) is used in the generation of the candidate mixtures used to produce slow off-rate aptamers, although other modified nucleotides are well suited to the production of such aptamers. Other modified nucleotides are shown in FIG. 14.

A modified nucleotide candidate mixture for the purpose of this application is any RNA or DNA candidate mixture that includes both naturally occurring and other than the naturally occurring nucleotides. Suitable modifications include modifications on every residue of the nucleic acid, on a single residue of the nucleic acid, on random residues, on all pyrimidines or all purines, on all occurrences of a specific base (i.e., G, C, A, T or U) in the nucleic acid, or any other modification scheme that may be suitable for a particular application. It is recognized that modification is not a prerequisite for facilitating activity or binding ability of the aptamers. Aptamers may include modified dUTP and dCTP residues.

Candidate mixtures for slow off-rate aptamers may comprise a set of pyrimidines having a different modification at the C-5 base position. The C-5 modification may be introduced through an amide linkage, directly, or indirectly, or through another type of linkage. These candidate mixtures are used in a SELEX process to identify slow off-rate aptamers. This process may be also include the use of the slow off-rate enrichment process. Candidate mixtures may be produced enzymatically or synthetically.

As described above, the nucleotides can be modified in any number of ways, including modifications of the ribose and/or phosphate and/or base positions. Certain modifications are described in U.S. Pat. No. 5,660,985 entitled "High Affinity Nucleic Acid Ligands Containing Modified Nucleotides," U.S. Pat. No. 5,428,149 entitled "Method for Palladium Catalyzed Carbon-Carbon Coupling and Products," U.S. Pat. No. 5,580,972 entitled "Purine Nucleoside Modifications by Palladium Catalyzed Methods," all of which are incorporated by reference herein. In one embodiment, modifications are those wherein another chemical group is attached to the 5-position of a pyrimidine or the 2' position of a sugar. There is no limitation on the type of other chemical group that can be incorporated on the individual nucleotides. In some embodiments, the resulting modified nucleotide is amplifiable or can be modified subsequent to the amplification steps (see, e.g., U.S. Pat. No. 6,300,074 entitled "Systematic evolution of ligands by exponential enrichment: Chemi-SELEX").

In yet other embodiments, certain nucleotides are modified to produce aptamers that bind and form a covalent crosslink to their target molecule upon photo-activation of the affinity complex. This method encompasses aptamers that bind, photocrosslink, and/or photoinactivate target molecules. In various embodiments, the aptamers contain photoreactive groups that are capable of photocrosslinking to the target molecule upon irradiation with light. In other embodiments, the aptamers are capable of bond formation with the target in the absence of irradiation.

A photoreactive group can be any chemical structure that contains a photochromophore and that is capable of photocrosslinking with a target molecule. Although referred to herein as a photoreactive group, in some cases, as described below, irradiation is not necessary for covalent binding to occur between the aptamer and the target. In some embodiments, the photoreactive group will absorb light of a wavelength that is not absorbed by the target or the non-modified portions of the oligonucleotide. Photoreactive groups include 5-halo-uridines, 5-halo-cytosines, 7-halo-adenosines, 2-nitro-5-azidobenzoyls, diazirines, aryl azides, fluorinated aryl azides, benzophenones, amino-benzophenones, psoralens, anthraquinones, etc.

The photoreactive groups generally form bonds with the target upon irradiation of the associated nucleic acid-target pair. In some cases, irradiation is not required for bond formation to occur. The photocrosslink that typically occurs will be the formation of a covalent bond between the associated aptamer and the target. However, a tight ionic interaction between the aptamer and target may also occur upon irradiation.

In one embodiment, photocrosslinking occurs due to exposure to electromagnetic radiation. Electromagnetic radiation includes ultraviolet light, visible light, X-ray, and gamma ray.

In various other embodiments, a limited selection of oligonucleotides using a SELEX method is followed by selection using a photoSELEX method. The initial SELEX selection rounds are conducted with oligonucleotides containing photoreactive groups. After a number of SELEX rounds, photoSELEX is conducted to select oligonucleotides capable of binding the target molecule.

In another embodiment, the production of an aptamer that includes a cleavable or releasable section (also described as an element or component) in the aptamer sequence is described. These additional components or elements are structural elements or components that introduce additional functionality into the aptamer and are thus functional elements or components. The aptamer is further produced with one or more of the following additional components (also described as a functional or structural element or component or moiety in any combination of these terms): a labeled or detectable component, a spacer component, and a specific binding tag or immobilization element or component.

As noted above, the present disclosure provides methods for identifying aptamers that bind target molecules and once bound have slow rates of dissociation or off-rates. The slow off-rates obtained with this method can exceed a half-life of about one hour and as much as about 240 minutes, that is, once a set of nucleic acid-target complexes is generated, half of the complexes in the set remain bound after one hour. Because the effect of a slow off-rate enrichment process depends upon the differing dissociation rates of aptamer affinity complexes, the duration of the slow off-rate enrichment process is chosen so as to retain a high proportion of aptamer affinity complexes with slow dissociation rates while substantially reducing the number of aptamer affinity complexes with fast dissociation rates. For example, incubating the mixture for relatively longer periods of time after imposing the slow off-rate enrichment process will select for aptamers with longer dissociation rates than aptamers selected using slow off-rate enrichment process having shorter incubation periods.

In various embodiments, the candidate mixture is mixed with a quantity of the target molecule and allowed to establish binding equilibrium with the target molecule. Prior to partitioning the target bound nucleic acids from those free in solution, a slow off-rate enrichment process is imposed to enrich the bound population for slow dissociation rates. As noted above, the slow off-rate enrichment process can be applied by the addition of a competitor molecule, by sample dilution, by a combination of sample dilution in the presence of a competitor molecule. Thus, in one embodiment, the slow off-rate enrichment process is applied by introducing competitor molecules into the mixture containing the nucleic acid-target complexes and incubating the mixture for some period of time before partitioning free from bound nucleic acids. The amount of competitor molecules is generally at least one order of magnitude higher than that of the nucleic acid molecules and may be two or more orders of magnitude higher. In another embodiment, the slow off-rate enrichment process is applied by diluting the sample mixture of nucleic acid-target complexes several fold (e.g. at least about one of 2×, 3×, 4×, 5×) in volume and incubating the mixture for some period of time before partitioning free from bound nucleic acids. The dilution volume is generally at least one order of magnitude higher, and may be about two or more orders of magnitude higher, than the original volume. In yet another embodiment, a combination of both competitor molecules and dilution is used to apply the slow off-rate enrichment process. In another embodiment, candidate mixtures that have been shown to result in an increased frequency of slow dissociation aptamers are used to select a number of candidate aptamers. These aptamers are screened to identify slow dissociation rate aptamers.

In another embodiment, a slow off-rate aptamer that includes a cleavable or releasable section in the fixed region of the aptamer is produced. The aptamer can also be produced with one or more of the following additional components: a labeled component, a spacer component, and a specific binding tag. Any or all of these elements may be introduced into a single stranded aptamer. In one embodiment, the element is introduced at the 5' end of the aptamer. In another embodiment, one or more of these elements is included by creating a partially double stranded aptamer, where one strand contains the various elements desired as well as a sequence complementary to one of the fixed sequence sections of the second strand containing the variable target binding region.

A "releasable" or "cleavable" element or moiety or component refers to a functional group where certain bonds in the functional group can be broken to produce 2 separate components. In various embodiments, the functional group can be cleaved by irradiating the functional group (photocleavable) at the appropriate wavelength or by treatment with the appropriate chemical or enzymatic reagents. In another embodiment, the releasable element may be a disulfide bond that can be treated with a reducing agent to disrupt the bond. The releasable element allows an aptamer/target affinity complex that is attached to a solid support to be separated from the solid support, such as by elution of the complex. The releasable element may be stable to the conditions of the rest of the assay and may be releasable under conditions that will not disrupt the aptamer/target complex.

As disclosed herein, an aptamer can further comprise a "tag" or "immobilization component or element" or "specific binding component or element" which refers to a component that provides a means for attaching or immobilizing an aptamer (and any target molecule that is bound to it) to a solid support. A "tag" is a set of copies of one type or species of component that is capable of associating with a probe. "Tags" refers to more than one such set of components. The tag can be attached to or included in the aptamer by any suitable method. Generally, the tag allows the aptamer to associate, either directly or indirectly, with a probe or receptor that is attached to the solid support. The probe may be highly specific in its interaction with the tag and retain that association during all subsequent processing steps or procedures. A tag can enable the localization of an aptamer affinity complex (or optional covalent aptamer affinity complex) to a spatially defined address on a solid support. Different tags, therefore, can enable the localization of different aptamer covalent complexes to different spatially defined addresses on a solid support. A tag can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, biotin, any fragment or derivative of these structures, any combination of the foregoing, or any other structure with which a probe (or linker molecule, as described below) can be designed or configured to bind or otherwise associate with specificity. Generally, a tag is configured such that it does not interact intramolecularly with either itself or the aptamer to which it is attached or of which it is a part. If SELEX is used to identify an aptamer, the tag may be added to the aptamer either pre- or post-SELEX. The tag is included on the 5'-end of the aptamer post-SELEX, or the tag is included on the 3'-end of the aptamer post-SELEX, or the tags may be included on both the 3' and 5' ends of the aptamers in a post-SELEX process.

Figure 8A:
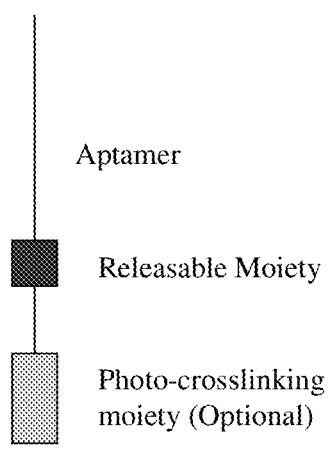
FIGS. 8A to 8D illustrate aptamer constructs that contain a variety of different and optional functionalities including immobilization tags, labels, photocrosslinking moieties, spacers, and releasable moieties.
Figure 8B:
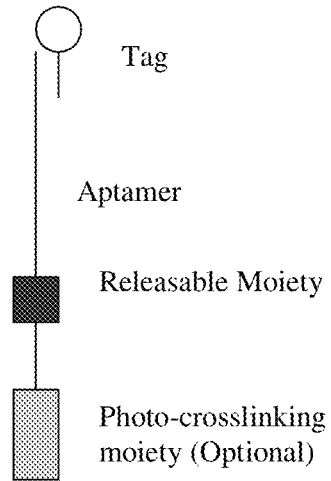
Figure 8C:
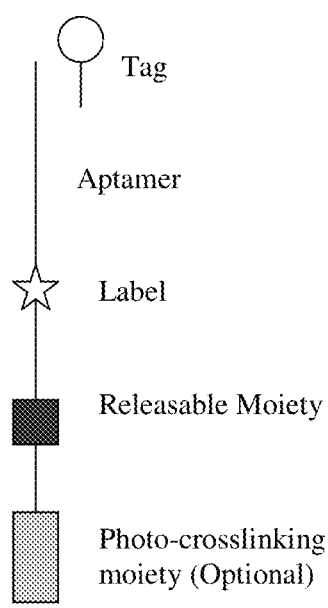
Figure 8D:
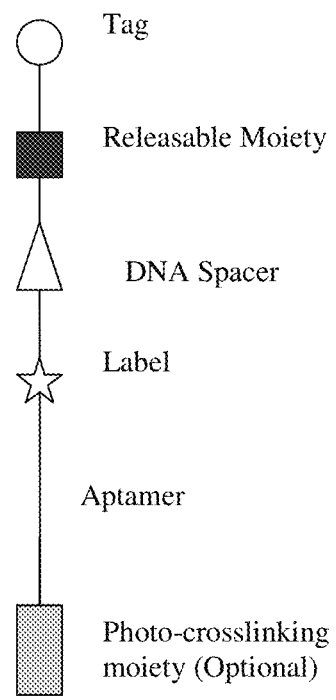
Figure 9A:
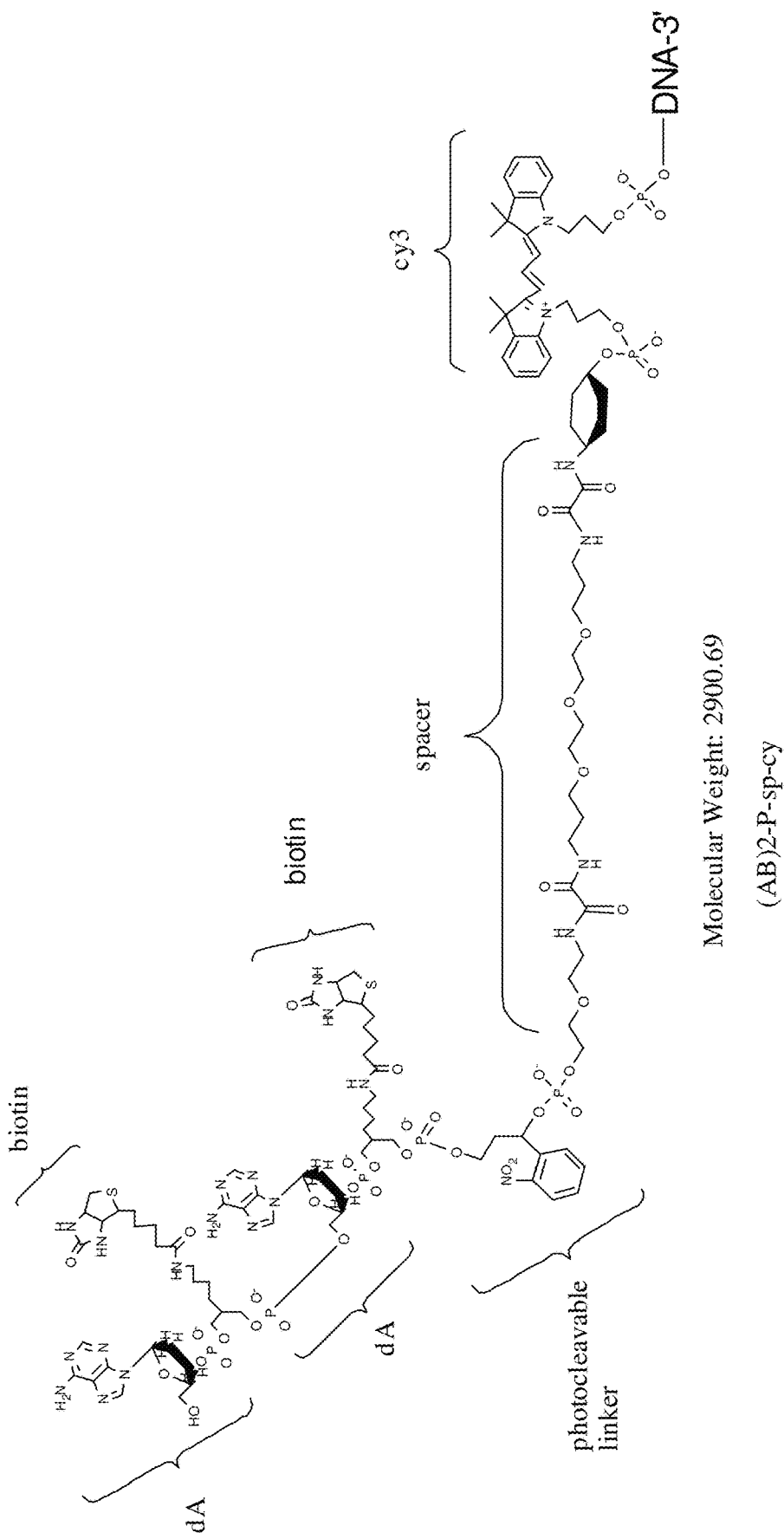
FIGS. 9A to 9F illustrate examples of aptamer constructs including a cleavable or releasable element, a tag (for example biotin), a spacer, and a label (for example Cy3).
Figure 9B:
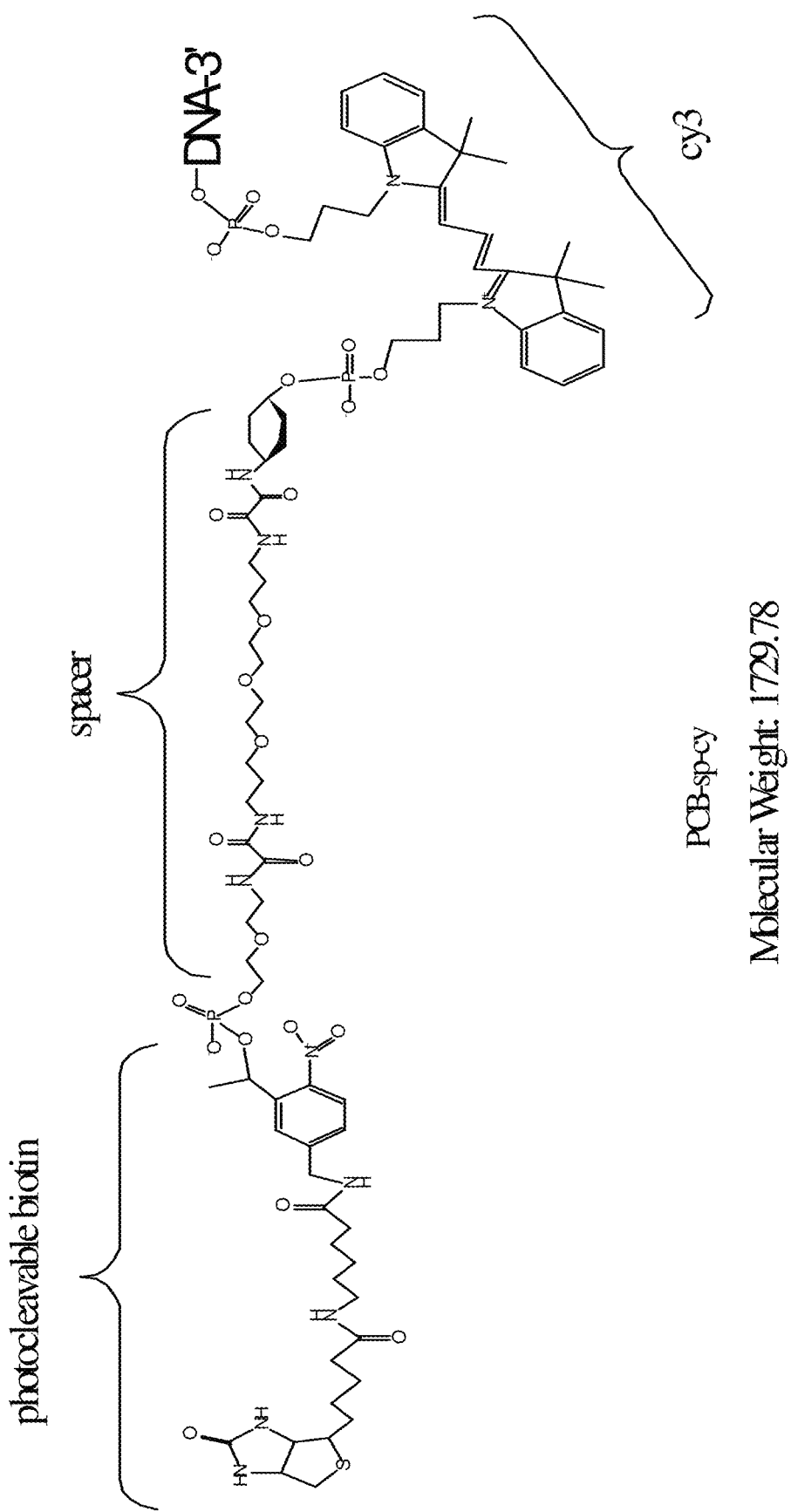
Figure 9C:
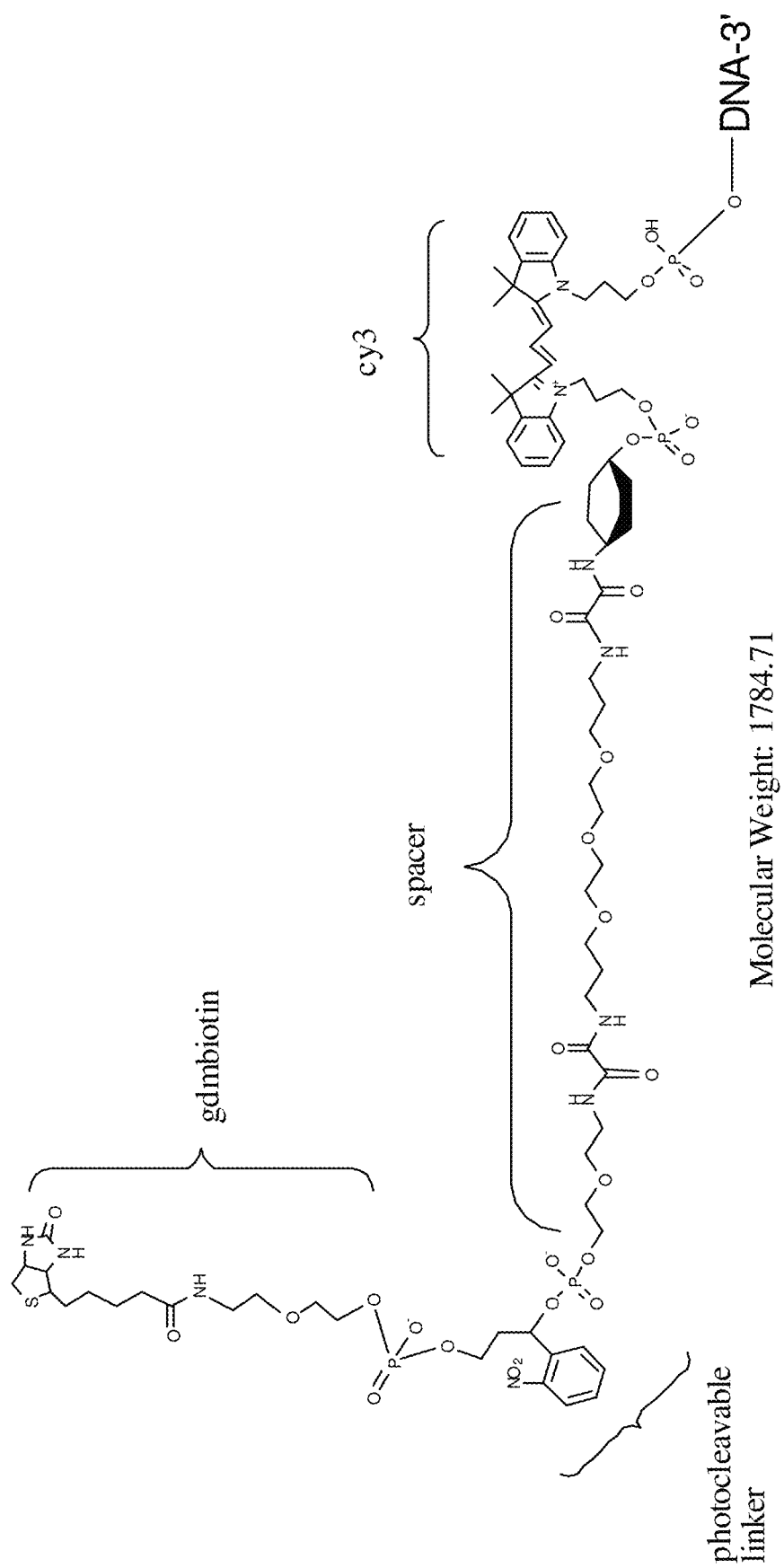
Figure 9D:
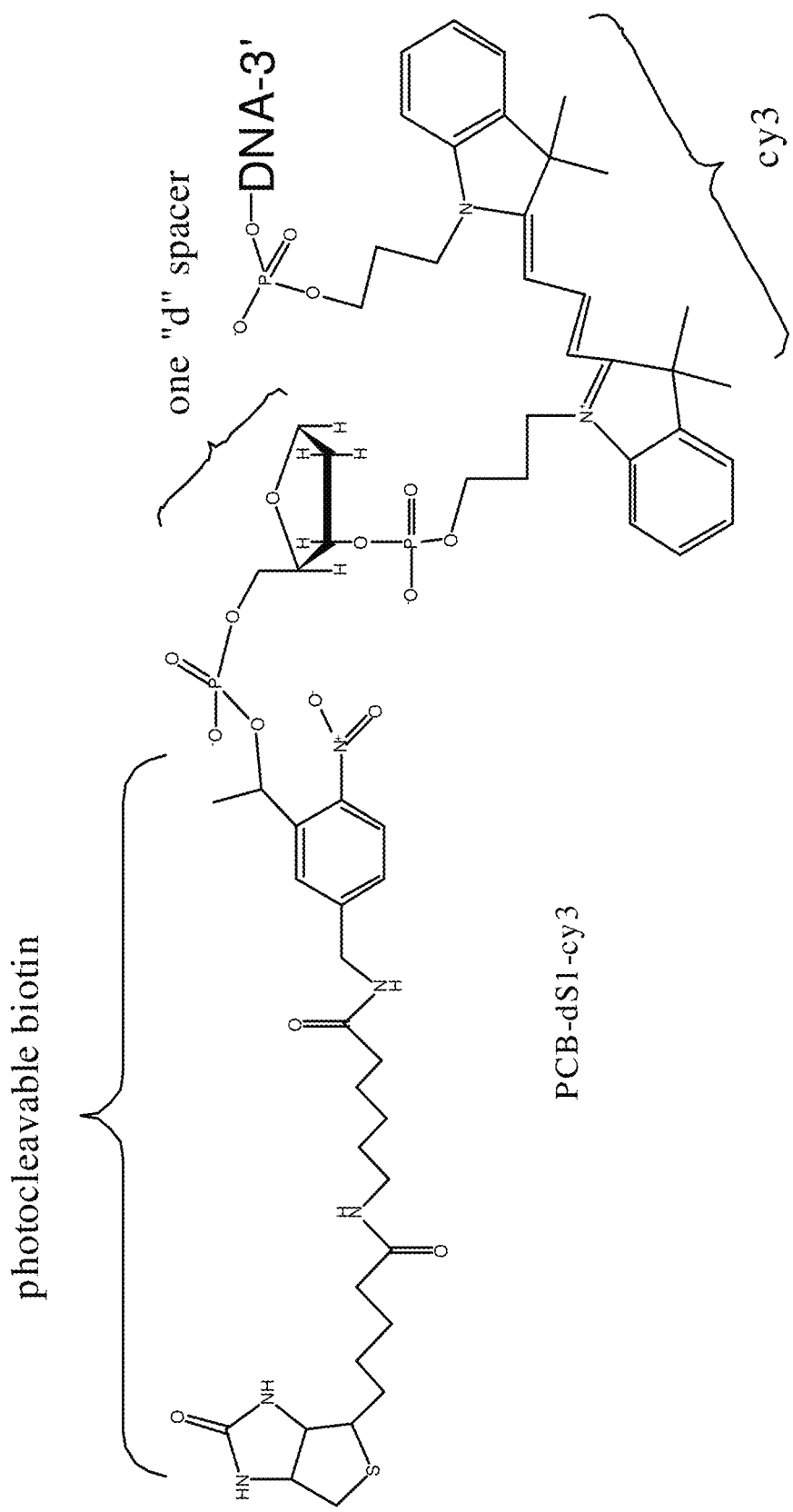
Figure 9E:
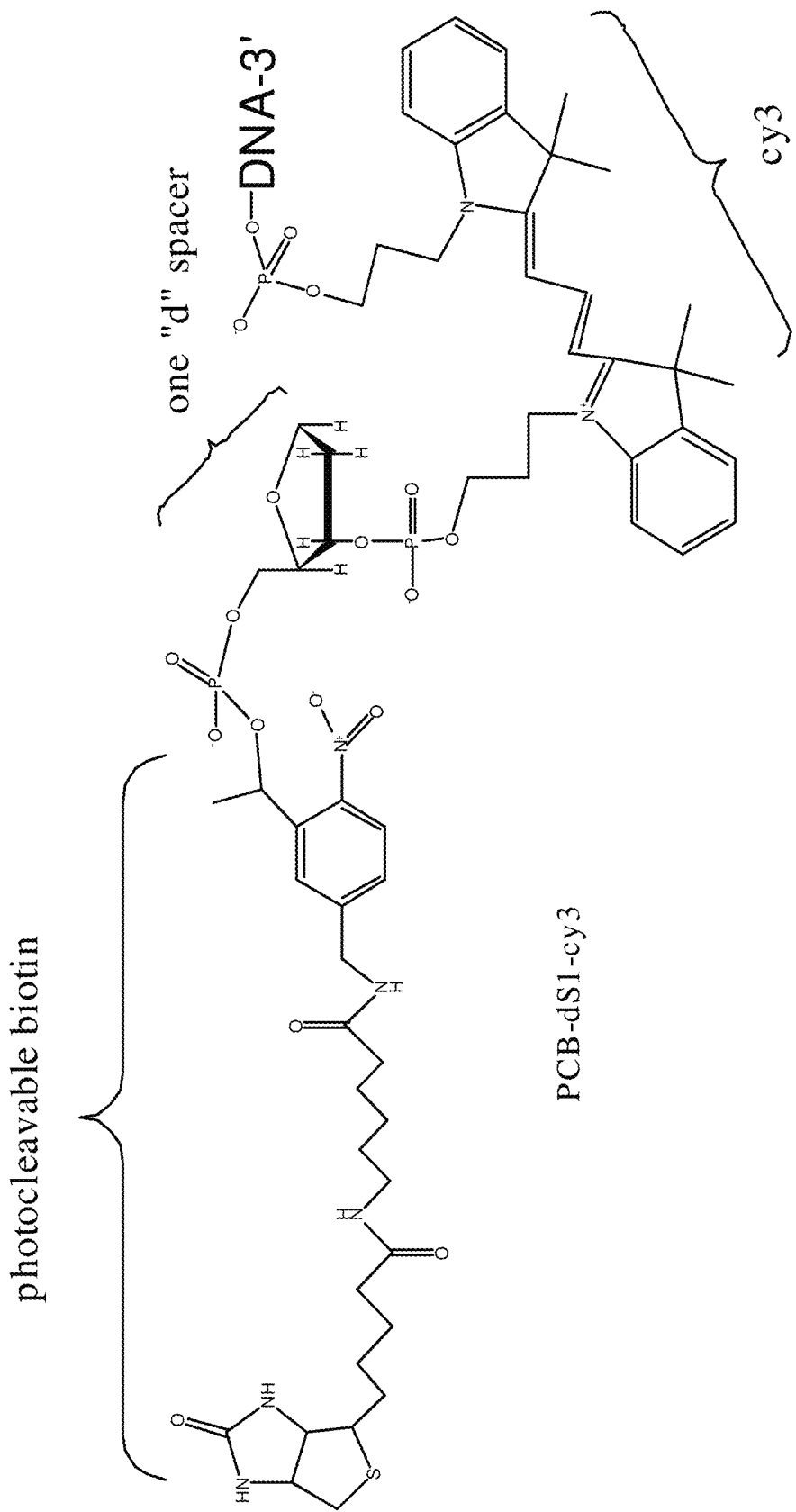
Figure 9F:
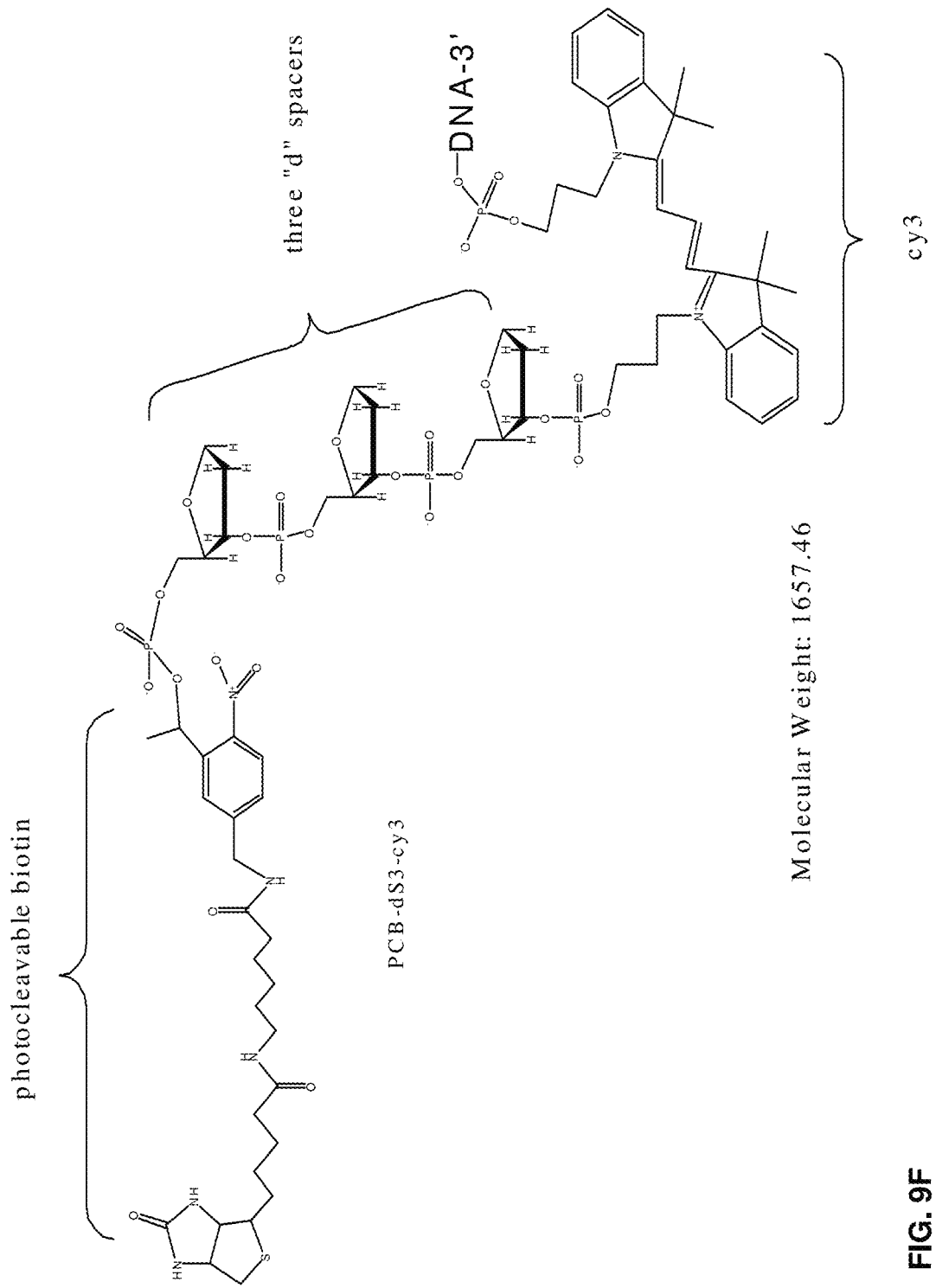

As illustrated in FIG. 8D, a fluorescent dye (such as Cy3), the photocleavable and biotin moieties are all added to the end of the aptamer. Because of potential interactions between the photocleavable moiety and the dye, a spacer is inserted between these two moieties. All constructs can be synthesized using standard phosphoramidite chemistry. Representative aptamer constructs are shown in FIG. 9A through FIG. 9F. The functionality can be split between the 5' and 3' end or combined on either end. In addition to photocleavable moieties, other cleavable moieties can be used, including chemically or enzymatically cleavable moieties. A variety of spacer moieties can be used and one or more biotin moieties can be included. Tags (also referred to as immobilization or specific binding elements or components) other than biotin can also be incorporated. Suitable construction reagents include biotin phosphoramidite, PC Linker (Glen Research PN 10-4920-02); PC biotin phosphoramidite (Glen Research PN 10-4950-02); dSpacer CE phosphoramidite (Glen Research PN 10-1914-02); Cy3 phosphoramidite (Glen Research PN 10-5913-02); and Arm26-Ach Spacer Amidite (Fidelity Systems PN SP26Ach-05).

In one embodiment, base modifications of the nucleotides are used in the production of the variable region of the aptamer. These modified nucleotides have been shown to produce aptamers that have very slow off-rates from their targets.

In the methods of the present disclosure the candidate mixture may comprise modified nucleic acids in which one, several (e.g. one of, or at least one of, 2, 3, 4, 5, 6, 7, 8, 9, 10, 11, 12, 13, 14, 15, 16, 17, 18, 19, 20, 21, 22, 23, 24, 25, 26, 27, 28, 29, 30) or all pyrimidines in at least one, or each, nucleic acid of the candidate mixture is chemically modified at the 5-position. Optionally, all C residues in the nucleic acids of the candidate mixture are chemically modified at the 5-position. Optionally, all T residues in the nucleic acids of the candidate mixture are chemically modified at the 5-position. Optionally, all U residues in the nucleic acids of the candidate mixture are chemically modified at the 5-position.

In another embodiment, the slow off-rate aptamers are mixed or exposed to a sample. The slow off-rate aptamer is allowed to react with, or bind to, its specific target in the sample to form a complex. A variety of methods may be used to detect either the target or the aptamer. The target may be detected in the complex or upon liberation from the complex. The aptamer may be detected in the complex or upon liberation from the complex. The aptamer/target complex may be used to isolate the specific target from other components in the test sample. Multiple aptamers may be used when a multiplexed assay for the detection of a variety of targets is desired.

Figure 3A:
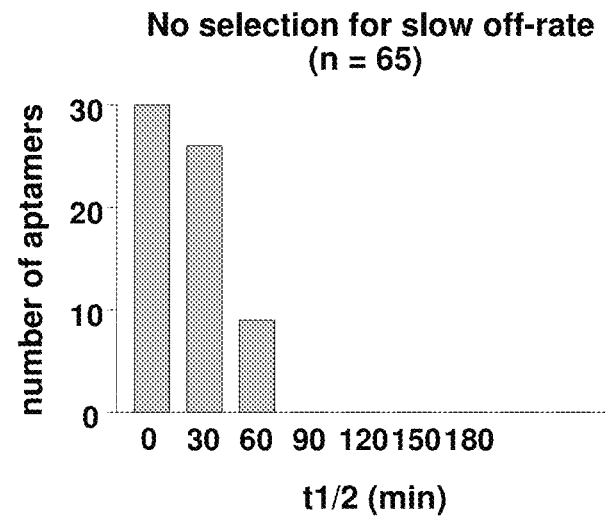
FIGS. 3A and 3B illustrate histograms of dissociation rate constants for affinity aptamers selected without (FIG. 3A) and with (FIG. 3B) a slow off-rate enrichment process as described in Example 2.

The method of the instant disclosure is illustrated generally in Examples 1-8. Example 1 describes the general affinity SELEX method using a candidate mixture comprised of modified nucleotides. Example 2 describes a photo SELEX method using a candidate mixture comprised of modified nucleotides and a 5'-terminal photoreactive group, and the improved SELEX method in which dilution is used to provide the slow off-rate enrichment process to the equilibrated aptamer:target mixture. Example 3 extends the method described in Example 2 by the addition of a competitor to the dilution step. Example 4 illustrates the effectiveness of the slow off-rate enrichment process. The average dissociation half-life value ($t_{1/2}$) for aptamers using the modified nucleotides 5-(N-benzylcarboxyamide)-dUTP (BndUTP), 5-(N-isobutylcarboxyamide)-dUTP (iBudUTP), or 5-(N-tryptaminocarboxyamide)-dUTP selected in the absence of a slow off-rate enrichment process was 20 minutes with some aptamers having a $t_{1/2}$ value of up to one hour (FIG. 3A). This is substantially longer than what has been previously described with natural bases or other modified nucleotides. The average for aptamers selected with a slow off-rate enrichment process was over 85 minutes. More specifically, with reference to FIG. 3B, it can be seen that introduction of a slow off-rate enrichment process produced aptamers with $t_{1/2}$ values of about ≥30 min., ≥about 60 min., ≥about 90 min., ≥about 120 min., ≥about 150 min., ≥about 180 min., ≥about 210 min., and ≥about 240 min. These dissociation rates for aptamer:target complexes are unprecedented.

Example 5 describes the generation of slow off-rate aptamers using a NapdU (5-(N-naphthylmethylcarboxyamide)-dUP) candidate mixture.

Example 6 describes the generation of a slow off-rate aptamer to a peptide target.

Example 7 illustrates the utility of slow off-rate aptamers relative to conventional aptamers.

Example 8 further illustrates the generation of slow off-rate aptamers using a BndU candidate mixture.

EXAMPLES

The following examples are provided for illustrative purposes only and are not intended to limit the scope of the invention as defined in the appended claims.

Example 1. Incorporation of Modified Nucleotides in Nucleic Acid Libraries Leads to Higher Affinity Enriched Libraries in Affinity SELEX A. Preparation of Candidate Mixtures Candidate mixtures were prepared with dATP, dGTP, 5-methyl-dCTP (MedCTP) and either dTTP or one of three dUTP analogs: 5-(N-benzylcarboxyamide)-dUTP (BndUTP), 5-(N-isobutylcarboxyamide)-dUTP (iBudUTP), or 5-(N-tryptaminocarboxyamide)-dUTP (TrpdUTP). Candidate mixtures were prepared by polymerase extension of a primer annealed to a biotinylated template (FIG. 2). For each candidate mixture composition, 4.8 nmol forward PCR primer and 4 nmol template were combined in 100 µL 1×KOD DNA Polymerase Buffer (Novagen), heated to 95° C. for 8 minutes, and cooled on ice. Each 100 µL primer: template mixture was added to a 400 µL extension reaction containing 1×KOD DNA Polymerase Buffer, 0.125 U/µL KOD XL DNA Polymerase, and 0.5 mM each dATP, MedCTP, dGTP, and dTTP or dUTP analog, and incubated at 70° C. for 30 minutes. Double-stranded product was captured via the template strand biotins by adding 1 mL streptavidin-coated magnetic beads (MagnaBind Streptavidin, Pierce, 5 mg/mL in 1M NaCl+0.05% TWEEN-20) and incubating at 25° C. for 10 minutes with mixing. Beads were washed three times with 0.75 mL SB1T Buffer (40 mM HEPES, pH 7.5, 125 mM NaCl, 5 mM KCl, 1 mM $MgCl_2$, 1 mM $CaCl_2$, 0.05% TWEEN-20). The aptamer strand was eluted from the beads with 1.2 mL 20 mM NaOH, neutralized with 0.3 mL 80 mM HCl, and buffered with 15 µL 1 M HEPES, pH 7.5. Candidate mixtures were concentrated with a Centricon-30 to approximately 0.2 mL, and quantified by UV absorbance spectroscopy.

B. Immobilization of Target Proteins

Target proteins were purchased with poly His tags, such as, $(His)_6$ tags (R&D Systems) and immobilized on $Co^{+2}$-NTA paramagnetic beads (MyOne TALON, Invitrogen, or hereinafter referred to as Talon beads). Target proteins were diluted to 0.2 mg/mL in 0.5 mL B/W Buffer (50 mM Na-phosphate, pH 8.0, 300 mM NaCl, 0.01% TWEEN-20), and added to 0.5 mL TALON beads (pre-washed three times with B/W Buffer and resuspended to 10 mg/mL in B/W Buffer). The mixture was rotated for 30 minutes at 25° C. and stored at 4° C. until use. TALON beads coated with $(His)_6$ peptide were also prepared and stored as above. Prior to use, beads were washed 3 times with B/W Buffer, once with SB1T, and resuspended in SB1T.

C. Aptamer Selection Scheme

Affinity selections were performed separately with each candidate mixture, comparing binding between target protein beads (signal, S) and $(His)_6$ beads (background, B). For each sample, a 0.5 µM candidate DNA mixture was prepared in 40 µL SB1T. 1 µL $(His)_6$-complement oligo (1 mM) (FIG. 2) was added to the DNA, along with 10 µL of a protein competitor mixture (0.1% HSA, 10 µM casein, and 10 µM prothrombin in SB1T).

Binding reactions were performed by adding 50 µL target protein-coated beads or $(His)_6$-coated beads (5 mg/mL in SB1T) to the DNA mixture and incubating 37° C. for 15 minutes with mixing. The DNA solution was removed and the beads were washed 5 times at 37° C. with SB1T containing 0.1 mg/mL herring sperm DNA (Sigma-Aldrich). Unless indicated, all washes were performed by re-suspending the beads in 100 µL wash solution, mixing for 30 seconds, separating the beads with a magnet, and removing the wash solution. Bound aptamers were eluted from the beads by adding 100 µL SB1T+2 M Guanidine-HCl and incubating at 37° C. for 5 minutes with mixing. The aptamer eluate was transferred to a new tube after magnetic separation. After the first two selection rounds, the final two of five target beads washes were done for 5 minutes instead of 30 seconds.

Primer beads were prepared by immobilizing biotinylated reverse PCR primer to streptavidin-coated paramagnetic beads (MyOne-Streptavidin C1 (SA beads), Invitrogen). 5 mL SA beads (10 mg/mL) were washed once with NaClT (5 M NaCl, 0.01% TWEEN-20), and resuspended in 5 mL biotinylated reverse PCR primer (5 µM in NaClT). The sample was incubated at 25° C. for 15 minutes, washed twice with 5 mL NaClT, resuspended in 12.5 mL NaClT (4 mg/mL), and stored at 4° C.

25 µL primer beads (4 mg/mL in NaClT) were added to the 100 µL aptamer solution in Guanidine Buffer and incubated at 50° C. for 15 minutes with mixing. The aptamer solution was removed, and the beads were washed 5 times with SB1T. Aptamer was eluted from the beads by adding 85 µL 20 mM NaOH, and incubating at 37° C. for 1 minute with mixing. 80 µL aptamer eluate was transferred to a new tube after magnetic separation, neutralized with 20 µL 80 mM HCl, and buffered with 1 µL 0.5M Tris-HCl, pH 7.5.

D. Aptamer Amplification and Purification

Selected aptamer DNA was amplified and quantified by QPCR. 48 µL DNA was added to 12 µL QPCR Mix (5×KOD DNA Polymerase Buffer, 25 mM $MgCl_2$, 10 µM forward PCR primer, 10 µM biotinylated reverse PCR primer, 5×SYBR Green I, 0.125 U/µL KOD XL DNA Polymerase, and 1 mM each dATP, dCTP, dGTP, and dTTP) and thermal cycled in an ABI5700 QPCR instrument with the following protocol: 1 cycle of 99.9° C., 15 seconds, 55° C., 10 seconds, 70° C., 30 minutes; 30 cycles of 99.9° C., 15 seconds, 72° C., 1 minute. Quantification was done with the instrument software and the number of copies of DNA selected with target beads and (His)$_6$ beads were compared to determine signal/background ratios.

Following amplification, the PCR product was captured on SA beads via the biotinylated antisense strand. 1.25 mL SA beads (10 mg/mL) were washed twice with 0.5 mL 20 mM NaOH, once with 0.5 mL SB1T, resuspended in 2.5 mL 3 M NaCl, and stored at 4° C. 25 µL SA beads (4 mg/mL in 3 M NaCl) were added to 50 µL double-stranded QPCR product and incubated at 25° C. for 5 minutes with mixing. The beads were washed once with SB1T, and the "sense" strand was eluted from the beads by adding 200 µL 20 mM NaOH, and incubating at 37° C. for 1 minute with mixing. The eluted strand was discarded and the beads were washed 3 times with SB1T and once with 16 mM NaCl.

Aptamer sense strand was prepared with the appropriate nucleotide composition by primer extension from the immobilized antisense strand. The beads were resuspended in 20 µL primer extension reaction mix (1× Primer Extension Buffer (120 mM Tris-HCl, pH 7.8 @ 20, 10 mM KCl, 7 mM MgSO$_4$, 6 mM (NH$_4$)$_2$SO$_4$, 0.001% BSA, and 0.01% Triton X100), 5 µM forward PCR primer, 0.125 U/µL KOD XL DNA Polymerase, 0.5 mM each dATP, MedCTP, dGTP, and either dTTP or dUTP analog) and incubated at 68° C. for 30 minutes with mixing. The beads were washed 3 times with SB1T, and the aptamer strand was eluted from the beads by adding 85 µL 20 mM NaOH, and incubating at 37° C. for 1 minute with mixing. 80 µL aptamer eluate was transferred to a new tube after magnetic separation, neutralized with 20 µL 80 mM HCl, and buffered with 5 µL 0.1 M HEPES, pH 7.5.

E. Selection Stringency and Feedback

The relative target protein concentration of the selection step was lowered each round in response to the S/B ratio as follows, where signal S and background B are defined in Section C above:

if $S/B<10, [P](i+1)=[P]i$ if $10 \leq S/B<100, [P](i+1)=[P]i/3.2$ if $S/B \geq 100, [P](i+1)[P]i/10$ where [P]=protein concentration and i=current round number.

Target protein concentration was lowered by adjusting the mass of target protein beads (and (His)$_6$ beads for background determination) added to the selection step.

After each selection round, the convergence state of the enriched DNA mixture was determined. 5 µL double-stranded QPCR product was diluted to 200 µL with 4 mM MgCl$_2$ containing 1×SYBR Green I. Samples were overlaid with 75 µL silicon oil and analyzed for convergence using a C$_0$t analysis which measures the hybridization time for complex mixtures of double stranded oligonucleotides. The sample was thermal cycled with the following protocol: 3 cycles of 98° C., 1 minute, 85° C., 1 minute; 1 cycle of 93° C., 1 minute, 85° C., 15 minutes. During the 15 minutes at 85° C., fluorescent images were measured at 5-second intervals. The fluorescence intensity was plotted as a function of log (time) to evaluate the diversity of the sequences.

F. Measurement of Equilibrium Binding Constant (Kd)

Equilibrium binding constants of the enriched libraries were measured using TALON bead partitioning. DNA was renatured by heating to 95° C. and slowly cooling to 37° C. Complexes were formed by mixing a low concentration of radiolabled DNA (~1×10$^{-11}$ M) with a range of concentrations of target protein (1×10$^{-7}$ M to 1×10$^{-12}$ M final) in SB1 Buffer, and incubating at 37° C. A portion of each reaction was transferred to a nylon membrane and dried to determine total counts in each reaction. A small amount of 5 mg/mL TALON beads was added to the remainder of each reaction and mixed at 37° C. for one minute. A portion was passed through a MultiScreen HV Plate (Millipore) under vacuum to separate protein-bound complexes from unbound DNA and washed with 100 µL SB1 Buffer. The nylon membranes and MultiScreen HV Plates were phosphorimaged and the amount of radioactivity in each sample quantified using a FUJI FLA-3000. The fraction of captured DNA was plotted as a function of protein concentration and a non-linear curve-fitting algorithm was used to extract equilibrium binding constants (K$_d$ values) from the data. Table 1 shows the K$_d$ values determined for each enriched candidate mixture to a set of targets. NT indicates that the enriched library for a particular base composition did not appear to have changed from the original candidate mixture, as determined by C$_0$t analysis, and was therefore Not Tested (NT).

Table 1 shows the equilibrium binding constants (K$_d$) for enriched pools to fifteen different protein targets and four different DNA libraries: naturally occurring bases (dT), 5-(N-benzylcarboxyamide) (BndU), 5-(N-isobutylcarboxyamide) (iBudU) or 5-(N-tryptaminocarboxyamide) (TrpdU). An aptamer with a K$_d$ of less than 1×10$^{-8}$ is desirable. The use of modified bases in the SELEX process produces a significantly higher percentage of desirable high affinity aptamers. It was observed that only 2 of the 14 aptamers produced with the normal nucleotides have the desired slow dissociation rates. Slow off-rate aptamers produced with the modified nucleotides were identified 9 of 14, 7 of 14, and 14 of 14 for BndUTP, iBudUTP, and TrpdUTP, respectively.

TABLE 1

Equilibrium binding constants (K$_d$) of the enriched libraries selected with different modified nucleotides, reported in units of molarity.

| Target Protein | dTTP | BndUTP | iBudUTP | TrpdUTP |
|---|---|---|---|---|
| 4-1BB | >1.0. × 10$^{-7}$ | 5.6. × 10$^{-9}$ | >1.0. × 10$^{-7}$ | 3.9. × 10$^{-9}$ |
| B7 | >1.0. × 10$^{-7}$ | 1.1. × 10$^{-8}$ | NT | 7.2. × 10$^{-9}$ |
| B7-2 | >1.0. × 10$^{-7}$ | NT | >1.0. × 10$^{-7}$ | 5.7. × 10$^{-9}$ |
| CTLA-4 | >1.0. × 10$^{-7}$ | NT | NT | 1.4. × 10$^{-9}$ |
| E-Selectin | >1.0. × 10$^{-7}$ | >1.0. × 10$^{-7}$ | >1.0. × 10$^{-7}$ | 1.9. × 10$^{-9}$ |
| Fractalkine | NT | >1.0. × 10$^{-7}$ | NT | 5.1. × 10$^{-11}$ |
| GA733-1 protein | 8.9. × 10$^{-9}$ | 2.8. × 10$^{-9}$ | 4.7. × 10$^{-9}$ | 4.5. × 10$^{-10}$ |
| Gp130 | >1.0. × 10$^{-7}$ | 5.9. × 10$^{-9}$ | 2.2. × 10$^{-8}$ | 1.2. × 10$^{-9}$ |
| HMG-1 | >1.0. × 10$^{-7}$ | NT | 2.2. × 10$^{-8}$ | 4.9. × 10$^{-9}$ |
| IR | >1.0. × 10$^{-7}$ | 1.9. × 10$^{-9}$ | 1.2. × 10$^{-8}$ | 2.2. × 10$^{-10}$ |
| OPG | 3.7. × 10$^{-8}$ | 4.6. × 10$^{-9}$ | 9.5. × 10$^{-9}$ | 1.7. × 10$^{-10}$ |
| PAI-1 | >1.0. × 10$^{-7}$ | 3.7. × 10$^{-10}$ | 9.1. × 10$^{-10}$ | 4.3. × 10$^{-9}$ |
| P-Cadherin | >1.0. × 10$^{-7}$ | 3.5. × 10$^{-9}$ | 5.2. × 10$^{-9}$ | 2.7. × 10$^{-9}$ |
| sLeptin R | >1.0. × 10$^{-7}$ | 2.3. × 10$^{-9}$ | NT | 4.6. × 10$^{-10}$ |

NT = not tested.

Figure 5:
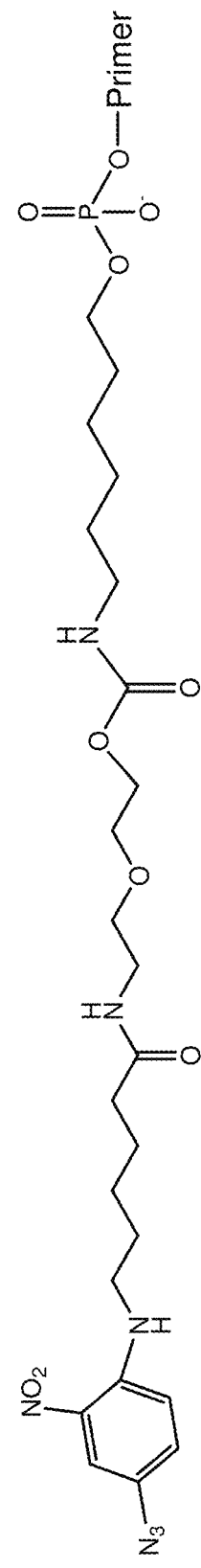
FIG. 5 illustrates chemical structures of the chromophores coupled to the 5' terminus of the forward primer as illustrated in FIGS. 4A and 4B.

Example 2. Generation of PhotoAptamers Using 5'-Fixed PhotoSELEX and Slow Off-Rate Enrichment Process by Dilution A. Preparation of Candidate Mixtures Candidate mixtures containing dATP, dCTP, dGTP, and BndUTP were prepared by polymerase extension of a primer annealed to a biotinylated template (FIG. 4A-B). For each template, four different forward primers were used, each possessing a unique chromophore at the 5' terminus (see FIG. 5 for the chromophore structures). For each candidate mixture, 11 nmol forward primer (with 5' chromophore) and 10 nmol template were combined in 250 µL Primer Extension Buffer (120 mM Tris-HCl, pH 7.8, 10 mM KCl, 6 mM $(NH_4)_2SO_4$, 7 mM $MgSO_4$, 0.1 mg/mL BSA, 0.1% Triton X-100), heated to 95° C. for 5 minutes, and cooled on ice. 125 µL each primer:template mixture was added to a 1 mL extension reaction containing Primer Extension Buffer, 0.125 U/µL KOD XL DNA Polymerase, and 0.5 mM each dATP, dCTP, dGTP, and BndUTP, and incubated at 70° C. for 30 minutes. Each 1 mL reaction was split into four 250 µL aliquots and chilled on ice. Double-stranded product was captured via the template strand biotins by adding 1 mL streptavidin-coated magnetic beads (MagnaBind-Streptavidin, Pierce, 5 mg/mL in 1M NaCl+0.05% TWEEN-20) to each 250 µL aliquot and incubating at 25° C. for 60 minutes with mixing. Beads were washed three times with 0.5 mL SB17T Buffer (40 mM HEPES, pH 7.5, 125 mM NaCl, 5 mM KCl, 5 mM $MgCl_2$, 1 mM EDTA, 0.05% TWEEN-20). The aptamer strand was eluted from the beads with 1 mL 20 mM NaOH, neutralized with 0.25 mL 80 mM HCl, and buffered with 10 µL 1 M HEPES, pH 7.5. Candidate mixtures were concentrated with a Centricon-30 to approximately 0.2 mL, and quantified by UV absorbance spectroscopy.

B. Preparation of Target Proteins

Untagged target proteins were biotinylated by covalent coupling of NHS-PEO4-biotin (Pierce) to lysines residues. Proteins (300 pmol in 50 µL) were exchanged into SB17T with a Sephadex G-25 microspin column. NHS-PEO4-biotin was added to 1.5 mM and the reaction was incubated at 4° C. for 16 hours. Unreacted NHS-PEO4-biotin was removed with a Sephadex G-25 microspin column.

C. Aptamer Selection with Slow Off-Rate Enrichment Process and Photocrosslinking Selections were performed separately with each candidate mixture, comparing binding between samples with target protein (signal S) and samples without target protein (background B). The first three rounds were performed with selection for affinity (no photocrosslinking); the second and third included slow off-rate enrichment process. Rounds four through eight included both slow off-rate enrichment process and photocrosslinking.

For each sample, a 90 µL DNA mixture was prepared in SB17T with 10-20 pmoles candidate mixture (100 pmoles in the first round) and 100 pmoles reverse primer. Samples were heated to 95° C. for 3 minutes and cooled to 37° C. at a rate of 0.1 C/second. Samples were combined with 10 µL protein competitor mixture (0.1% HSA, 10 µM casein, and 10 µM prothrombin in SB17T), added to 0.5 mg SA beads (pre-washed twice with 20 mM NaOH and once with SB17T), and incubated at 37° C. for 5 minutes with mixing. Beads were removed by magnetic separation.

Binding reactions were performed by adding 10 µL target protein (0.5 µM in SB17T) or SB17T to 40 µL DNA mixture and incubating at 37° C. for 30 minutes.

When slow off-rate enrichment process was employed, samples were diluted 20× by adding 950 µL SB17T (pre-heated to 37° C.), and incubated at 37° C. for 30 minutes prior to capturing complexes.

Complexes were captured on SA beads via protein biotins by adding 0.25 mg MyOne-SA beads (Invitrogen) and incubating at 37° C. for 15 minutes with mixing. Free DNA was removed by washing the beads five times with SB17T. Unless indicated, all washes were performed by resuspending the beads in 100 µL wash solution, mixing for 30 seconds at 25° C., separating the beads with a magnet, and removing the wash solution. The aptamer strand was eluted from the beads by adding 85 µL 20 mM NaOH, and incubating at 37° C. for 1 minute with mixing. 80 µL aptamer eluate was transferred to a new tube after magnetic separation, neutralized with 20 µL 80 mM HCl, and buffered with 1 µL 0.5 M Tris-HCl, pH 7.5.

When photo-selection was employed, the 50 µL binding reactions, (or 1 mL binding reactions after optional slow off-rate enrichment process by dilution) were irradiated from above with a high-pressure mercury lamp (Optical Associates, Inc. model 0131-0003-01, 500 W, with 310 nm mirror set). Candidate mixtures possessing a BrdU chromophore were irradiated for 37 seconds, those possessing an ANA chromophore were irradiated for 60 seconds, and those possessing an AQ or psoralen chromophore were irradiated for 10 minutes. An additional filter (5 mm plate glass) was used for the ANA, AQ and psoralen chromophores to eliminate unnecessary, but potentially damaging wavelengths below 320 nm. Complexes were captured as above, and non-crosslinked DNA was removed by washing the beads once with 4 M guanidine-HCl+0.05% TWEEN-20 at 50° C. for 10 minutes, once with 20 mM NaOH at 25° C. for 2 minutes, twice with SB17T, and once with 16 mM NaCl. Crosslinked DNA was not removed from the bead surface for the amplification steps.

D. Aptamer Amplification and Purification

Selected aptamer DNA was amplified and quantified by QPCR. 48 µL DNA was added to 12 µL QPCR Mix (5×KOD DNA Polymerase Buffer, 25 mM $MgCl_2$, 10 µM forward PCR primer, 10 µM biotinylated reverse PCR primer, 5×SYBR Green I, 0.125 U/µL KOD XL DNA Polymerase, and 1 mM each dATP, dCTP, dGTP, and dTTP) and thermal cycled in an a Bio-Rad MyIQ QPCR instrument with the following protocol: 1 cycle of 99.9° C., 15 sec, 55° C., 10 sec, 68° C., 30 min, 30 cycles of 99.9° C., 15 seconds, 72° C., 1 minute. Quantification was done with the instrument software and the number of copies of DNA selected with and without target protein were compared to determine signal/background ratios.

When photo-selection was employed, a cDNA copy of the selected DNA was prepared by primer extension on the bead surface. Washed beads were resuspended in 20 µL cDNA extension mix (Primer Extension Buffer containing 5 µM reverse PCR primer, 0.5 mM each dATP, dCTP, dGTP, and dTTP, and 0.125 U/µL KOD XL DNA Polymerase) and incubated at 68° C. for 30 minutes with mixing. The beads were washed 3 times with SB17T, and the aptamer strand was eluted by from the beads by adding 85 µL 20 mM NaOH, and incubating at 37° C. for 1 minute with mixing. 80 µL aptamer eluate was transferred to a new tube after magnetic separation, neutralized with 20 µL 80 mM HCl, and buffered with 1 µL 0.5 M Tris-HCl, pH 7.5. The cDNA was amplified and quantified by QPCR as above for the 30 cycles of 99.9° C., 15 seconds, 72° C., 1 minute.

Following amplification, the PCR product was captured on SA beads via the biotinylated antisense strand. 1.25 mL SA beads (10 mg/mL) were washed twice with 0.5 mL 20 mM NaOH, once with 0.5 mL SB17T, resuspended in 1.25 mL 3 M NaCl+0.05% Tween, and stored at 4° C. 25 µL SA beads (10 mg/mL in 3 M NaClT) were added to 50 µL double-stranded QPCR product and incubated at 25° C. for 5 minutes with mixing. The beads were washed once with SB17T, and the "sense" strand was eluted from the beads by adding 200 µL 20 mM NaOH, and incubating at 37° C. for 1 minute with mixing. The eluted strand was discarded and the beads were washed 3 times with SB17T and once with 16 mM NaCl.

Aptamer sense strand was prepared with the appropriate chromophore by primer extension from the immobilized antisense strand. The beads were resuspended in 20 µL primer extension reaction mixture (1× Primer Extension Buffer, 1.5 mM MgCl$_2$, 5 µM forward primer with appropriate 5' chromophore, 0.5 mM each dATP, dCTP, dGTP, and BndUTP, and 0.125 U/µL KOD XL DNA Polymerase) and incubated at 68° C. for 30 minutes with mixing. The beads were washed 3 times with SB17T, and the aptamer strand was eluted from the beads by adding 85 µL 20 mM NaOH, and incubating at 37° C. for 1 minute with mixing. 80 µL aptamer eluate was transferred to a new tube after magnetic separation, neutralized with 20 µL 80 mM HCl, and buffered with 5 µL 0.1 M HEPES, pH 7.5.

E. Selection Stringency and Feedback

Target protein was adjusted at each round as described in Example 1. After each round of selection, the convergence state of the enriched pool was determined as described in Example 1.

F. Equilibrium Binding Constants of Enriched Libraries

The binding affinity was determined as described in Example 1 above, but with SA capture beads. The following table, Table 2, summarizes the equilibrium binding constants (K$_d$) obtained using the photoSELEX protocol with slow off-rate enrichment process.

TABLE 2

Equilibrium binding constants (K$_d$) of the enriched libraries selected with different chromophores, reported in units of molarity. Measurements were not made on libraries that failed to converge (indicated with an x).

| Target Protein | BrdU | AQ | ANA | Psor |
|---|---|---|---|---|
| β-catenin | 2.7. × 10$^{-8}$ | 3.6. × 10$^{-9}$ | 1.1 × 10$^{-9}$ | 1.6. × 10$^{-9}$ |
| bFGF | 3.1. × 10$^{-8}$ | 5.7. × 10$^{-10}$ | 7.1. × 10$^{-10}$ | 5.1. × 10$^{-10}$ |
| CMP-SAS | x | 6.2. × 10$^{-9}$ | 7.3. × 10$^{-9}$ | 4.9. × 10$^{-8}$ |
| endostatin | 1.3. × 10$^{-9}$ | 8.7. × 10$^{-10}$ | 8.8. × 10$^{-10}$ | 1.3. × 10$^{-9}$ |
| IL-6 | 1.0. × 10$^{-9}$ | 5.4. × 10$^{-10}$ | 4.0. × 10$^{-10}$ | x |
| myeloperoxidase | 6.0. × 10$^{-10}$ | 2.8. × 10$^{-10}$ | 5.0. × 10$^{-10}$ | 1.5. × 10$^{-10}$ |
| SDF-1β | 8.1. × 10$^{-10}$ | 5.7. × 10$^{-10}$ | 3.8. × 10$^{-10}$ | x |
| TIMP-1 | 5.2. × 10$^{-9}$ | 7.3. × 10$^{-9}$ | 8.9. × 10$^{-9}$ | x |
| VEGF | 7.2. × 10$^{-10}$ | 4.2. × 10$^{-9}$ | 5.5. × 10$^{-10}$ | x |
| vWF | 2.6. × 10$^{-8}$ | 8.8. × 10$^{-9}$ | 8.1. × 10$^{-9}$ | x |

G. Crosslink Activity Assay

Figure 6:
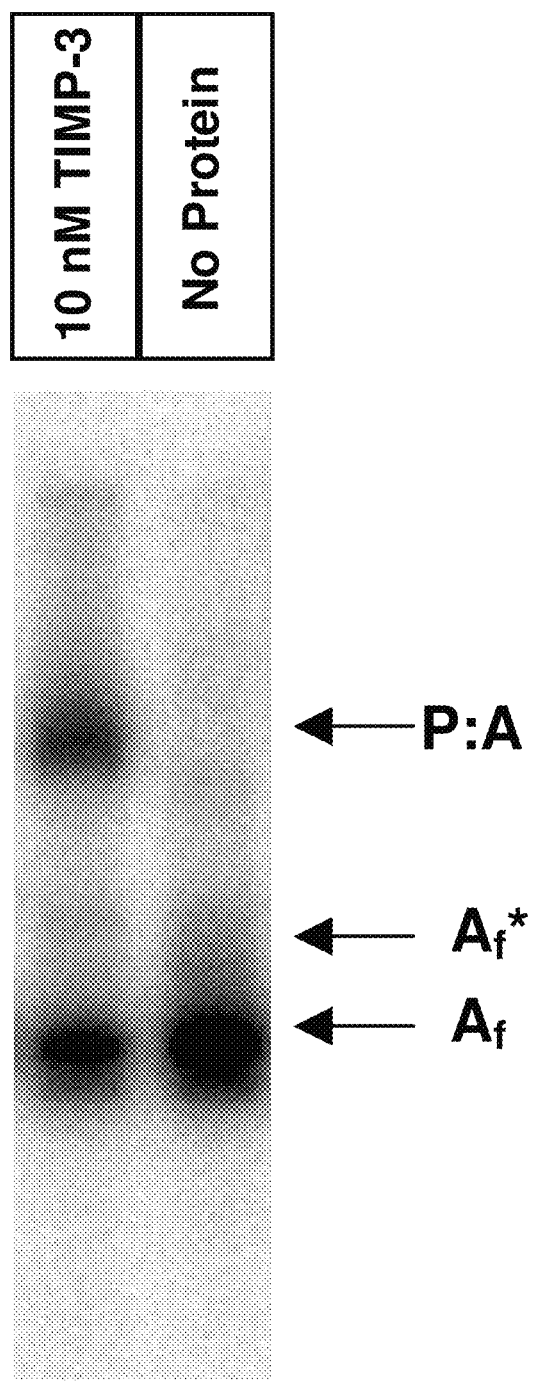
FIG. 6 illustrates a PAGE analysis of crosslink activity of TIMP-3 5'ANA/BndU enriched library using 5'-Fixed PhotoSELEX described in Example 3. The gel illustrates the separation of free aptamer ($A_f$), intramolecular crosslinked aptamer ($A_f^*$), and crosslinked protein:aptamer complexes (P:A).

The crosslink yield of enriched libraries was determined by measuring the percent of DNA crosslinked to protein under conditions of saturating protein and light. Radiolabeled DNA (50 pM) was mixed with reverse primer (16 nM) in SB17T, heated to 95° C. for 3 minutes, and cooled to 37° C. at 0.1° C./second. Target protein was added to the DNA mix to a final concentration of 10 nM and incubated at 37° C. for 30 minutes. Control samples with no protein were simultaneously prepared. Samples were crosslinked with the chromophore-specific conditions described above, but with a saturating dose (6 minutes for BrdU, 10 minutes for ANA, and 30 minutes for AQ and Psor). Samples were analyzed by denaturing PAGE, FIG. 6, and quantified and the results are tabulated in Table 3.

TABLE 3

Crosslink yields of the enriched libraries selected with different chromophores, reported in units of percent of total DNA crosslinked to protein. Measurements were not made on libraries that failed to converge (indicated with an x).

| Target Protein | BrdU | AQ | ANA | Psor |
|---|---|---|---|---|
| β-catenin | 15 | 9 | 8 | 1 |
| bFGF | 4 | 9 | 15 | 4 |
| CMP-SAS | x | 3 | 5 | 2 |

TABLE 3-continued

Crosslink yields of the enriched libraries selected with different chromophores, reported in units of percent of total DNA crosslinked to protein. Measurements were not made on libraries that failed to converge (indicated with an x).

| Target Protein | BrdU | AQ | ANA | Psor |
|---|---|---|---|---|
| Endostatin | 2 | 1 | 18 | 3 |
| IL-6 | 0 | 5 | 9 | |
| Myeloperoxidase | 4 | 13 | 9 | 8 |
| SDF-1β | 8 | 10 | 17 | x |
| TIMP-1 | 1 | 4 | 2 | x |
| VEGF | 1 | 1 | 4 | x |
| vWF | 2 | 2 | 7 | x |

Example 3. Generation of Slow Off-Rate Aptamers Using a Slow Off-Rate Enrichment Process with a Competitor A. Preparation of Candidate Mixtures Candidate mixtures containing dATP, dCTP, dGTP, and BndUTP were prepared by polymerase extension of a primer annealed to a biotinylated template for 94 protein targets. 55 nmol forward primer (with 5' ANA chromophore) and 55 nmol template were combined in 0.5 mL Primer Extension Buffer (120 mM Tris-HCl, pH 7.8, 10 mM KCl, 6 mM (NH$_4$)$_2$SO$_4$, 7 mM MgSO$_4$, 0.1 mg/mL BSA, 0.1% Triton X-100), heated to 95° C. for 5 minutes, 70° C. for 5 minutes, 48° C. for 5 minutes, and cooled on ice. The primer:template mixture was added to a 5.5 mL extension reaction containing Primer Extension Buffer, 0.125 U/µL KOD XL DNA Polymerase, and 0.5 mM each dATP, dCTP, dGTP, and BndUTP, and incubated at 70° C. for 60 minutes. After completion of the extension reaction, the solution was chilled on ice. Double-stranded product was captured via the template strand biotins by adding 25 mL streptavidin-coated magnetic beads (MagnaBind-Streptavidin, Pierce, 5 mg/mL in 1 M NaCl+0.05% TWEEN-20) to the primer extension product and incubating 25° C. for 15 minutes with rotating. Beads were washed three times with 40 mL SB17T Buffer (40 mM HEPES, pH 7.5, 125 mM NaCl, 5 mM KCl, 5 mM MgCl$_2$, 1 mM EDTA, 0.05% TWEEN-20). The aptamer strand was eluted from the beads with 35.2 mL 20 mM NaOH for 5 minutes with shaking. The eluted strand was neutralized with 8.8 mL 80 mM HCl, and buffered with 400 µL 1 M HEPES, pH 7.3. Candidate mixtures were concentrated with a Centricon-30 to approximately 0.7 mL, and quantified by UV absorbance spectroscopy.

B. Preparation of Target Proteins

Untagged target proteins were biotinylated as described in Example 2.

C. Aptamer Selection with Slow Off-Rate Enrichment Process and Photocrosslinking Selections were performed separately as described in Example 2, with the addition of 10 mM dextran sulfate as a competitor for aptamer rebinding during the slow off-rate enrichment process in rounds six through nine.

The slow off-rate enrichment process was employed in three different ways. In rounds two and three, samples were diluted 20× by adding 950 µL SB17T (preheated to 37° C.), and incubated at 37° C. for 30 minutes prior to capturing complexes. In rounds four and five, samples were diluted 20× by adding 950 µL SB17T (preheated to 37° C.), and incubated at 37° C. for 30 minutes prior to crosslinking. In rounds six and seven, samples were diluted 20× by adding 950 µL SB17T (preheated to 37° C.). 50 µL of each diluted sample was diluted again by transferring to 950 μL SB17T+ 10 mM 5000K dextran sulfate (preheated to 37° C.) to give an overall 400× dilution, and incubated at 37° C. for 60 minutes prior to crosslinking. In rounds eight and nine, samples were diluted 20× by adding 950 μL SB17T (preheated to 37° C.), and 50 μL of each sample was diluted again by transferring to 950 μL SB17T (preheated to 37° C.) to give 400× dilution. Finally, 50 μL of each 400× diluted sample was diluted again by transferring to 950 μL SB17T+ 10 mM 5000K dextran sulfate (preheated to 37° C.) to give an overall 8000× dilution, and incubated at 37° C. for 60 minutes prior to crosslinking. Complexes were captured and washed as described in Example 2. When photo-crosslinking was employed, the 1 mL binding reactions after the slow off-rate enrichment process were irradiated from above with an array of 470 nm LEDs for 60 seconds prior to complex capture as in Example 2.

D. Aptamer Amplification and Purification

Amplification and purification were performed as in Example 2.

E. Selection Stringency and Feedback

Target protein was adjusted at each round as described in Example 1, except in rounds six and eight. In order to maximize signal after these large dilutions, the target protein was increased to 100 nM for rounds six and eight. After each round of selection, the convergence state of the enriched pool was determined as described in Example 1.

F. Dissociation Rate Constant Determination Protocol.

The rate constant for aptamer:protein complex dissociation (koff) was determined for each aptamer by measuring the fraction of pre-formed aptamer:protein complexes that remain bound after dilution as a function of time. Radiolabeled aptamer (50 pM) was equilibrated in SB17T-0.002 (SB17T with TWEEN-20 reduced to 0.002%) at 37° C. with protein at a concentration 10× greater than the measured $K_d$ value. Samples were diluted 100× with SB17T-0.002 at 37° C. and aliquots were removed at various time points and partitioned to separate free aptamer from protein:aptamer complexes. Partitioning was accomplished by adding ZORBAX resin (Agilent) to the sample, capturing complexes on the resin, passing the sample through a DuraPore membrane under vacuum, and washing the resin with SB17T-0.002. For proteins not efficiently captured with ZORBAX resin, the assay was performed with biotinylated protein in SB17T and partitioning was accomplished by capturing complexes with SA beads. The amount of complex remaining at each time point was determined by quantifying the radiolabeled aptamer on the resin with a FUJI FLA-3000 phosphorimager. The fraction of complex was plotted as a function of time and the dissociation rate constant (koff) and dissociation half-life value ($t_{1/2}$) was determined by fitting the data to an analytic expression for bimolecular dissociation kinetics using non-linear regression.

G. Kinetic Properties of Some Aptamers

The following table, Table 4, summarizes the dissociation half-life values ($t_{1/2}$) obtained for aptamers selected against 10 targets using this protocol.

TABLE 4

Dissociation half-life values ($t_{1/2}$) of aptamers using the competitor slow off-rate enrichment step protocol.

| Target Protein | $t_{1/2}$ (min) |
| --- | --- |
| bFGF R | 66 |
| C3 | 164 |
| catalase | 58 |

TABLE 4-continued

Dissociation half-life values ($t_{1/2}$) of aptamers using the competitor slow off-rate enrichment step protocol.

| Target Protein | $t_{1/2}$ (min) |
| --- | --- |
| FGF-17 | 91 |
| group IB phospholipase A2 | 40 |
| HB-EGF | 49 |
| HCC-4 | 143 |
| IL-6 sRα | 114 |
| SAP | 186 |

Figure 3B:
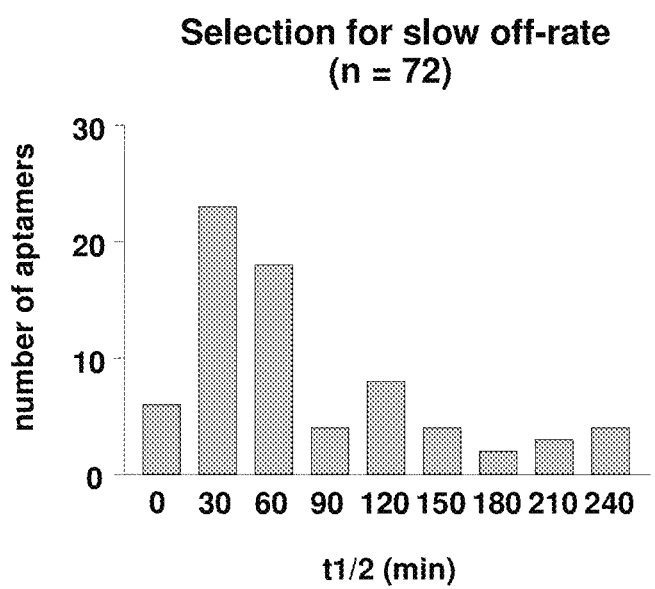

Example 4. The Slow Off-Rate Enrichment Process Increases the Dissociation Half-Life of Selected Aptamers Dissociation half-life values ($t_{1/2}$) were measured and plotted for 65 aptamers that were selected by either the affinity SELEX method described in Example 1 or photo SELEX methods described in U.S. Pat. No. 6,458,539, entitled "Photoselection of Nucleic Acid Ligands" without a slow off-rate enrichment process (FIG. 3A). $t_{1/2}$ values were also measured and plotted for 72 aptamers that were selected by the slow off-rate enrichment process described in Example 2 with a slow off-rate enrichment process by dilution or dilution with competitor (FIG. 3B). The average $t_{1/2}$ value for aptamers using the modified nucleotides 5-(N-benzylcarboxyamide)-dUTP (BndUTP), 5-(N-isobutylcarboxyamide)-dUTP (iBudUTP), or 5-(N-tryptaminocarboxyamide)-dUTP (TrpdUTP) selected in the absence of a slow off-rate enrichment process was 20 minutes with some aptamers having a $t_{1/2}$ value of up to one hour. This is substantially longer than what has been previously described with natural bases or other modified nucleotides. The average for aptamers selected with a slow off-rate enrichment process was over 85 minutes, with some aptamers having a $t_{1/2}$ value in excess of four hours.

Example 5. Generation of Aptamers from a NapdU Random Library

A. Preparation of Candidate Mixtures

Candidate mixtures containing dATP, dCTP, dGTP, and NapdUTP were prepared as described in Example 3 but without the 5'-ANA photoreactive group.

B. Immobilization of Target Proteins

Target proteins contained a (His)$_6$ tag and were captured with Talon beads as described in Example 1.

C. Aptamer Selection with Slow Off-Rate Enrichment Process

Aptamer selection was performed as described in Example 3, but without photocrosslinking.

D. Aptamer Amplification and Purification

Amplification and purification were performed as described in Example 3.

E. Selection Stringency and Feedback

Selection stringency and feedback were performed as described in Example 3.

F. Aptamer Properties

The equilibrium binding constant ($K_d$) of four aptamers from this selection are listed in Table 5.

TABLE 5

Equilibrium binding constants (Kd) of NapdUTP aptamers.

| Target Protein | $K_d$ (M) |
|---|---|
| bFGF | $1.1. \times 10^{-9}$ |
| Endostatin | $2.0. \times 10^{-10}$ |
| TIMP-3 | $1.5. \times 10^{-10}$ |
| VEGF | $7.2. \times 10^{-10}$ |

Example 6. Generation of Slow—Off-Rate Aptamers for a Peptide Target Using a Slow Off-Rate Enrichment Process with a Competitor A. Preparation of Candidate Mixtures Candidate mixtures containing dATP, dCTP, dGTP, and BndUTP were prepared by polymerase extension of a primer with a 5' ANA chromophore and purified as described in Example 3.

B. Aptamer Selection with Slow Off-Rate Enrichment Process and Photocrosslinking Aptamer selection was performed as described in Example 3 with the 29 amino acid biotinylated target peptide SMAP29 (Sheep Myeloid Antibacterial Peptide MAP-29, Anaspec).

C. Aptamer Amplification and Purification

Amplification and purification were performed as described in Example 3.

D. Selection Stringency and Feedback

Selection stringency and feedback were performed as described in Example 3.

E. Aptamer Properties

Figure 12A:
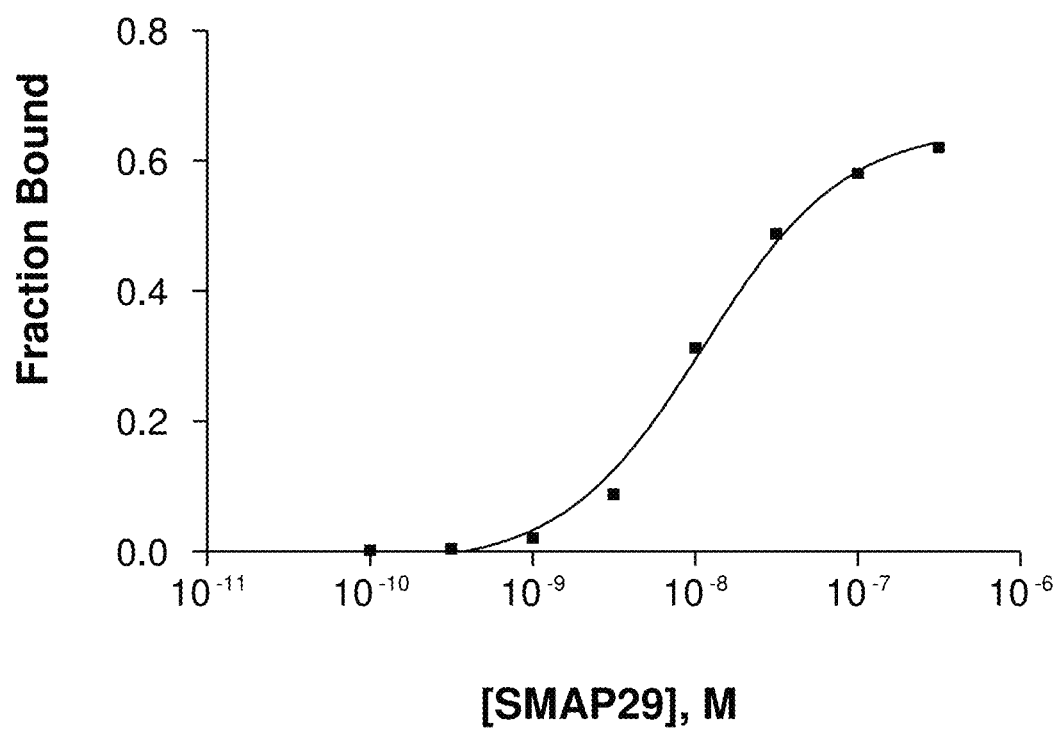
FIGS. 12A and 12B illustrate performance curves for a slow off-rate aptamer where the target was a peptide.
Figure 12B:
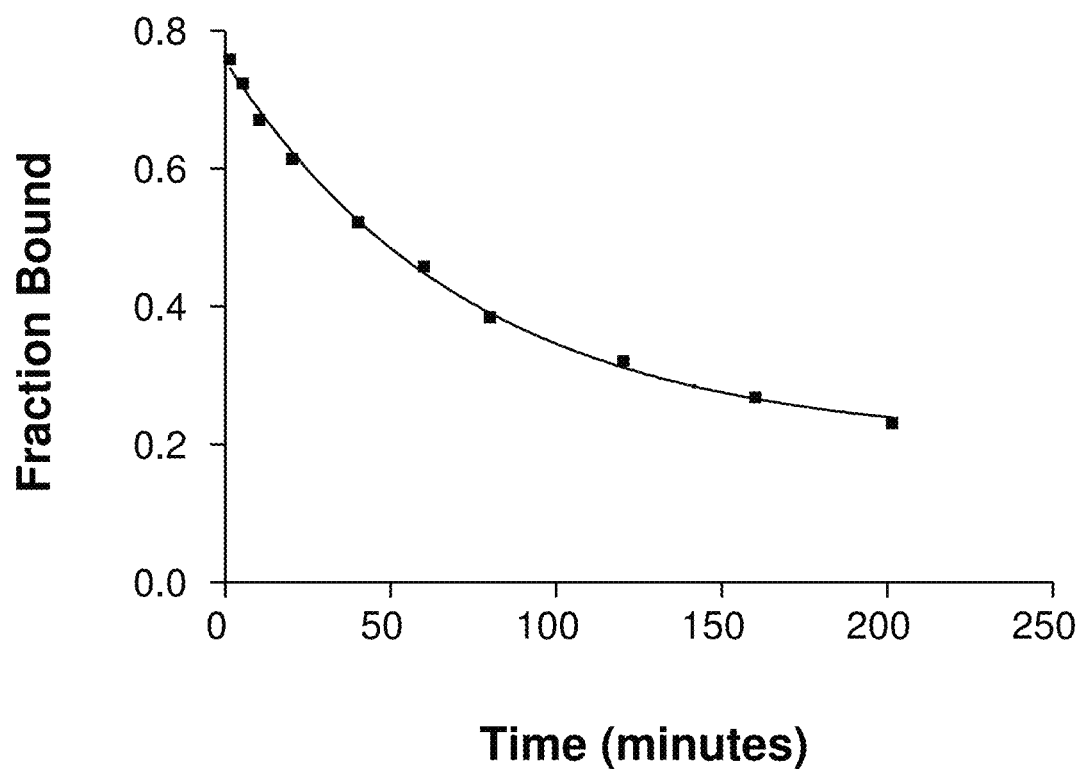

The equilibrium binding constant ($K_d$) of an aptamer from this selection was $1.2 \times 10^{-8}$ M (measured according to the protocol described in Example 1). The dissociation half-life ($t_{1/2}$) of this aptamer was 69 minutes (measured according to the protocol described in Example 3). Results are shown in FIG. 12A and FIG. 12B.

Example 7. Protein Measurements in Test Samples were Enabled by Aptamers with Slow Off-Rates A. Preparation of Aptamer/Primer Mixtures and Test Samples Aptamers with a biotin Cy3 detection label (4 nM each) were mixed with a 3x excess of capture probe (oligonucleotide complementary to the 3' fixed region of the aptamer containing a biotin tag and photocleavable element) in 1×SB17T and heated at 95° C. for 4 minutes, then 37° C. for 13 minutes, and diluted 1:4 in 1×SB17T. 55 uL of aptamer/primer mix was added to a microtiter plate (Hybaid # AB-0407) and sealed with foil. Test samples were prepared in a microtiter plate by mixing known concentrations of protein analytes in SB17T and diluting serially with SB17T.

B. Sample Equilibration 55 uL of aptamer/primer mix was added to 55 uL of test sample and incubated at 37° C. for 15 minutes in a foil-sealed microtiter plate. The final concentration of each aptamer in the equilibration mixture was 0.5 nM. After equilibration, all subsequent steps of this method were performed at room temperature unless otherwise noted.

C. Aptamer Capture and Free Protein Removal

A DuraPore filtration plate (Millipore HV cat# MAHVN4550) was washed once with 100 uL 1×SB17T by vacuum filtration. 133.3 uL 7.5% Streptavidin-agarose resin (Pierce) was added to each well and washed twice with 200 uL 1×SB17T. 100 uL of equilibrated samples was transferred to the Durapore plate containing the Streptavidin-agarose resin and incubated on a thermomixer (Eppendorf) at 800 rpm for 5 minutes. The resin was washed once with 200 uL 1×SB17T+100 uM biotin and once with 200 uL 1×SB17T.

D. Protein Tagging with Biotin 100 uL of 1.2 mM NHS-PEO4-biotin in SB17T, prepared immediately before use, was added to the resin with captured aptamer and aptamer:protein complexes and incubated on a thermomixer at 800 rpm for 20 minutes. The resin was washed five times with 200 uL 1×SB17T by vacuum filtration.

E. Slow Off-Rate Enrichment Process & Photocleavage

The drip director was removed from underside of the DuraPore plate and the plate was placed over a 1 mL microtiter collection plate. The resin was washed once with 200 uL 1×SB17T by centrifugation at 1000×g for 30 sec. 80 uL of 1×SB17T+10 mM dextran sulfate was added to the resin and irradiated with a BlackRay Mercury Lamp on a thermomixer at 800 rpm for 10 minutes. The DuraPore plate was transferred to a new 1 mL deepwell plate and centrifuged at 1000×g for 30 seconds to collect the photocleaved aptamer and protein:aptamer complexes.

F. Protein Capture and Free Aptamer Removal 50 uL of MyOne-streptavidin C1 paramagnetic beads (Invitrogen) (10 mg/mL in 1×SB17T) was added to a microtiter plate. The beads were separated with a magnet for 60 seconds and the supernatant was removed. 225 uL of photocleavage mixture was added to the beads and mixed for 5 minutes. The beads were washed four times with 200 uL 1×SB17T by separating the magnetic beads and replacing the wash buffer. The final wash buffer was removed.

G. Aptamer Elution 100 uL Sodium Phosphate Elution Buffer (10 mM $Na_2HPO_4$, pH 11) was added to the beads and mixed for 5 minutes. 90 uL of eluate was transferred to a microtiter plate and neutralized with 10 uL Sodium Phosphate Neutralization Buffer (10 mM $NaH_2PO_4$, pH 5).

H. Aptamer Hybridization to Microarrays

DNA arrays were prepared with oligonucleotide capture probes comprised of the complementary sequence of the variable region of each aptamer immobilized on a custom microscope slide support. Multiple arrays (subarrays) existed on each slide, and subarrays were physically separated by affixing a gasket (Grace) for sample application. Arrays were pretreated with 100 uL Blocking Buffer and incubated for 15 minutes at 65° C. on a thermomixer. 30 uL of high salt Hybridization Buffer was added to 90 uL of neutralized aptamer eluate in a microtiter plate, incubated at 95° C. for 5 minutes in a thermalcycler, and cooled to 65° C. at 0.1° C./second. Blocking Buffer was removed from the arrays and 110 uL of aptamer sample was added to the arrays and incubate in a humid chamber at 65° C. for 20 hours.

I. Array Washing

Aptamer sample was removed from the arrays, and the arrays were washed once with 200 uL of sodium phosphate Tween-20 wash buffer at 65° C., with the gasket in place, and three times with 25 mL sodium phosphate, Tween-20 wash buffer at 65° C. in a pap jar with the gasket removed. Arrays were dried with a nitrogen gun.

J. Quantitate Signal on Arrays

Array slides were scanned on a TECAN LS300 in an appropriate channel for Cy3 detection and Cy3 signal on each array feature was quantified.

Figure 11A:
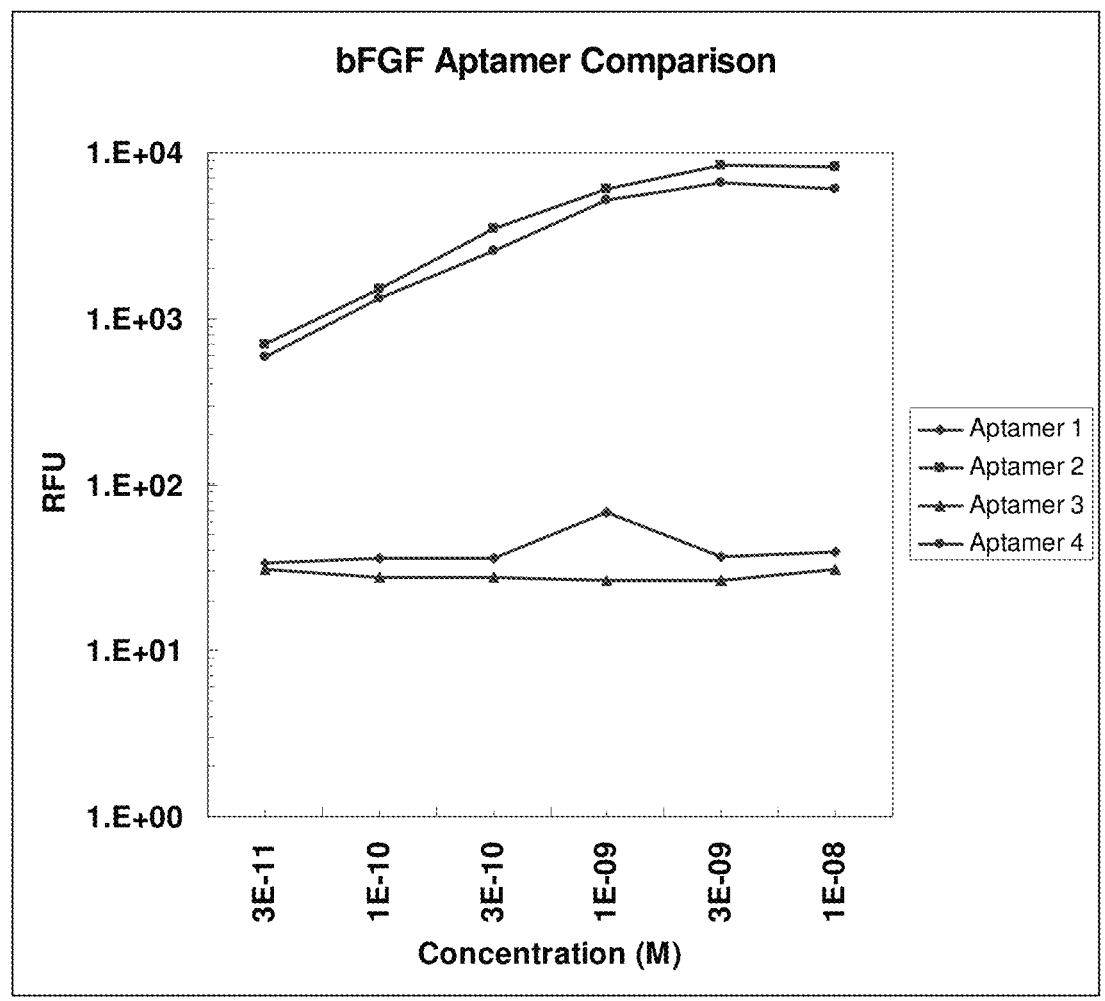
FIGS. 11A to 11C illustrate dose response curves for slow off-rate aptamers versus traditional aptamers for three different targets.
Figure 11B:
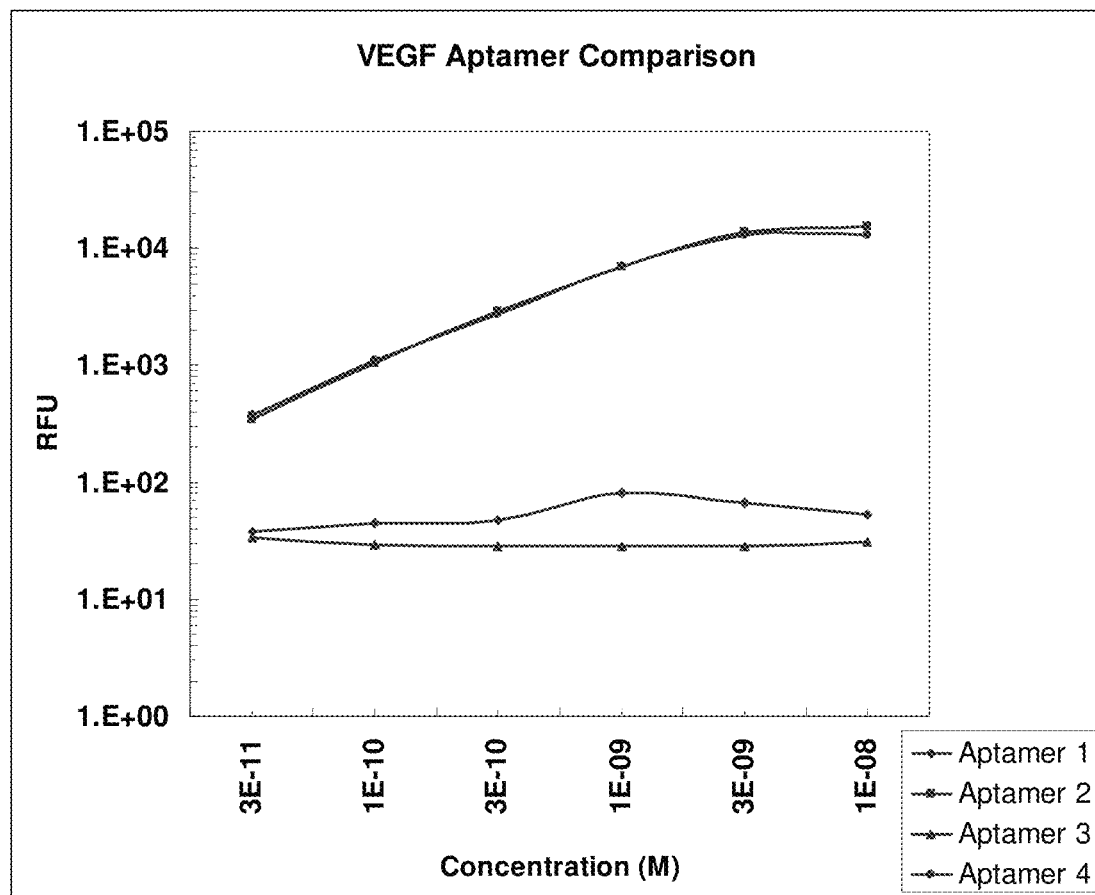
Figure 11C:
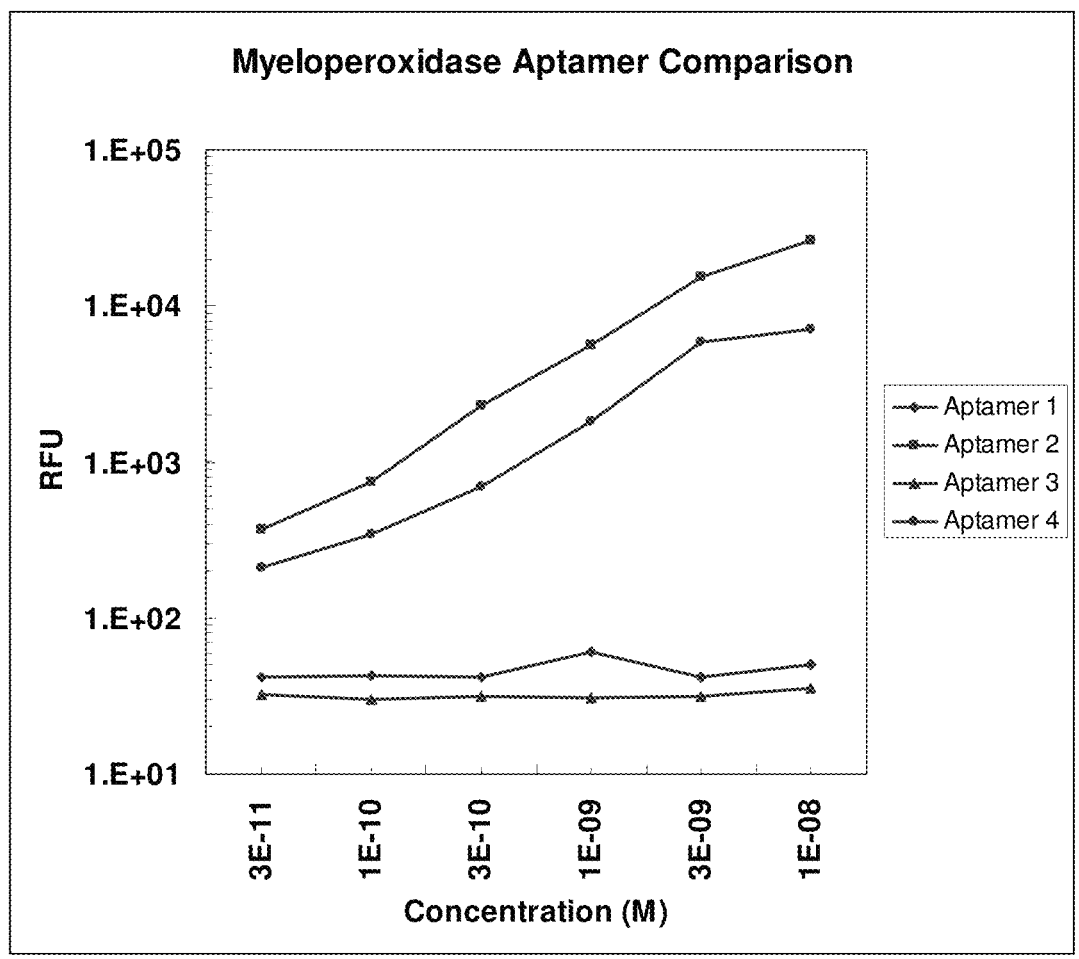

Results:

Apatmers specific to three different targets (bFGF, VEGF, and Myeloperoxidase) were produced using traditional SELEX methods and materials. A second set of aptamers specific to the same set of targets were made using 5-position modified nucleotides and selected for very slow off-rates for their respective targets. Aptamers made in the traditional process had measured off rates on the order of less than 5 minutes. Aptamers made with the modified nucleotides and using slow off-rate enrichment process during selection had off rates of greater than 20 minutes. Two sets of aptamers were made for each target by the two different methods for a total of 4 different aptamer populations for each target. The ability of these aptamer populations to measure analyte concentrations in test samples was evaluated as described above over a range of target concentrations. Relative signal from the DNA chip detection was plotted against the input target concentration. See FIGS. 11A to 11C. The response curve of the traditional aptamers was very flat and the sensitivity of the detection was fairly low. The sensitivity of detection of the respective targets with the slow off-rate aptamers was excellent. The data supports the need to use the slow off-rate aptamers for maximum analytic performance.

Example 8. Generation of High Affinity BndU Aptamers to Human Thrombin

A. Preparation of Candidate Mixture

A candidate mixture containing dATP, dCTP, dGTP, and BndUTP was prepared by polymerase extension of a primer with a 5' ANA chromophore and purified as described in Example 3.

B. Preparation of Target Protein

Human thrombin was tagged with biotin as describe in Example 2.

C. Aptamer Selection with Slow Off-Rate Enrichment and Photocrosslinking

Aptamer selection was performed as described in Example 3 with biotinylated human thrombin as the target.

D. Aptamer Amplification and Purification

Amplification and purification were performed as described in Example 3.

E. Selection Stringency and Feedback

Selection stringency and feedback were performed as described in Example 3.

F. Aptamer Properties

Figure 15:
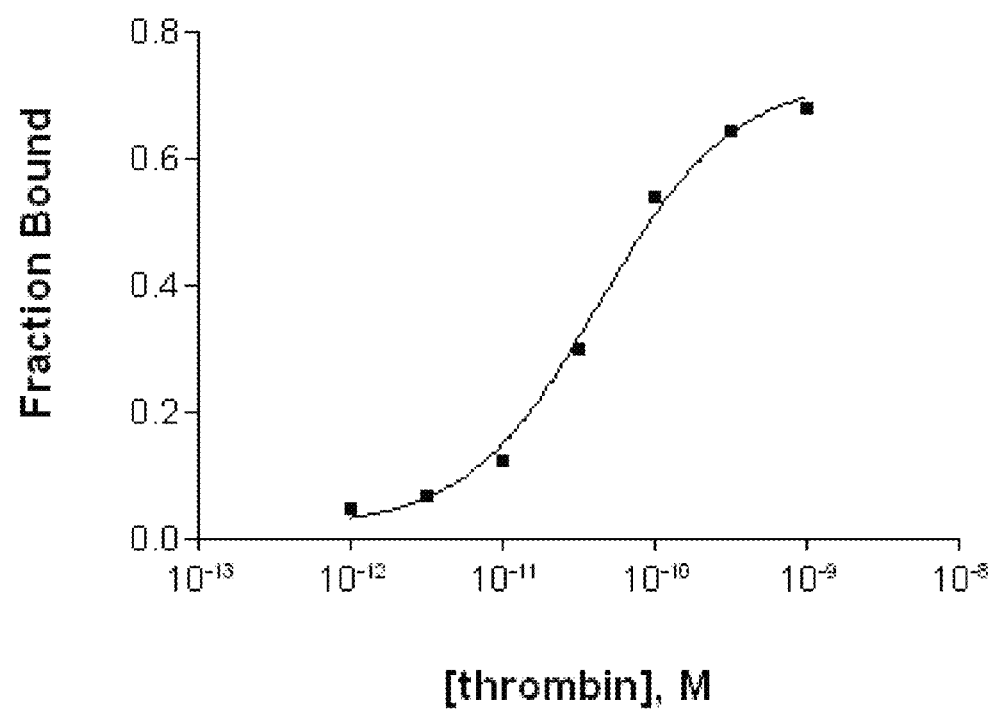
FIG. 15 illustrates a plot used in the determination of the binding constant for a slow off-rate aptamer containing C-5 modified pyrimidines to thrombin.

The equilibrium binding constant ($K_d$) of aptamer 2336-17 from this selection with a modified BndU was $4.4 \times 10^{-11}$ M (measured according to the protocol described in Example 1) as demonstrated in FIG. 15. In the art, single-stranded DNA aptamers to human thrombin were selected from a library comprised of natural dA, dC, dG, and dT nucleotides (Bock, et al., Selection of Single-Stranded DNA Molecules that Bind and Inhibit Human Thrombin, Nature 1992 355: 564-566). The binding affinities of the aptamers had $K_d$ values ranging from $2.5 \times 10^{-8}$ M to $2.0 \times 10^{-7}$ M. Using a similar protocol with a library comprised of natural dA, dC, dG, and modified 5-(1-pentynyl)-dUTP, aptamers were selected with $K_d$ values ranging from $4 \times 10^{-7}$ M to $1 \times 10^{-6}$ M (Latham, et al., The Application of a Modified Nucleotide in Aptamer Selection: Novel Thrombin Aptamers Containing 5-(1-Pentynyl)-2'-Deoxyuridine, Nucleic Acid Research 1994 22(14): 2817-2822).

A number of patents, patent application publications, and scientific publications are cited throughout and/or listed at the end of the description. Each of these is incorporated herein by reference in their entirety. Likewise, all publications mentioned in an incorporated publication are incorporated by reference in their entirety.

Examples in cited publications and limitations related therewith are intended to be illustrative and not exclusive. Other limitations of the cited publications will become apparent to those of skill in the art upon a reading of the specification and a study of the drawings.

The words "comprise", "comprises", and "comprising" are to be interpreted inclusively rather than exclusively.

What is claimed is:

1. A non-covalent complex of an aptamer and a target molecule, wherein the aptamer comprises at least one 5-position modified pyrimidine having a hydrophobic group attached via a linker to the 5-position of the pyrimidine, and wherein the aptamer has binding affinity for the target molecule.

2. The non-covalent complex of claim 1, wherein the hydrophobic group is selected from the group consisting of a benzyl, iso-butyl, indole and naphthyl.

3. The non-covalent complex of claim 1, wherein the 5-position modified pyrimidine is a 5-position modified uridine or cytosine.

4. The non-covalent complex of claim 1, wherein the target molecule is a protein or peptide.

5. The non-covalent complex of claim 1, wherein the linker is selected from the group of linkers consisting of:

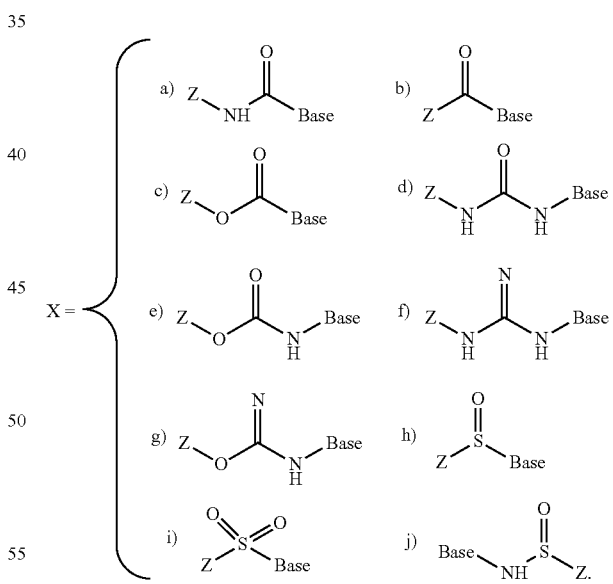

Base = Uridine (U) or Cytidine (C) (attachment is to the 5-position)
Z = R plus (CH$_2$)$_n$ connecting group, where n=0-3

* * * * *

SEQUENCE LISTING

```
<160> NUMBER OF SEQ ID NOS: 23

<210> SEQ ID NO 1
<211> LENGTH: 79
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (23)..(62)
<223> OTHER INFORMATION: n is a, c, g, or t

<400> SEQUENCE: 1
ababgtcttc ttgtcgtttc gcnnnnnnnn nnnnnnnnnn nnnnnnnnnn nnnnnnnnnn     60
nnggtggagt gtggtgagg                                                  79

<210> SEQ ID NO 2
<211> LENGTH: 25
<212> TYPE: DNA
<213> ORGANISM: Artificial
<220> FEATURE:
<223> OTHER INFORMATION: Synthetic
```

<400> SEQUENCE: 2
atatatatcc tcaccacact ccacc                                           25

<210> SEQ ID NO 3
<211> LENGTH: 30
<212> TYPE: DNA
<213> ORGANISM: Artificial
<220> FEATURE:
<223> OTHER INFORMATION: Synthetic

<400> SEQUENCE: 3
ababtttttt ttgtcttctt gtcgtttcgc                                      30

<210> SEQ ID NO 4
<211> LENGTH: 78
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (22)..(61)
<223> OTHER INFORMATION: n is a, c, g, or t

<400> SEQUENCE: 4
ababccgtcc tcctctccgt cnnnnnnnnn nnnnnnnnnn nnnnnnnnnn nnnnnnnnnn      60
ngggacactg ggtgcagg                                                   78

<210> SEQ ID NO 5
<211> LENGTH: 25
<212> TYPE: DNA
<213> ORGANISM: Artificial
<220> FEATURE:
<223> OTHER INFORMATION: Synthetic

<400> SEQUENCE: 5
atatatatcc tgcacccagt gtccc                                           25

<210> SEQ ID NO 6
<211> LENGTH: 29
<212> TYPE: DNA
<213> ORGANISM: Artificial
<220> FEATURE:
<223> OTHER INFORMATION: Synthetic

<400> SEQUENCE: 6
ababtttttt ttccgtcctc ctctccgtc                                       29

<210> SEQ ID NO 7
<211> LENGTH: 18
<212> TYPE: DNA
<213> ORGANISM: Artificial
<220> FEATURE:
<223> OTHER INFORMATION: Synthetic

<400> SEQUENCE: 7
gtcttcttgt cgtttcgc                                                   18

<210> SEQ ID NO 8
<211> LENGTH: 76
<212> TYPE: DNA
<213> ORGANISM: Artificial
<220> FEATURE:
<223> OTHER INFORMATION: Synthetic
<220> FEATURE:

<221> NAME/KEY: misc_feature
<222> LOCATION: (20)..(59)
<223> OTHER INFORMATION: n is a, c, g, or t

<400> SEQUENCE: 8
ababcccgct cgtcgtctgn nnnnnnnnnn nnnnnnnnnn nnnnnnnnnn nnnnnnnnnc    60
aggcagacgg tcactc                                                    76

<210> SEQ ID NO 9
<211> LENGTH: 25
<212> TYPE: DNA
<213> ORGANISM: Artificial
<220> FEATURE:
<223> OTHER INFORMATION: Synthetic

<400> SEQUENCE: 9
atatatatga gtgaccgtct gcctg                                          25

<210> SEQ ID NO 10
<211> LENGTH: 25
<212> TYPE: DNA
<213> ORGANISM: Artificial
<220> FEATURE:
<223> OTHER INFORMATION: Synthetic

<400> SEQUENCE: 10
atatatatga gtgaccgtct gcctg                                          25

<210> SEQ ID NO 11
<211> LENGTH: 25
<212> TYPE: DNA
<213> ORGANISM: Artificial
<220> FEATURE:
<223> OTHER INFORMATION: Synthetic

<400> SEQUENCE: 11
atatatatga gtgaccgtct gcctg                                          25

<210> SEQ ID NO 12
<211> LENGTH: 25
<212> TYPE: DNA
<213> ORGANISM: Artificial
<220> FEATURE:
<223> OTHER INFORMATION: Synthetic

<400> SEQUENCE: 12
atatatatga gtgaccgtct gcctg                                          25

<210> SEQ ID NO 13
<211> LENGTH: 25
<212> TYPE: DNA
<213> ORGANISM: Artificial
<220> FEATURE:
<223> OTHER INFORMATION: Synthetic

<400> SEQUENCE: 13
atatatatga gtgaccgtct gcctg                                          25

<210> SEQ ID NO 14
<211> LENGTH: 23
<212> TYPE: DNA
<213> ORGANISM: Artificial
<220> FEATURE:
<223> OTHER INFORMATION: Synthetic

<400> SEQUENCE: 14

```
tttttttttcc cgctcgtcgt ctg                                          23

<210> SEQ ID NO 15
<211> LENGTH: 27
<212> TYPE: DNA
<213> ORGANISM: Artificial
<220> FEATURE:
<223> OTHER INFORMATION: Synthetic

<400> SEQUENCE: 15
ababtttttt ttcccgctcg tcgtctg                                       27

<210> SEQ ID NO 16
<211> LENGTH: 79
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (23)..(62)
<223> OTHER INFORMATION: n is a, c, g, or t

<400> SEQUENCE: 16
ababgtgtct gtctgtgtcc tcnnnnnnnn nnnnnnnnnn nnnnnnnnnn nnnnnnnnnn   60
nnggtggagt gtggtgagg                                                79

<210> SEQ ID NO 17
<211> LENGTH: 25
<212> TYPE: DNA
<213> ORGANISM: Artificial
<220> FEATURE:
<223> OTHER INFORMATION: Synthetic

<400> SEQUENCE: 17
atatatatcc tcaccacact ccacc                                         25

<210> SEQ ID NO 18
<211> LENGTH: 25
<212> TYPE: DNA
<213> ORGANISM: Artificial
<220> FEATURE:
<223> OTHER INFORMATION: Synthetic

<400> SEQUENCE: 18
atatatatcc tcaccacact ccacc                                         25

<210> SEQ ID NO 19
<211> LENGTH: 25
<212> TYPE: DNA
<213> ORGANISM: Artificial
<220> FEATURE:
<223> OTHER INFORMATION: Synthetic

<400> SEQUENCE: 19
atatatatcc tcaccacact ccacc                                         25

<210> SEQ ID NO 20
<211> LENGTH: 25
<212> TYPE: DNA
<213> ORGANISM: Artificial
<220> FEATURE:
<223> OTHER INFORMATION: Synthetic

<400> SEQUENCE: 20
```

```
atatatatcc tcaccacact ccacc                                          25

<210> SEQ ID NO 21
<211> LENGTH: 25
<212> TYPE: DNA
<213> ORGANISM: Artificial
<220> FEATURE:
<223> OTHER INFORMATION: Synthetic

<400> SEQUENCE: 21
atatatatcc tcaccacact ccacc                                          25

<210> SEQ ID NO 22
<211> LENGTH: 26
<212> TYPE: DNA
<213> ORGANISM: Artificial
<220> FEATURE:
<223> OTHER INFORMATION: Synthetic

<400> SEQUENCE: 22 tttttttttgt gtctgtctgt gtcctc                                        26

<210> SEQ ID NO 23
<211> LENGTH: 30
<212> TYPE: DNA
<213> ORGANISM: Artificial
<220> FEATURE:
<223> OTHER INFORMATION: Synthetic

<400> SEQUENCE: 23
ababtttttt ttgtgtctgt ctgtgtcctc                                     30
```